United States Patent
Chakravarty et al.

(10) Patent No.: US 7,488,744 B2
(45) Date of Patent: Feb. 10, 2009

(54) INDOLE-TYPE DERIVATIVES AS INHIBITORS OF P38 KINASE

(75) Inventors: Sarvajit Chakravarty, Mountain View, CA (US); Sundeep Dugar, San Jose, CA (US); Qing Lu, Foster City, CA (US); Gregory R. Luedtke, Royal Oaks, CA (US); Babu J. Mavunkel, Sunnyvale, CA (US); John J. Perumattam, Los Altos, CA (US); Richard Tester, Alameda, CA (US)

(73) Assignee: Scios, Inc., Fremont, CA (US)

( * ) Notice: Subject to any disclaimer, the term of this patent is extended or adjusted under 35 U.S.C. 154(b) by 0 days.

(21) Appl. No.: 11/752,255

(22) Filed: May 22, 2007

(65) Prior Publication Data

US 2007/0232617 A1   Oct. 4, 2007

Related U.S. Application Data

(62) Division of application No. 10/654,840, filed on Sep. 3, 2003, now Pat. No. 7,220,763.

(60) Provisional application No. 60/408,493, filed on Sep. 3, 2002.

(51) Int. Cl.
  *A01N 43/64*   (2006.01)
  *A61K 31/41*   (2006.01)
  *C07D 209/04*   (2006.01)

(52) U.S. Cl. .................. 514/359; 548/400; 548/452; 548/469

(58) Field of Classification Search ............... 514/359; 548/400, 452, 469
See application file for complete search history.

(56) References Cited

U.S. PATENT DOCUMENTS

2005/0065344 A1   3/2005   Mavunkel et al.

FOREIGN PATENT DOCUMENTS

| WO | WO 96/40143 | 12/1996 |
|---|---|---|
| WO | WO 97/26252 | 7/1997 |
| WO | WO 98/06715 | 2/1998 |
| WO | WO 98/07425 | 2/1998 |
| WO | WO 99/61426 | 12/1999 |
| WO | WO 00/71535 A1 | 11/2000 |
| WO | WO 00/59904 | 12/2000 |
| WO | WO 02/42292 A2 | 5/2002 |
| WO | WO 02/44168 A2 | 6/2002 |

OTHER PUBLICATIONS

U.S. Appl. No. 60/395,693, filed Jul. 11, 2002, Scios Inc.
Colvin et al., Tetrahedron Letters 1982 vol. 23(37) pp. 3835-3836.
Jiang et al., The Journal of Biological Chemistry 1996 vol. 271(30) pp. 17920-17926.
Kumar et al., Biochemical and Biophysical Research Communications 1997 vol. 235 pp. 533-538.
Li et al., Biochemical and Biophysical Research Communications 1996 vol. 228 pp. 334-340.
Stein et al., The Journal of Biological Chemistry 1997 vol. 272(31) pp. 19509-19517.
Wang et al., The Journal of Biological Chemistry 1997 vol. 272(38) pp. 23668-23674.

*Primary Examiner*—James O. Wilson
*Assistant Examiner*—Paul V. Ward
(74) *Attorney, Agent, or Firm*—Morrison & Foerster LLP

(57) ABSTRACT

The invention is directed to methods to inhibit p38-α kinase using compounds comprising a phenyl or thienyl coupled through a piperidine or piperazine nucleus to an indole residue wherein the indole residue mandatorily has a substituent on the ring nitrogen which is an amino or substituted amino group.

32 Claims, No Drawings

INDOLE-TYPE DERIVATIVES AS INHIBITORS OF P38 KINASE

RELATED APPLICATIONS

This application is a divisional of U.S. Ser. No. 10/654,840 filed 3 Sep. 2003, which claims priority to U.S. Provisional Patent Application No. 60/408,493, filed 3 Sep. 2002. The contents of these documents are incorporated herein by reference.

FIELD OF THE INVENTION

The invention relates to treating various disorders associated with enhanced activity of kinase p38-α. More specifically, it concerns compounds that are related to indole derivatives substituted by an amine at position 1, coupled to piperazine- or piperidine-type moieties as useful in these methods.

BACKGROUND ART

A large number of chronic and acute conditions have been recognized to be associated with perturbation of the inflammatory response. A large number of cytokines participate in this response, including IL-1, IL-6, IL-8 and TNF. It appears that the activity of these cytokines in the regulation of inflammation rely at least in part on the activation of an enzyme on the cell signaling pathway, a member of the MAP kinase family generally known as p38 and alternatively known as CSBP and RK. This kinase is activated by dual phosphorylation after stimulation by physiochemical stress, treatment with lipopolysaccharides or with proinflammatory cytokines such as IL-1 and TNF. Therefore, inhibitors of the kinase activity of p38 are useful anti-inflammatory agents.

PCT applications WO98/06715, WO98/07425, and WO 96/40143, all of which are incorporated herein by reference, describe the relationship of p38 kinase inhibitors with various disease states. As mentioned in these applications, inhibitors of p38 kinase are useful in treating a variety of diseases associated with chronic inflammation. These applications list rheumatoid arthritis, rheumatoid spondylitis, osteoarthritis, gouty arthritis and other arthritic conditions, sepsis, septic shock, endotoxic shock, Gram-negative sepsis, toxic shock syndrome, asthma, adult respiratory distress syndrome, stroke, reperfusion injury, CNS injuries such as neural trauma and ischemia, psoriasis, restenosis, cerebral malaria, chronic pulmonary inflammatory disease, chronic obstructive pulmonary disease, cystic fibrosis, silicosis, pulmonary sarcosis, bone fracture healing, bone resorption diseases such as osteoporosis, soft tissue damage, graft-versus-host reaction, Crohn's Disease, ulcerative colitis including inflammatory bowel disease (IBD) and pyresis.

The above-referenced PCT applications disclose compounds which are p38 kinase inhibitors said to be useful in treating these disease states. These compounds are either imidazoles or are indoles substituted at the 3- or 4-position with a piperazine ring linked through a carboxamide linkage. Additional compounds which are conjugates of piperazines with indoles are described as insecticides in WO97/26252, also incorporated herein by reference.

Certain aroyl/phenyl-substituted piperazines and piperidines which inhibit p38-α kinase are described in PCT publication WO00/12074 published 9 Mar. 2000. In addition, indolyl substituted piperidines and piperazines which inhibit this enzyme are described in PCT publication No. WO99/61426 published 2 Dec. 1999. Carbolene derivatives of piperidine and piperazine as p38-α inhibitors are described in PCT/US00/07934 filed 24 Mar. 2000.

A genus of compounds focused on particular substituents on an indole-derived moiety, again linked through piperidines or piperazines to an aromatic system is described in PCT publication WO 00/71535 published 30 Nov. 2000. The contents of this publication are incorporated herein by reference.

DISCLOSURE OF THE INVENTION

The invention is directed to methods and compounds useful in treating conditions that are characterized by enhanced p38-α activity. These conditions include inflammation, proliferative diseases, and certain cardiovascular disorders as well as Alzheimer's disease as further described below.

Compounds of the invention have been found to inhibit p38 kinase, the α-isoform in particular, and are thus useful in treating diseases mediated by these activities. The compounds of the invention are of the formula

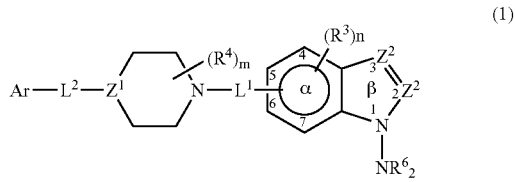

(1)

and the pharmaceutically acceptable salts thereof, wherein one $Z^2$ is CA and the other is $CR^1$, wherein $R^1$ is hydrogen or a noninterfering substituent;

A is $-W_i-COX_jY$ wherein Y is $COR^2$ wherein $R^2$ is hydrogen or a noninterfering substituent, each of W and X is a spacer preferably of 2-6 Å, and each of i and j is independently 0, 1 or 2;

each $R^6$ is independently H, or a noninterfering substituent, wherein two $R^6$ may optionally form a 5-7 membered ring including the nitrogen to which they are bound;

each $R^3$ is independently a noninterfering substituent;

n is 0-3;

each of $L^1$ and $L^2$ is a linker;

each $R^4$ is independently a noninterfering substituent;

m is 0-4;

$Z^1$ is $CR^5$ or N wherein $R^5$ is hydrogen or a noninterfering substituent;

Ar is a phenyl or thienyl group substituted with 0-5 noninterfering substituents, wherein two noninterfering substituents can form a fused ring; and the distance between the atom of Ar linked to $L^2$ and the center of the α ring is preferably 4.5-24 Å.

In other aspects, the invention is directed to pharmaceutical compositions containing at least one component of formula (1) or its salt. In other aspects, the invention is directed to methods of treating inflammation or proliferative conditions using these compounds. The invention is also directed to treating conditions associated with cardiac failure and Alzheimer's disease using the invention compounds.

MODES OF CARRYING OUT THE INVENTION

The compounds of formula (1) are useful in treating conditions which are characterized by overactivity of p38 kinase, in particular the α-isoform. Conditions "characterized by enhanced p38-α activity" include those where this enzyme is present in increased amount or wherein the enzyme has been modified to increase its inherent activity, or both. Thus, "enhanced activity" refers to any condition wherein the effectiveness of these proteins is undesirably high, regardless of the cause.

The compounds of the invention are useful in conditions where p38-α kinase shows enhanced activity. These conditions are those in which fibrosis and organ sclerosis are caused by, or accompanied by, inflammation, oxidation injury, hypoxia, altered temperature or extracellular osmolarity, conditions causing cellular stress, apoptosis or necrosis. These conditions include ischemia-reperfusion injury, congestive heart failure, progressive pulmonary and bronchial fibrosis, hepatitis, arthritis, inflammatory bowel disease, glomerular sclerosis, interstitial renal fibrosis, chronic scarring diseases of the eyes, bladder and reproductive tract, bone marrow dysplasia, chronic infectious or autoimmune states and traumatic or surgical wounds. These conditions, of course, would be benefited by compounds which inhibit p38-α. Methods of treatment with the compounds of the invention are further discussed below.

The Invention Compounds

The compounds useful in the invention are derivatives of indole-type compounds containing two mandatory substituents. One substituent, A, is at a position corresponding to the 2- or 3-position of indole. The other mandatory substituent is an amino substituent at the indole nitrogen.

In the description above, certain positions of the molecule are described as permitting "noninterfering substituents." This terminology is used because the substituents in these positions generally speaking are not relevant to the essential activity of the molecule taken as a whole. A wide variety of substituents can be employed in these positions, and it is well within ordinary skill to determine whether any particular arbitrary substituent is or is not "noninterfering."

As used herein, a "noninterfering substituent" is a substituent which leaves the ability of the compound of formula (1) to inhibit p38-α activity qualitatively intact. Thus, the substituent may alter the degree of inhibition of p38-α. However, as long as the compound of formula (1) retains the ability to inhibit p38-α activity, the substituent will be classified as "noninterfering." A number of assays for determining the ability of any compound to inhibit p38-α activity are available in the art. A whole blood assay for this evaluation is illustrated below: the gene for p38-α has been cloned and the protein can be prepared recombinantly and its activity assessed, including an assessment of the ability of an arbitrarily chosen compound to interfere with this activity. The essential features of the molecule are tightly defined. The positions which are occupied by "noninterfering substituents" can be substituted by conventional organic moieties as is understood in the art. It is irrelevant to the present invention to test the outer limits of such substitutions. The essential features of the compounds are those set forth with particularity herein.

In addition, $L^1$ and $L^2$ are described herein as linkers and are intended to impart a distance between portions of the molecule. Typical linkers include alkylene, i.e. alkenylene—i.e., an alkylene moiety which contains a double bond, including a double bond at one terminus. Other suitable linkers include, for example, substituted alkylenes or alkenylenes, including carbonyl moieties, and the like. In a preferred embodiment, $L^1$ is a carboxy group. In another preferred embodiment, $L^2$ is alkylene, or an alkylene substituted with a phenyl or methyl group.

As used herein, "hydrocarbyl residue" refers to a residue which contains only carbon and hydrogen. The residue may be aliphatic or aromatic, straight-chain, cyclic, branched, saturated or unsaturated. The hydrocarbyl residue, when so stated however, may contain heteroatoms over and above the carbon and hydrogen members of the substituent residue. Thus, when specifically noted as containing such heteroatoms, the hydrocarbyl residue may also contain carbonyl groups, amino groups, hydroxyl groups and the like, or may contain heteroatoms within the "backbone" of the hydrocarbyl residue.

As used herein, "inorganic residue" refers to a residue that does not contain carbon. Examples include, but are not limited to, halo, hydroxy, $NO_2$ or $NH_2$.

As used herein, the term "alkyl," "alkenyl" and "alkynyl" include straight- and branched-chain and cyclic monovalent substituents. Examples include methyl, ethyl, isobutyl, cyclohexyl, cyclopentylethyl, 2-propenyl, 3-butynyl, and the like. Typically, the alkyl, alkenyl and alkynyl substituents contain 1-10C (alkyl) or 2-10C (alkenyl or alkynyl). Preferably they contain 1-6C (alkyl) or 2-6C (alkenyl or alkynyl). Heteroalkyl, heteroalkenyl and heteroalkynyl are similarly defined but may contain 1-2 O, S or N heteroatoms or combinations thereof within the backbone residue.

As used herein, "acyl" encompasses the definitions of alkyl, alkenyl, alkynyl and the related hetero-forms which are coupled to an additional residue through a carbonyl group.

"Aromatic" moiety refers to a monocyclic or fused bicyclic moiety such as phenyl or naphthyl, including those that contain one or more heteroatoms; "heteroaromatic" itself refers to monocyclic or fused bicyclic ring systems containing one or more heteroatoms selected from O, S and N. The inclusion of a heteroatom permits inclusion of 5-membered rings as well as 6-membered rings. Thus, typical aromatic systems include phenyl, naphthyl, pyridyl, pyrimidyl, indolyl, benzimidazolyl, benzotriazolyl, isoquinolyl, quinolyl, benzothiazolyl, benzofuranyl, thienyl, furyl, pyrrolyl, thiazolyl, oxazolyl, imidazolyl and the like. Any monocyclic or fused ring bicyclic system which has the characteristics of aromaticity in terms of electron distribution throughout the ring system is included in this definition. Typically, the ring systems contain 5-12 ring member atoms.

Similarly, "arylalkyl" and "heteroarylalkyl" refer to aromatic and heteroaromatic systems which are coupled to another residue through a carbon chain, including substituted or unsubstituted, saturated or unsaturated, carbon chains, typically of 1-6C. These carbon chains may also include a carbonyl group, thus making them able to provide these substituents as acyl moieties.

When the compounds of Formula 1 contain one or more chiral centers, the invention includes optically pure forms as well as mixtures of stereoisomers or enantiomers.

With respect to the portion of the compound between the atom of Ar bound to $L^2$ and ring α, in one embodiment, $L^1$ and $L^2$ are linkers which space the substituent Ar from ring α preferably at a distance of 4.5-24 Å, preferably 6-20 Å, more preferably 7.5-10 Å. The distance is measured from the center of the α ring to the atom of Ar to which the linker $L^2$ is attached. Typical, but nonlimiting, embodiments of $L^1$ and $L^2$ are CO and isosteres thereof, or optionally substituted isosteres, or longer chain forms. $L^1$ and/or $L^2$ may be alkylene or alkenylene optionally substituted with noninterfering substituents or $L^1$ or $L^2$ may be or may include a heteroatom such as N, S or O. Such substituents include, but are limited to, a moiety selected from the group consisting of alkyl, alkenyl, alkynyl, aryl, arylalkyl, acyl, aroyl, heteroaryl, heteroalkyl, heteroalkenyl, heteroalkynyl, heteroarylalkyl, NH-aroyl, arylacyl, heteroarylacyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein said two substituents can be joined to form a carbonyl moiety or an oxime, oximeether, oximeester or ketal of said carbonyl moiety.

Isosteres of CO and $CH_2$, include SO, $SO_2$, or CHOH. CO and $CH_2$ are preferred.

Ar is phenyl or thienyl that can be optionally substituted.

Each substituent on Ar is independently a hydrocarbyl residue (1-20C) containing 0-5 heteroatoms selected from O, S and N, or is an inorganic residue. Preferred substituents include those selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, arylacyl, heteroarylacyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two of said optional substituents on adjacent positions can be joined to form a fused, optionally substituted aromatic or nonaromatic, saturated or unsaturated ring which contains 3-8 members. More preferred substituents include halo, alkyl (1-4C), alkoxy (1-6C) and more preferably, fluoro, chloro and methyl. These substituents may occupy all available positions of the aryl ring of Ar, preferably 1-2 positions, most preferably one position or the phenyl or thienyl may be unsubstituted. These substituents may be optionally substituted with substituents similar to those listed. Of course some substituents, such as halo, are not further substituted, as known to one skilled in the art.

Between $L^1$ and $L^2$ is a piperidine or piperazine moiety of the following formula:

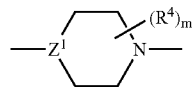

$Z^1$ is $CR^5$ or N wherein $R^5$ is H or a noninterfering substituent. The noninterfering substituents $R^5$ include, without limitation, halo, alkyl, alkoxy, aryl, arylalkyl, aryloxy, heteroaryl, acyl, carboxy, or hydroxy. Preferably, $R^5$ is H, alkyl, OR, $NR_2$, SR or halo, where R is H or alkyl. Preferred embodiments include compounds wherein $Z^1$ is CH or N.

$R^4$ represents a noninterfering substituent such as a hydrocarbyl residue (1-20C) containing 0-5 heteroatoms selected from O, S and N. Preferably $R^4$ is alkyl, alkoxy, aryl, arylalkyl, aryloxy, heteroalkyl, heteroaryl, heteroarylalkyl, RCO, acyl, halo, CN, OR, NRCOR, or $NR_2$, wherein R is H, alkyl (preferably 1-4C), aryl, or hetero forms thereof. Each appropriate substituent is itself unsubstituted or substituted with 1-3 substituents. These substituents are preferably independently selected from a group that includes alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof. Two of $R^4$ on adjacent positions can be joined to form a fused, optionally substituted aromatic or nonaromatic, saturated or unsaturated ring which contains 3-8 members, or $R^4$ is =O or an oxime, oximeether, oximeester or ketal thereof. $R^4$ may occur m times on the ring; m is an integer of 0-4. Preferred embodiments of $R^4$ comprise alkyl (1-4C) especially two alkyl substituents, and carbonyl.

Most preferably $R^4$ comprises two methyl groups at positions 2 and 5 or 3 and 6 of a piperidinyl or piperazinyl ring, or =O preferably at the 5-position of the ring. The substituted forms may be chiral and an isolated enantiomer may be preferred.

$R^3$ also represents a noninterfering substituent. Such substituents include hydrocarbyl residues (1-6C) containing 0-2 heteroatoms selected from O, S and/or N and inorganic residues. n is an integer of 0-3, preferably 0 or 1. Preferably, the substituents represented by $R^3$ are independently halo, alkyl, heteroalkyl, OCOR, OR, NRCOR, SR, or $NR_2$, wherein R is H, alkyl, aryl, or heteroforms thereof. More preferably $R^3$ substituents are selected from alkyl, alkoxy or halo, and most preferably methoxy, methyl, and chloro. Most preferably, n is 0 and the α ring is unsubstituted, except for $L^1$ or n is 1 and $R^3$ is halo, alkoxy or lower alkyl.

Each $R^6$ is independently H, alkyl (1-6C), alkenyl (2-6C), alkynyl (2-6C), acyl (1-6C), aryl, arylalkyl or arylacyl, wherein all of the foregoing may also contain one or more heteroatoms. All of these substituents as $R^6$, except hydrogen, can be optionally substituted by halo, OCOR, OR, NRCOR, SR, or $NR_2$ wherein R is H, alkyl, alkenyl or aryl, or a heteroatom form thereof. In addition, the $R^6$ substituents, including any substituents thereon, may form a cyclic nitrogen containing ring. Preferably, each $R^6$ is hydrogen, alkyl (1-4C) or aminoalkyl, including cyclic forms obtained by bridging two $R^6$ substituents. Preferred embodiments include substituents on the indole nitrogen which are amino, dimethylamino, piperazinyl, piperidinyl, oxazolyl and the like. In another preferred embodiment, one $R^6$ is H and the other $R^6$ is COR where R is preferably methyl; or each $R^6$ is alkyl, more preferably methyl. In another preferred embodiment, were one $R^6$ is H, the other $R^6$ is a substituent other than H.

The mandatory substituent $NR^6_2$ contributes to the superior activity profile of the invention compounds.

Preferably, the mandatory substituent CA is in the 3-position. Regardless of which position this substituent occupies, the other position is $CR^1$. Preferred embodiments of $R^1$ include hydrogen, alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof. Most preferably, $R^1$ is H, alkyl, such as methyl. Other preferable forms of $R^1$ include H, alkyl, acyl, aryl, arylalkyl, heteroalkyl, heteroaryl, halo, OR, $NR_2$, SR, NRCOR, alkyl-OOR, RCO, COOR, and CN, wherein each R is independently H, alkyl, or aryl or heteroforms thereof.

A is —$W_i$—$COX_jY$ wherein Y is $COR^2$ wherein $R^2$ is a noninterfering substituent. Each of W and X is a spacer and may be, for example, optionally substituted alkyl, alkenyl, or alkynyl, each of i and j is 0 or 1. Preferably, W and X are unsubstituted. Preferably, j is 0 so that the two carbonyl groups are adjacent to each other. Preferably, also, i is 0 so that the proximal CO is adjacent the ring. However, compounds wherein the proximal CO is spaced from the ring can readily be prepared by selective reduction of an initially glyoxal substituted β ring. In the most preferred embodiments of the invention, the α/β ring system is an indole containing CA in position 3- and wherein A is $COCOR^2$.

The noninterfering substituent represented by $R^2$, when $R^2$ is other than H, is a hydrocarbyl residue (1-20C) containing 0-5 heteroatoms selected from O, S and/or N or is an inorganic residue. Preferred are embodiments wherein $R^2$ is H, or is straight or branched chain alkyl, alkenyl, alkynyl, aryl, arylalkyl, heteroalkyl, heteroaryl, or heteroarylalkyl, each optionally substituted with halo, alkyl, heteroalkyl, OR, NR$_2$, OCOR, NRCOR, NRCONR$_2$, NRSO$_2$R, NRSO$_2$NR$_2$, OCONR$_2$, CONR$_2$, or R$_3$Si wherein each R is independently H, alkyl, alkenyl or aryl or the heteroatom-containing forms thereof, or wherein R$^2$ is OR, NR$_2$, SR, NRCONR$_2$, OCONR$_2$, or NRSO$_2$NR$_2$, wherein each R is independently H, alkyl, alkenyl or aryl or the heteroatom-containing forms thereof, and wherein two R attached to the same atom may form a 3-8 member ring and wherein said ring may further be substituted by alkyl, alkenyl, alkynyl, aryl, arylalkyl, heteroalkyl, heteroaryl, heteroarylalkyl, each optionally substituted with halo, SR, OR, NR$_2$, OCOR, NRCOR, NRCONR$_2$, NRSO$_2$R, NRSO$_2$NR$_2$, OCONR$_2$, or R$_3$Si wherein each R is independently H, alkyl, alkenyl or aryl or the heteroatom-containing forms thereof wherein two R attached to the same atom may form a 3-8 member ring, optionally substituted as defined above. In a more preferred embodiment, R$^2$ is NR$_2$ and even more preferably, when one R of NR$_2$ is methyl, the other is a substituent other than methyl, for example, NR$_2$ is NHCH$_3$, N(CH$_3$)CH$_2$CHCH$_2$ or N(CH$_3$)OCH$_3$. In another preferred embodiment R$^2$ is NR$_2$ wherein each R$_2$ is other than methyl, preferably

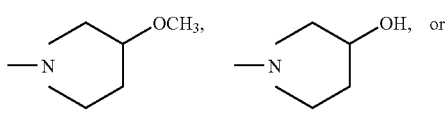

and more preferably

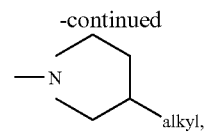

preferably

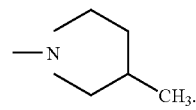

Other preferred embodiments of R$^2$ are H, alkyl, heteroarylalkyl, —NR$_2$, aryl, heteroaryl, —COOR, —NHRNR$_2$, heteroaryl-COOR, heteroaryloxy, —OR, heteroaryl-NR$_2$, —NROR and where R is H or alkyl. Most preferably R$^2$ is isopropyl piperazinyl, methyl piperazinyl, dimethylamine, piperazinyl, isobutyl carboxylate, oxycarbonylethyl, morpholinyl, aminoethyldimethylamine, isobutyl carboxylate piperazinyl, oxypiperazinyl, ethylcarboxylate piperazinyl, methoxy, ethoxy, hydroxy, methyl, amine, aminoethyl pyrrolidinyl, aminopropanediol, piperidinyl, pyrrolidinyl-piperidinyl, or methyl piperidinyl.

The compounds of formula (1) may be supplied in the form of their pharmaceutically acceptable acid-addition salts including salts of inorganic acids such as hydrochloric, sulfuric, hydrobromic, or phosphoric acid or salts of organic acids such as acetic, tartaric, succinic, benzoic, salicylic, and the like. If a carboxyl moiety is present on the compound of formula (1), the compound may also be supplied as a salt with a pharmaceutically acceptable cation.

Synthesis of the Invention Compounds

The following Reaction Scheme is illustrative of the conversion of a 4-benzyl piperidinyl-indole-5-carboxamide to the glyoxalic acid compounds of the invention and derivatives thereof.

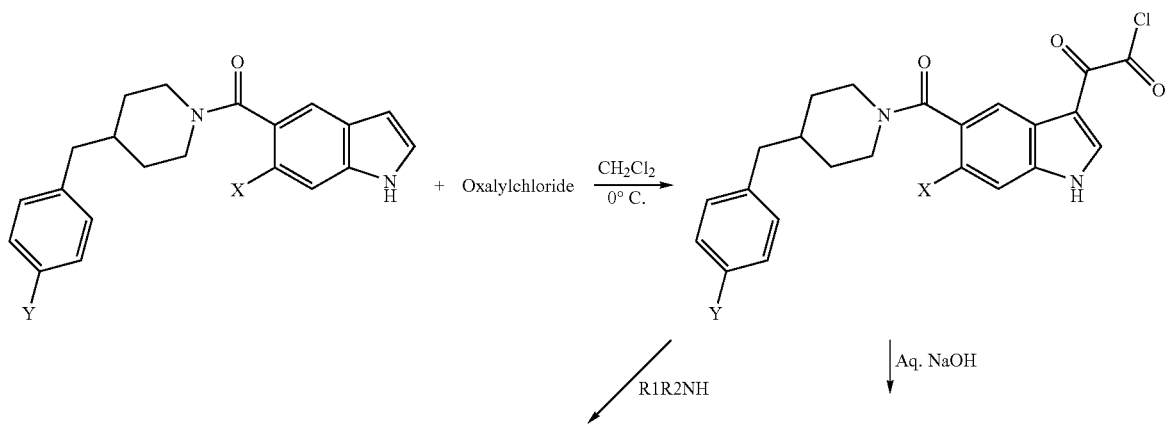

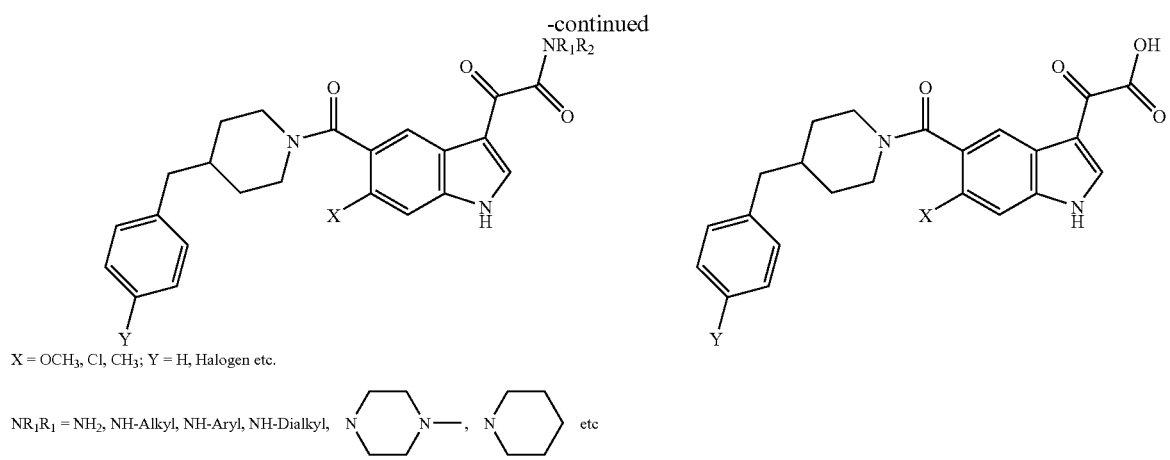

X = OCH₃, Cl, CH₃; Y = H, Halogen etc.

NR₁R₁ = NH₂, NH-Alkyl, NH-Aryl, NH-Dialkyl, 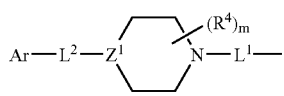 etc

Of course, the 4-benzyl piperidinyl carbonyl of the illustration at position 5 may be generalized as Ar—L²—Z¹—[ring with (R⁴)ₘ]—N—L¹— and the glyoxal type substituent at position 3 can be generalized to $W_iCOX_jY$.

Methods to synthesize the compounds of the invention are, in general, known in the art.

The following general schemes illustrate such methods.

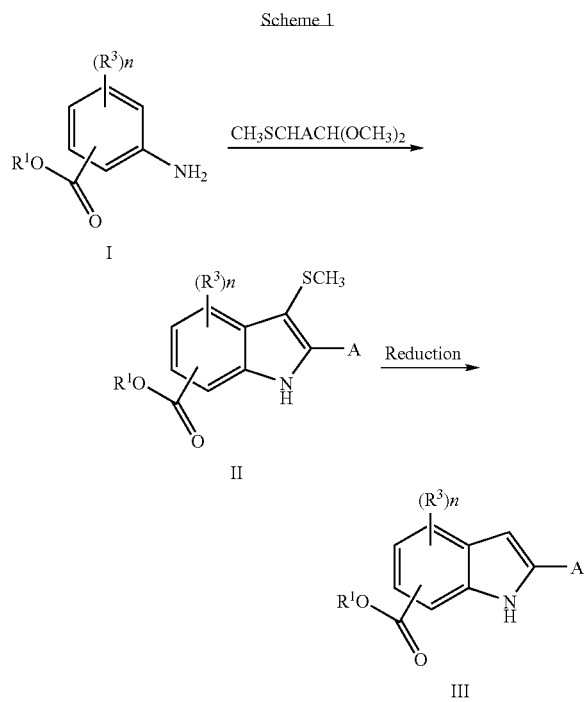

Substituted amino benzoic acid esters such as I can be treated with reagents such as thiomethylacetaldehyde dimethyl acetal and N-chlorosuccinamide in methylene chloride at low temperature followed by the treatment with a base such as triethylamine at reflux in methylene chloride, dichloroethane or chloroform to give indoles II, Scheme 1. Treatment with reagents such as Raney-Nickel in an appropriate solvent such as ethanol, methanol or isopropanol will yield the corresponding indole carboxylic acid ester which when hydrolyzed under base conditions will give the desired substituted indole carboxylic acid.

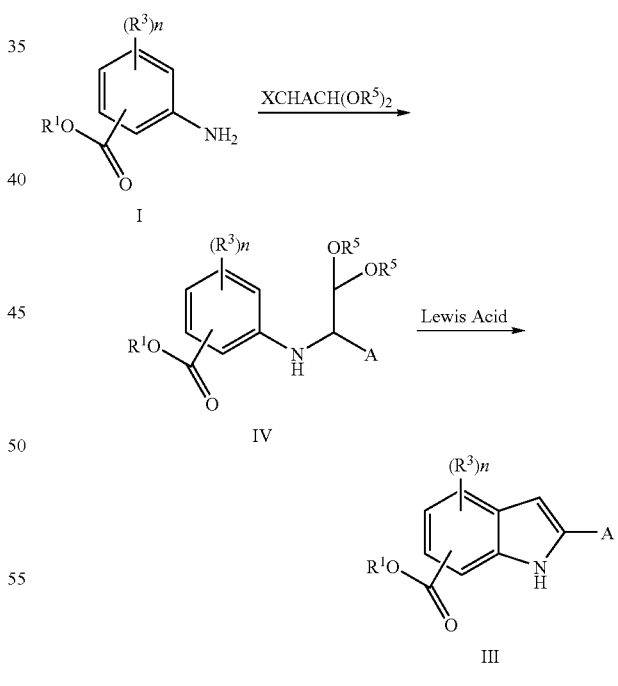

Alternatively, substituted amino benzoic acid esters I can be converted to the ketals IV, Scheme 2, with an appropriate aldehyde under conditions of reductive alkylation with reagents such as sodium triacetoxyborohydride in acetic acid in the presence of sodium sulfate. The amines can then be treated with lewis acids such as aluminum chloride, titanium chloride, BF₃-etherate in dichloromethane or dichloroethane, under reflux to give the corresponding substituted indole methyl esters, with appropriate substitutions.

Scheme 3

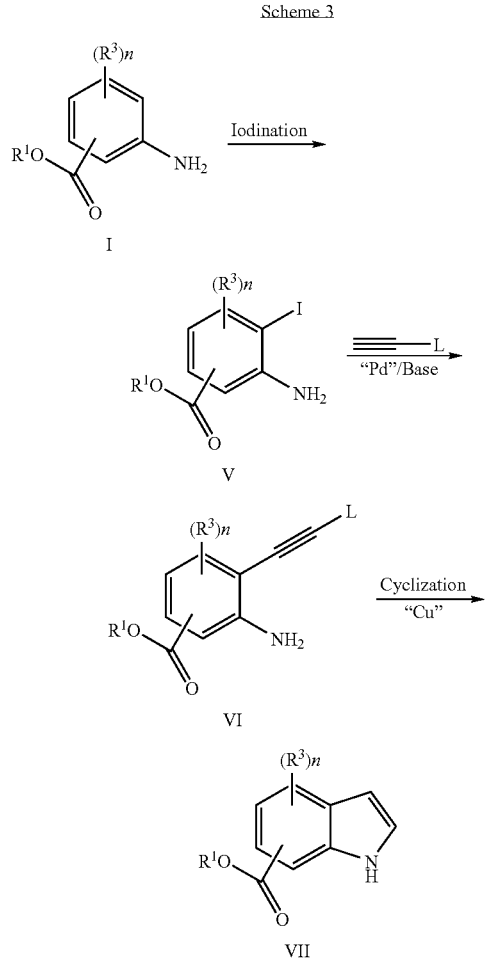

L = OR or SiR$_3$

Another method could involve the treatment of the substituted amino benzoic acid esters I with iodine and sodium periodate in an appropriate solvent such as dimethyformamide, to give the corresponding iodo aniline V, Scheme 3. This can be coupled with an acetylene such as trimethyl silyl acetylene or ethylethynyl ether in the presence of an appropriate catalysts such as palladium and copper and a base such as triethylamine to give the silyl coupled product such as VI. Subsequent cyclization in a solvent such as dimethylformamide and in the presence of a catalyst such as copper iodide would give the appropriately substituted indoles VII.

Scheme 4

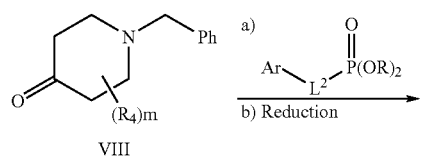

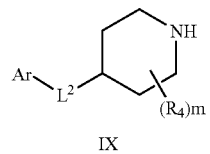

Synthesis of the required piperidines can be achieved by treating an appropriate piperidone such as VIII, Scheme 4, with substituted benzyl phosphonate esters in the presence of a base such as sodium hydride to give alkenes which can be reduced to the corresponding substituted 4-benzylpiperidine such as IX. The hydrogenations are typically done in the presence of catalytic metals in solvents such as methanol, ethanol and ethyl acetate.

Scheme 5

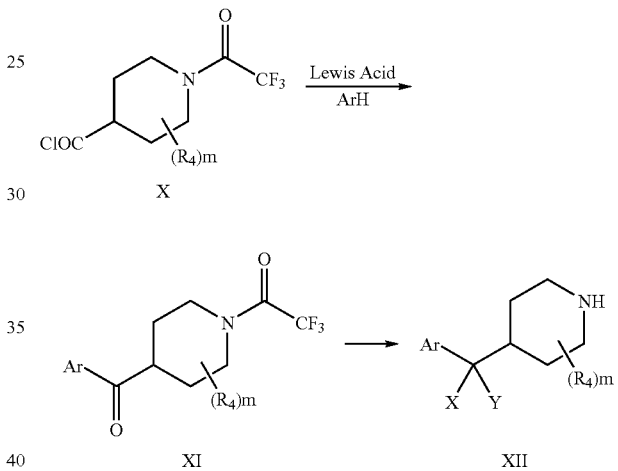

An alternate method could involve isonipecotoyl chlorides such as X which can be used to acylate appropriately substituted benzenes (ArH) in the presence of a lewis acid such as aluminum chloride to give the ketones XI, Scheme 5. Further modifications of the carbonyl moiety of XI using methods and routes generally known can then lead to the desired compounds XII.

Scheme 6

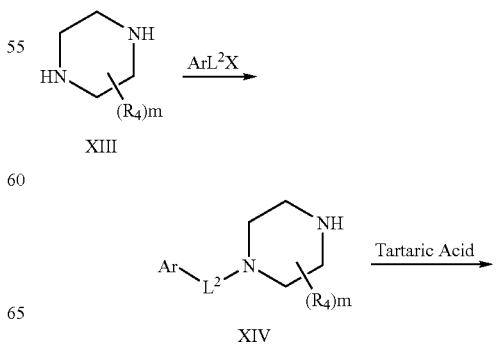

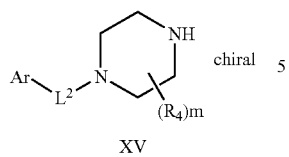

Substituted piperazines can be reacted with various and appropriate ArL²X in the presence or absence of a base or other catalytic reagent to give the substituted piperazines XV, Scheme 6. These can be further resolved to the chiral components with the use a chiral resolving agent such as tartaric acid to give either enantiomers of the substituted piperazines XV.

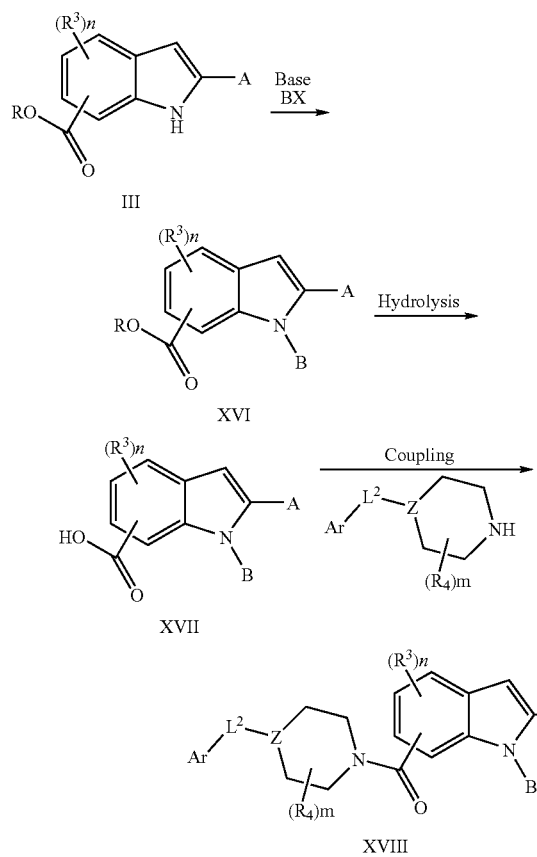

Compounds III can be treated with halides, acid chlorides and other electrophiles (BX), Scheme 7, containing a variety of different substituents, in the presence of a base such as sodium hydride, in a variety of different solvents, to give compounds of type XVI. These can then be converted to the corresponding acids XVII by treatment with appropriate reagents such as an aqueous base. The acids are then coupled to substituted amines IX, XII or XV using a coupling agent such as EDAC.HCl in a variety of solvents including methylene chloride, dimethyl formamide, to give compounds XVIII.

Compounds XVIII can be first treated with acid chlorides such as oxalyl chloride in methylene chloride under anhydrous conditions followed by treatment with a variety of nucleophiles WH to give compounds of type XIX, Scheme 8.

Scheme 9

The indole nitrogen can be aminated with an N-amination reagent, such as those described in U.S. Provisional Patent Appln. 60/395,693, filed 11 Jul. 2002 entitled "Improved Reagents for N-Amination", U.S. patent application Ser. No. 10/618,573, filed 11 Jul. 2003 entitled "Improved Reagents for N-Amination", and *Tetrahedron Lett.*, vol. 23, No. 37, pages 3835-3836, 1982, all of which are incorporated herein by reference, compound XX reacts with an N-amination reactant to give the indole N-substituted compounds XXI.

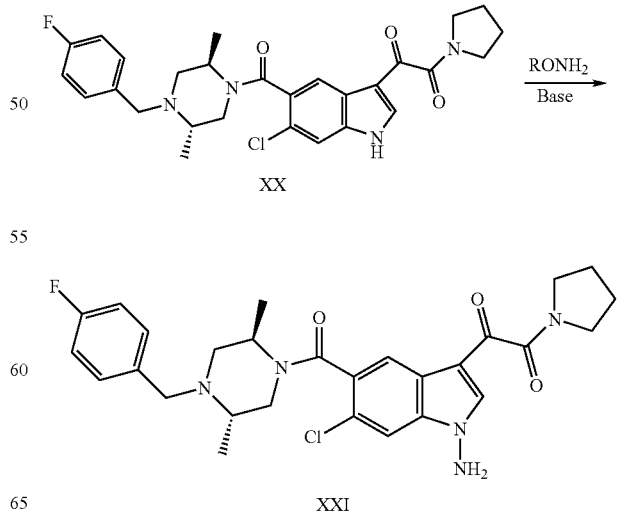

Examples of N-amination reactants RONH$_2$ include those where R is

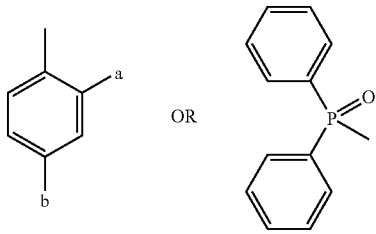

wherein a and b are CF$_3$, NO$_2$, CN or an other electron withdrawing group.

Assays for p38 α Kinase Inhibition

For each of the assay procedures described below, the TNF-α production correlates to the activity of p38-α kinase.

A. Human Whole Blood Assay for p$^{38}$ Kinase Inhibition

Venous blood is collected from healthy male volunteers into a heparinized syringe and is used within 2 hours of collection. Test compounds are dissolved in 100% DMSO and 1 μl aliquots of drug concentrations ranging from 0 to 1 mM are dispensed into quadruplicate wells of a 24-well microtiter plate (Nunclon Delta SI, Applied Scientific, So. San Francisco, Calif.). Whole blood is added at a volume of 1 ml/well and the mixture is incubated for 15 minutes with constant shaking (Titer Plate Shaker, Lab-Line Instruments, Inc., Melrose Park, Ill.) at a humidified atmosphere of 5% CO$_2$ at 37° C. Whole blood is cultured either undiluted or at a final dilution of 1:10 with RPMI 1640 (Gibco 31800+ NaHCO$_3$, Life Technologies, Rockville, Md. and Scios, Inc., Sunnyvale, Calif.). At the end of the incubation period, 10 μl of LPS (E. coli 0111:B4, Sigma Chemical Co., St. Louis, Mo.) is added to each well to a final concentration of 1 or 0.1 μg/ml for undiluted or 1:10 diluted whole blood, respectively. The incubation is continued for an additional 2 hours. The reaction is stopped by placing the microtiter plates in an ice bath and plasma or cell-free supernates are collected by centrifugation at 3000 rpm for 10 minutes at 4° C. The plasma samples are stored at −80° C. until assayed for TNF-α levels by ELISA, following the directions supplied by Quantikine Human TNF-α assay kit (R&D Systems, Minneapolis, Minn.).

IC$_{50}$ values are calculated using the concentration of inhibitor that causes a 50% decrease as compared to a control.

B. Enriched Mononuclear Cell Assay for p38 Kinase Inhibition

The enriched mononuclear cell assay, the protocol of which is set forth below, begins with cryopreserved Human Peripheral Blood Mononuclear Cells (HPBMCs) (Clonetics Corp.) that are rinsed and resuspended in a warm mixture of cell growth media. The resuspended cells are then counted and seeded at 1×10$^6$ cells/well in a 24-well microtitre plate. The plates are then placed in an incubator for an hour to allow the cells to settle in each well.

After the cells have settled, the media is aspirated and new media containing 100 ng/ml of the cytokine stimulatory factor Lipopolysaccharide (LPS) and a test chemical compound is added to each well of the microtiter plate. Thus, each well contains HPBMCs, LPS and a test chemical compound. The cells are then incubated for 2 hours, and the amount of the cytokine Tumor Necrosis Factor Alpha (TNF-α) is measured using an Enzyme Linked Immunoassay (ELISA). One such ELISA for detecting the levels of TNF-α is commercially available from R&D Systems. The amount of TNF-α production by the HPBMCs in each well is then compared to a control well to determine whether the chemical compound acts as an inhibitor of cytokine production.

LPS Induced Cytokine Synthesis in HPBMCs
Cryopreserved HPBMC (cat#CC-2702 Clonetics Corp)
LGM-3 media (cat#CC-3212 Clonetics Corp)
LPS stock 10 μg/ml (Cat. No. L 2630 serotype 0111:B4 Sigma)
Human TNF-α ELISA (R&D Systems)
DNase I (10 mg/ml stock)
Preparation of Cells.
LGM-3 media warmed to 37° C.
5 μl of DNase I stock added to 10 ml media.
Cells thawed rapidly and dispersed into above.
Centrifuge 200×g×10 min @ RT.
Pellet up in 10 ml sterile PBS.
Centrifuge 200×g×10 min @ RT.
Pellet resuspended in 10 ml LGM-3 then diluted to 50 ml with LGM-3.
Perform cell count.
Adjust to 1×E06 cells/well.
Seed 1 ml/well of a 24 well plate.
Place plate in incubator to plate down for 1 hour.
Preparation of Incubation Media.
LGM-3 containing 100 ng/ml LPS (e.g. 50 ml media plus 0.5 ml LPS stock)
Aliquot into 2 ml aliquots and add 1000× inhibitor dilutions.
Incubation When cells have plated down aspirate media away and overlay with 1 ml relevant incubation media. Return plate to incubator for 2 hours or 24 hours. Remove supernatants after incubation to a labeled tube and either perform TNF (or other) ELISA immediately or freeze for later assay.

IC$_{50}$ values are calculated using the concentration of inhibitor that causes a 50% decrease as compared to a control.

Administration and Use

The compounds of the invention are useful among other indications in treating conditions associated with inflammation. Thus, the compounds of formula (1) or their pharmaceutically acceptable salts are used in the manufacture of a medicament for prophylactic or therapeutic treatment of mammals, including humans, in respect of conditions characterized by excessive production of cytokines and/or inappropriate or unregulated cytokine activity on such cells as cardiomyocytes, cardiofibroblasts and macrophages.

The compounds of the invention inhibit the production of cytokines such as TNF, IL-1, IL-6 and IL-8, cytokines that are important proinflammatory constituents in many different disease states and syndromes. Thus, inhibition of these cytokines has benefit in controlling and mitigating many diseases. The compounds of the invention are shown herein to inhibit a member of the MAP kinase family variously called p38 MAPK (or p38), CSBP, or SAPK-2. The activation of this protein has been shown to accompany exacerbation of the diseases in response to stress caused, for example, by treatment with lipopolysaccharides or cytokines such as TNF and IL-1. Inhibition of p38 activity, therefore, is predictive of the ability of a medicament to provide a beneficial effect in treating diseases such as Alzheimer's, coronary artery disease, congestive heart failure, cardiomyopathy, myocarditis, vasculitis, restenosis, such as occurs following coronary angioplasty, atherosclerosis, IBD, rheumatoid arthritis, rheumatoid spondylitis, osteoarthritis, gouty arthritis and other arthritic conditions, multiple sclerosis, acute respiratory distress syndrome (ARDS), asthma, chronic obstructive pulmonary disease (COPD), silicosis, pulmonary sarcosis, sepsis, septic shock, endotoxic shock, Gram-negative sepsis, toxic shock syndrome, heart and brain failure (stroke) that are characterized by ischemia and reperfusion injury, surgical procedures, such as transplantation procedures and graft rejections, cardiopulmonary bypass, coronary artery bypass graft, CNS injuries, including open and closed head trauma, inflammatory eye conditions such as conjunctivitis and uveitis, acute renal failure, glomerulonephritis, inflammatory bowel diseases, such as Crohn's disease or ulcerative colitis, graft vs. host disease, bone resorption diseases like osteoporosis, type II diabetes, pyresis, psoriasis, cachexia, viral diseases such as those caused by HIV, CMV, and Herpes, and cerebral malaria.

Within the last several years, p38 has been shown to comprise a group of MAP kinases designated p38-α, p38-β, p38-γ and p38-δ. Jiang, Y., et al., *J Biol Chem* (1996) 271:17920-17926 reported characterization of p38-β as a 372-amino acid protein closely related to p38-α. In comparing the activity of p38-α with that of p38-β, the authors state that while both are activated by proinflammatory cytokines and environmental stress, p38-β was preferentially activated by MAP kinase kinase-6 (MKK6) and preferentially activated transcription factor 2, thus suggesting that separate mechanisms for action may be associated with these forms.

Kumar, S., et al., *Biochem Biophys Res Comm* (1997) 235: 533-538 and Stein, B., et al., *J Biol Chem* (1997) 272:19509-19517 reported a second isoform of p38-β, p38-β2, containing 364 amino acids with 73% identity to p38-α. All of these reports show evidence that p38-β is activated by proinflammatory cytokines and environmental stress, although the second reported p38-β isoform, p38-β2, appears to be preferentially expressed in the CNS, heart and skeletal muscle compared to the more ubiquitous tissue expression of p38-α. Furthermore, activated transcription factor-2 (ATF-2) was observed to be a better substrate for p38-β2 than for p38-α, thus suggesting that separate mechanisms of action may be associated with these forms. The physiological role of p38-β1 has been called into question by the latter two reports since it cannot be found in human tissue and does not exhibit appreciable kinase activity with the substrates of p38-α.

The identification of p38-γ was reported by Li, Z., et al., *Biochem Biophys Res Comm* (1996) 228:334-340 and of p38-δ by Wang, X., et al., *J Biol Chem* (1997) 272:23668-23674 and by Kumar, S., et al., *Biochem Biophys Res Comm* (1997) 235:533-538. The data suggest that these two p38 isoforms (γ and δ) represent a unique subset of the MAPK family based on their tissue expression patterns, substrate utilization, response to direct and indirect stimuli, and susceptibility to kinase inhibitors.

Thus, the invention encompasses the use of compounds which inhibit the activity of the p38-α for treating conditions associated with activation of p38-α, in particular those associated with cardiac hypertrophy, ischemia or other environmental stress such as oxidation injury, hyperosmolarity or other agents or factors that activate p38-α kinase, or cardiac failure, for example, congestive heart failure, cardiomyopathy and myocarditis.

The manner of administration and formulation of the compounds useful in the invention and their related compounds will depend on the nature of the condition, the severity of the condition, the particular subject to be treated, and the judgment of the practitioner; formulation will depend on mode of administration. As the compounds of the invention are small molecules, they are conveniently administered by oral administration by compounding them with suitable pharmaceutical excipients so as to provide tablets, capsules, syrups, and the like. Suitable formulations for oral administration may also include minor components such as buffers, flavoring agents and the like. Typically, the amount of active ingredient in the formulations will be in the range of 5%-95% of the total formulation, but wide variation is permitted depending on the carrier. Suitable carriers include sucrose, pectin, magnesium stearate, lactose, peanut oil, olive oil, water, and the like.

The compounds useful in the invention may also be administered through suppositories or other transmucosal vehicles. Typically, such formulations will include excipients that facilitate the passage of the compound through the mucosa such as pharmaceutically acceptable detergents.

The compounds may also be administered topically, for topical conditions such as psoriasis, or in formulation intended to penetrate the skin. These include lotions, creams, ointments and the like which can be formulated by known methods.

The compounds may also be administered by injection, including intravenous, intramuscular, subcutaneous or intraperitoneal injection. Typical formulations for such use are liquid formulations in isotonic vehicles such as Hank's solution or Ringer's solution.

Alternative formulations include nasal sprays, liposomal formulations, slow-release formulations, and the like, as are known in the art.

Any suitable formulation may be used. A compendium of art-known formulations is found in *Remington's Pharmaceutical Sciences,* latest edition, Mack Publishing Company, Easton, Pa. Reference to this manual is routine in the art.

The dosages of the compounds of the invention will depend on a number of factors which will vary from patient to patient. However, it is believed that generally, the daily oral dosage will utilize 0.001-100 mg/kg total body weight, preferably from 0.01-50 mg/kg and more preferably about 0.01 mg/kg-10 mg/kg. The dose regimen will vary, however, depending on the conditions being treated and the judgment of the practitioner.

It should be noted that the compounds of formula (1) can be administered as individual active ingredients, or as mixtures of several embodiments of this formula. In addition, the inhibitors of p38 kinase can be used as single therapeutic agents or in combination with other therapeutic agents. Drugs that could be usefully combined with these compounds include natural or synthetic corticosteroids, particularly prednisone and its derivatives, monoclonal antibodies targeting cells of the immune system, antibodies or soluble receptors or receptor fusion proteins targeting immune or non-immune cytokines, and small molecule inhibitors of cell division, protein synthesis, or mRNA transcription or translation, or inhibitors of immune cell differentiation or activation.

As implied above, although the compounds of the invention may be used in humans, they are also available for veterinary use in treating animal subjects.

The following examples are intended to illustrate but not to limit the invention, and to illustrate the use of the above Reaction Schemes.

EXAMPLE 1

Preparation of 2-{1-Amino-6-chloro-5-[4-(4-fluorobenzyl)-piperidine-1-carbonyl]-1H-indol-3-yl}-N,N-dimethyl-2-oxo-acetamide

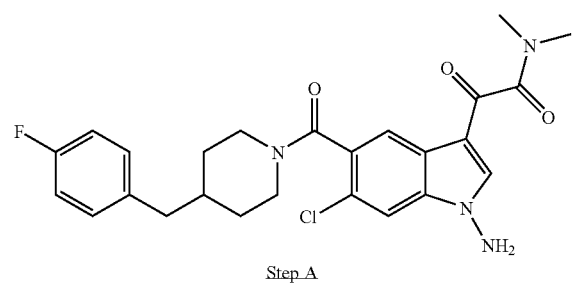

Step A

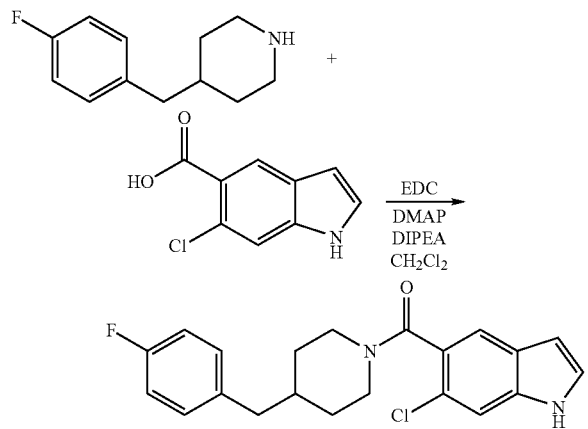

To the suspension of 6-chloroindole-5-carboxylic acid (8.5 g, 43.6 mmol) in anhydrous $CH_2Cl_2$ (500 mL) was added 4-fluorobenzylpiperidine hydrochloride salt (12 g, 52.3 mmol) and diisopropylethylamine (9 mL, 52.3 mmol). The mixture was stirred for 10 min and then EDC (10 g, 52.3 mmol) and DMAP (1.45 g, 11.9 mmol) were added. The reaction mixture became clear and was continually stirred for overnight. The reaction mixture was then treated with 10% HCl solution, and extracted with $CH_2Cl_2$. The combined organic extracts were washed with $NaHCO_3$ and brine then dried and concentrated. The residue was purified by chromatography on silica gel eluting with $CH_2Cl_2$:EtOAc (9:1) to give 13 g (81%) of the desired product as white foam. $M+H^+$ (371).

Step B

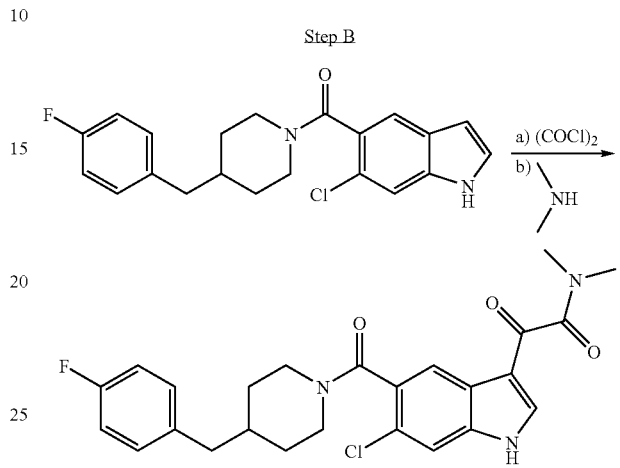

To the suspension of the indole (7.92 g, 21.5 mmol) was added oxalyl chloride (21.5 mL, 42.9 mmol, 2 M in $CH_2Cl_2$) dropwise at 0° C. The reaction mixture was stirred at 0° C. for 30 min, and then warmed up to RT and stirred for 5 h at which time a yellow suspension was formed. The solvent and excess oxalyl chloride were removed under the reduced pressure. The yellow solid was dried under vacuum and then dissolved in $CH_2Cl_2$ and placed at 0° C. Dimethylamine (43 mL, 85.9 mmol, 2 M in THF) was then added. After 30 min, the reaction mixture was treated with water and extracted with $CH_2Cl_2$. The organic extracts were washed with water, brine, dried and concentrated. The residue was purified by chromatography on silica gel eluting with 3% of MeOH in $CH_2Cl_2$ to give 8.7 g (87%) of the desired product as a white solid. $M+H^+$(470)

Step C

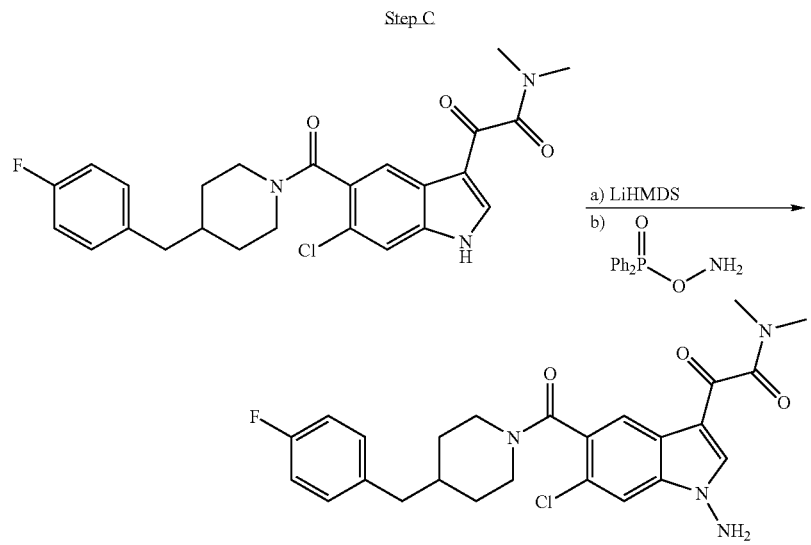

To a solution of the indole (500 mg, 1.07 mmol) in 1-methyl-2-pyrrolidinone (10 mL) was added lithium bis(trimethylsilyl)amide (1.6 mL, 1.6 mmol, 1.0 M in THF) at −10° C., followed by o-(diphenylphosphinyl)hydroxylamine (298 mg, 1.28 mmol). The reaction mixture was allowed to warm to RT and continually stirred for 6 h, then quenched with water (50 mL). The resulting mixture was extracted with EtOAc, washed with brine, dried (Na$_2$SO$_4$) and concentrated. The residue was purified by radial chromatography eluting with 75% EtOAc in hexane to give 420 mg (81%) of the desired product as a white solid. M+H$^+$(485).

EXAMPLE 2

Preparation of 2-{1-Amino-5-[4-(4-fluoro-benzyl)-piperidine-1-carbonyl]-6-methoxy-1H-indol-3-yl}-N,N-dimethyl-2-oxo-acetamide

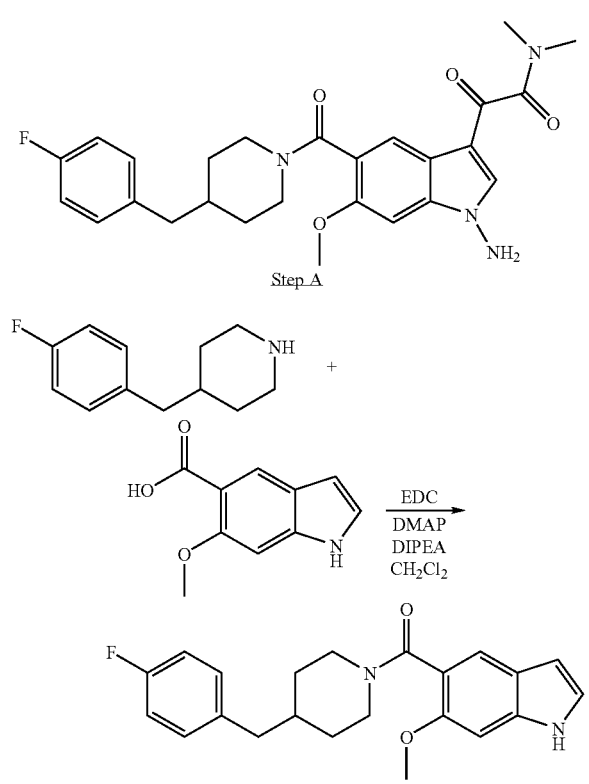

To the suspension of 6-methoxyindole-5-carboxylic acid (3.65 g, 19.1 mmol) in anhydrous CH$_2$Cl$_2$ (200 mL) was added 4-fluorobenzyl piperidine (6.14 g, 26.7 mmol) and diisopropylethylamine (4.64 mL, 26.7 mmol). The mixture was stirred for 10 min and EDC (4.37 g, 22.9 mmol) was added. The reaction mixture became clear and was continually stirred for overnight. Then the reaction mixture was treated with 10% of HCl solution, and extracted with CH$_2$Cl$_2$. The organic layer was washed with NaHCO$_3$, brine, dried and concentrated. The residue was taken up into CH$_2$Cl$_2$ and MeOH. The mixture was sonicated and a solid formed. Filtration and drying gave 6.32 g (90%) of the compound. M+H$^+$ (367).

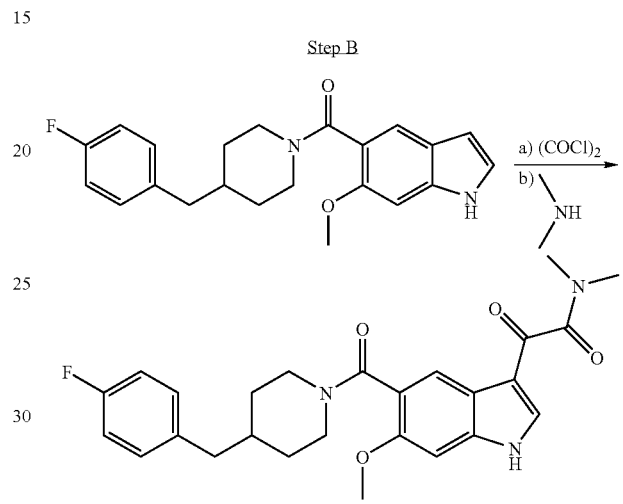

To the suspension of [4-(4-Fluoro-benzyl)-piperidin-1-yl]-(6-methoxy-1H-indol-5-yl)-methanone (2.5 g, 6.83 mmol) in was added oxalyl chloride (6.8 mL, 13.6 mmol, 2 M in CH$_2$Cl$_2$) in CH$_2$Cl$_2$ dropwise with ice bath cooling. The reaction mixture was stirred at 0° C. for 30 min, and warmed up to RT. and stirred for 5 h. The yellow suspension was formed during the reaction. The solvent and excess oxalyl chloride were removed. The yellow solid formed was dried under vacuum. The solid was redissolved in CH$_2$Cl$_2$ and cooled in ice bath. The mixture was quenched with dimethylamine (13.7 mL, 27.3 mmol, 40% in water). After 30 min, the reaction mixture was treated with water and extracted with CH$_2$Cl$_2$. The organic layer was washed with water and brine then dried and concentrated. The residue was purified by chromatography on silica gel to give 2.29 g (72%) of the desired product. M+H$^+$(466).

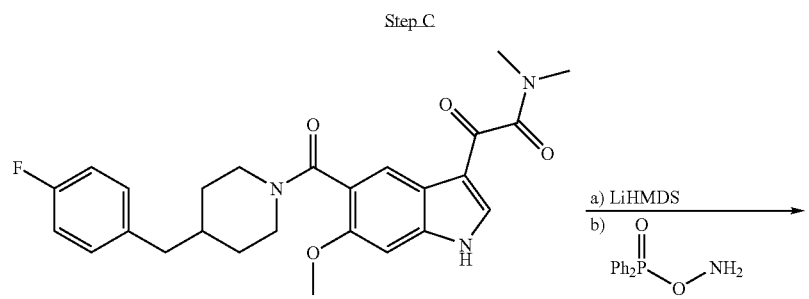

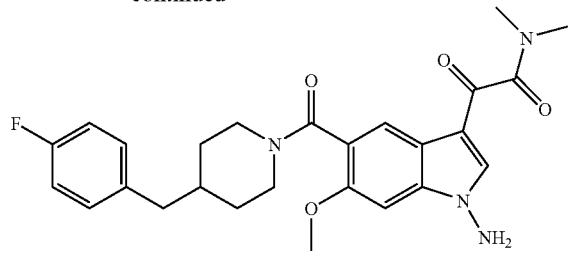

To a solution of 2-{5-[4-(4-Fluoro-benzyl)-piperidine-1-carbonyl]-6-methoxy-1H-indol-3-yl}-N,N-dimethyl-2-oxo-acetamide (620 mg, 1.33 mmol) in 1-methyl-2-pyrrolidinone (20 mL) was added lithium bis(trimethylsilyl)amide (2.1 mL, 2.1 mmol, 1.0 M in THF) at −10° C., followed by o-(diphenylphosphinyl)hydroxylamine (350 mg, 1.5 mmol). The reaction mixture was allowed to warm to RT and continually stirred for 6 h, then quenched with water (50 mL). The resulting mixture was extracted with EtOAc, washed with brine, dried ($Na_2SO_4$) and concentrated. The residue was purified by radial chromatography eluting with 2% MeOH in $CH_2Cl_2$ to give 300 mg (47%) of the desired product as a white solid. M+H$^+$(481).

EXAMPLE 3

Preparation of 1-{1-Amino-6-chloro-5-[4-(4-fluoro-benzyl)-2R,5S-dimethyl-piperazine-1-carbonyl]-1H-indol-3-yl}-2-pyrrolidin-1-yl-ethane-1,2-dione

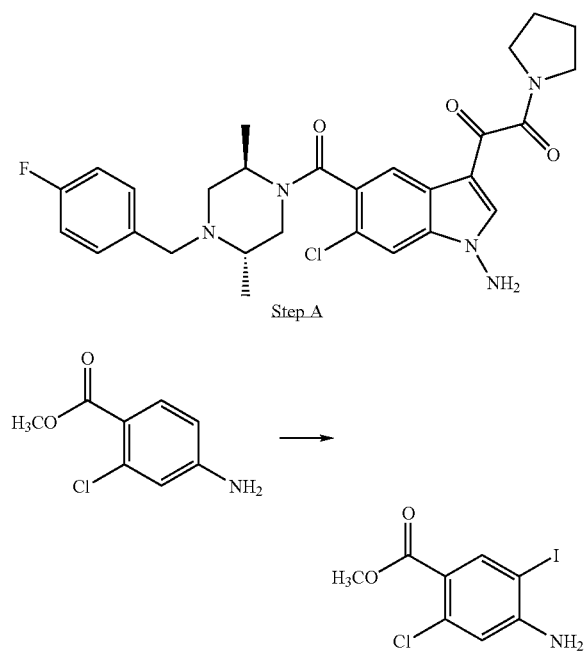

To a solution of methyl 2-chloro-4-aminobenzoate (109 g, 587 mmol) in 440 mL DMF was added $NaIO_4$ (50 g) and iodine (119 g). The mixture was warmed at 50° C. for 2 h. It was then cooled and diluted with water and filtered. The solid was treated with sodium hydrogensulfite (19 g) in water (110 mL) at 40° C. for 1 h. The mix was filtered again and washed with water, followed by isopropanol. Upon drying, the product was obtained in 56% yield. M+H$^+$(312).

Step B

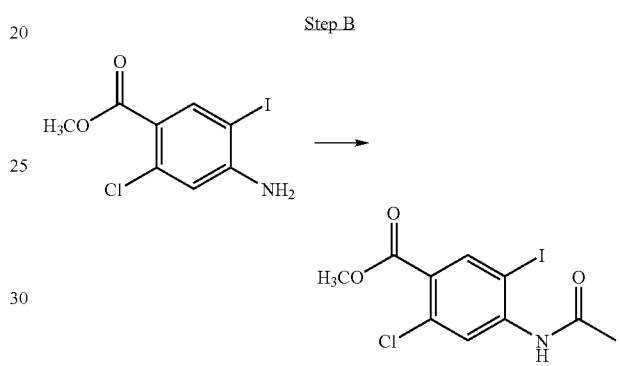

To a solution of 4-amino-5-iodo-2-chloro-benzoic acid methyl ester (104 g, 330 mmol) in 330 mL THF was added pyridine (40 mL). The solution was cooled to 0° C. and acetyl chloride (35 mL) was added slowly. Stirring was continued for 4 h. The mix was cooled and $H_2O$ (800 mL) was added dropwise. Filtered and washed with $H_2O$ followed by MeOH/$H_2O$ (1:1). Upon drying, the product was obtained in 81% yield. M+H$^+$(354).

Step C

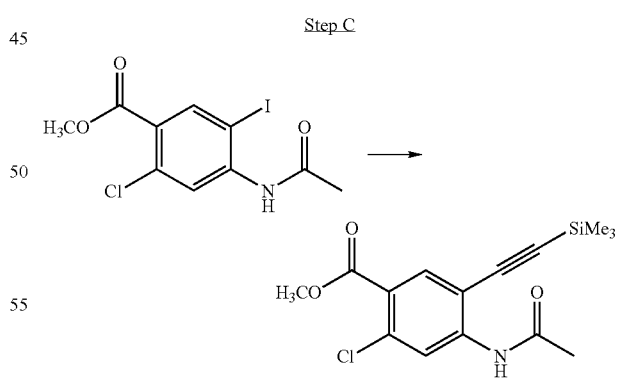

To a solution of compound 4-acetylamino-5-iodo-2-chloro-benzoic acid methyl ester (95 g, 269 mmol) in 51 mL $Et_3N$ and 290 mL $CH_2Cl_2$ was added CuI (0.50 g) and $(Ph_3P)_2PdCl_2$ (1.05 g). It was then cooled to 0° C. and trimethylsilylacetylene (30.0 g) was added slowly. The temperature was raised to RT and stirring continued for 12 h. The mixture was poured into EtOAc and washed with water and brine. The organic layer was dried with $Na_2SO_4$ and concentrated. The residue was purified by column chromatography using EtOAc and hexane to give the product. M+H$^+$(324).

Step D

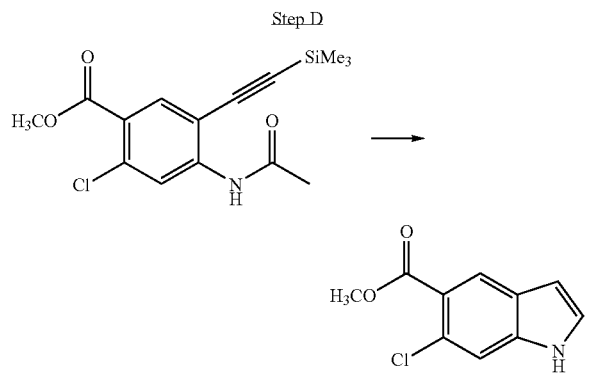

To a solution of 4-acetylamino-2-chloro-5-trimethylsilanylethynyl-benzoic acid methyl ester (10 g, 30.9 mmol) in 50 mL THF was added tetrabutylammonium fluoride (14.0 g) and the mix was refluxed for 4 h then extracted with MTBE and washed with water and brine. The organic layer was dried with Na$_2$SO$_4$ and concentrated. The residue was purified by column chromatography using EtOAc and hexane to give the product in 96% yield. M+H$^+$(210).

Step E

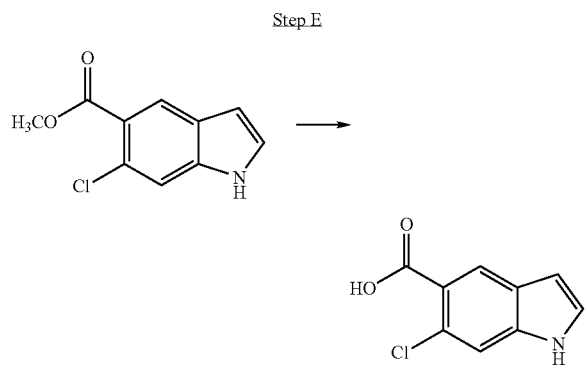

To a solution of 6-chloro-1H-indole-5-carboxylic acid methyl ester (6.0 g, 28.7 mmol) in 200 mL MeOH and 200 mL water was added NaOH (6.0 g) and the mix was heated at 50° C. for 4 h. The solution was cooled, diluted with water and acidified to pH 2-3 and extracted with EtOAc, washed with water and brine. The organic layer was dried with Na$_2$SO$_4$ and concentrated to give the desired product. M+H$^+$(196).

Step F

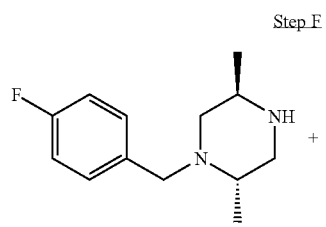

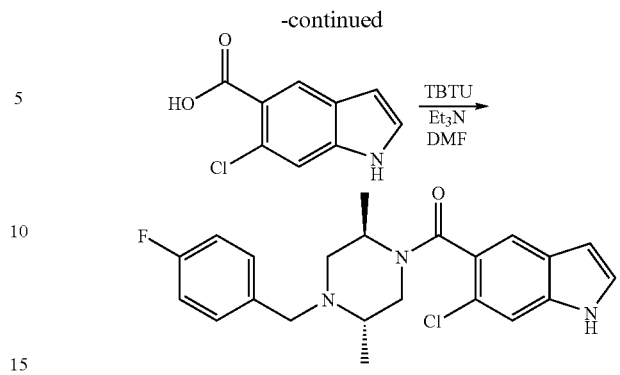

To a solution of 6-chloroindole-5-carboxylic acid (1.0 g, 5.11 mmol) and 4-fluorobenzyl-2S,5R-dimethylpiperazine (1.14 g, 5.11 mmol) in dimethylformamide (DMF) was added TBTU (1.64 g, 5.11 mmol) followed by triethylamine (1.55 g, 15.3 mmol). The reaction mixture was stirred overnight at rt. and then poured into ice water. The mixture was extracted with dichloromethane. The combined organic layer was washed with brine, dried and concentrated. The residue was purified by chromatography on silica gel eluting with EtOAc:hexane(2:3) to give 1.89 g (92%) of the desired product as a white solid. M+H$^+$(400).

Step G

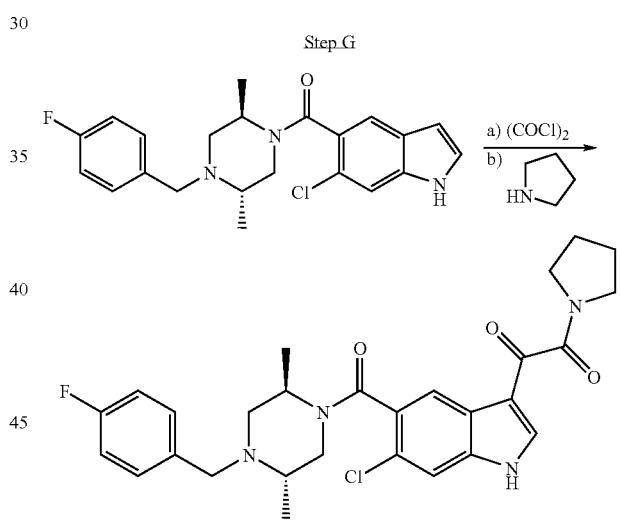

To a solution of (6-Chloro-1H-indol-5-yl)-[4-(4-fluorobenzyl)-2R,5S-dimethyl-piperazin-1-yl]-methanone (21 g, 53 mmol) in anhydrous CH$_2$Cl$_2$ (250 mL) was added oxalyl chloride (53 mL, 106 mmol, 2 M in CH$_2$Cl$_2$) dropwise with an ice bath cooling. The reaction mixture was stirred at 0° C. for 30 min, and warmed up to rt. and stirred for 5 h. A yellow suspension was formed during the reaction. The solvent and excess oxalyl chloride were removed. The yellow solid formed was dried under vacuum. The solid was redissolved in CH$_2$Cl$_2$ and cooled in ice bath. An excess amount of pyrrolidine (11.9 g, 160 mmol) was added to the reaction mixture. Stirred for 1 h, the reaction mixture was treated with water (200 mL). The organic layer was separated and washed with brine, dried and concentrated. The residue was purified by chromatography on silica gel eluting with CH$_2$Cl$_2$:MeOH (95:5) to give the desired product (19.8 g) in 71% yield as a white solid. M+H$^+$(526).

Step H (Method 1)

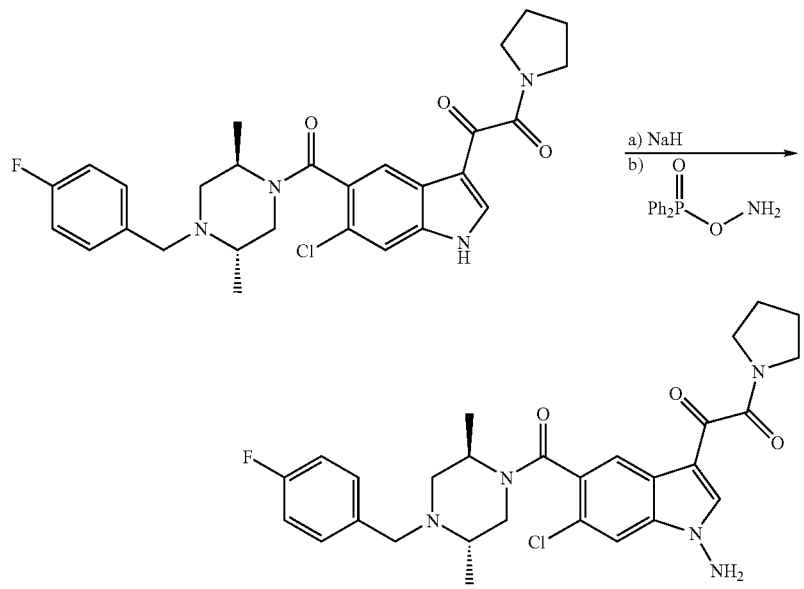

To a solution of indole 1-{6-Chloro-5-[4-(4-fluoro-benzyl)-2R,5S-dimethyl-piperazine-1-carbonyl]-1H-indol-3-yl}-2-pyrrolidin-1-yl-ethane-1,2-dione (2.4 g, 4.6 mmol) in anhydrous THF (50 mL) was added NaH (274 mg, 6.86 mmol, 60% dispersion in mineral oil) at rt. The resulting mixture was stirred for 30 min at RT. O-(diphenylphosphinyl) hydroxylamine (1.61 g, 6.86 mmol) was added and the reaction mixture was stirred for 10 h. The solvent was removed and the residue was treated with water (200 mL). The mixture was extracted with dichloromethane (30 mL×3). The combined organic layer was washed with brine, dried (Na$_2$SO$_4$) and concentrated. The residue was purified by chromatography on silica gel, eluting with 3% MeOH in CH$_2$Cl$_2$ to give 2.0 g (80%) of the desired product as a white solid. Sodium hydride can be replaced by lithium bis(trimethylsilyl)amide or potassium tert-butoxide, the same result is obtained. M+H$^+$ (541).

Step H (method 2)

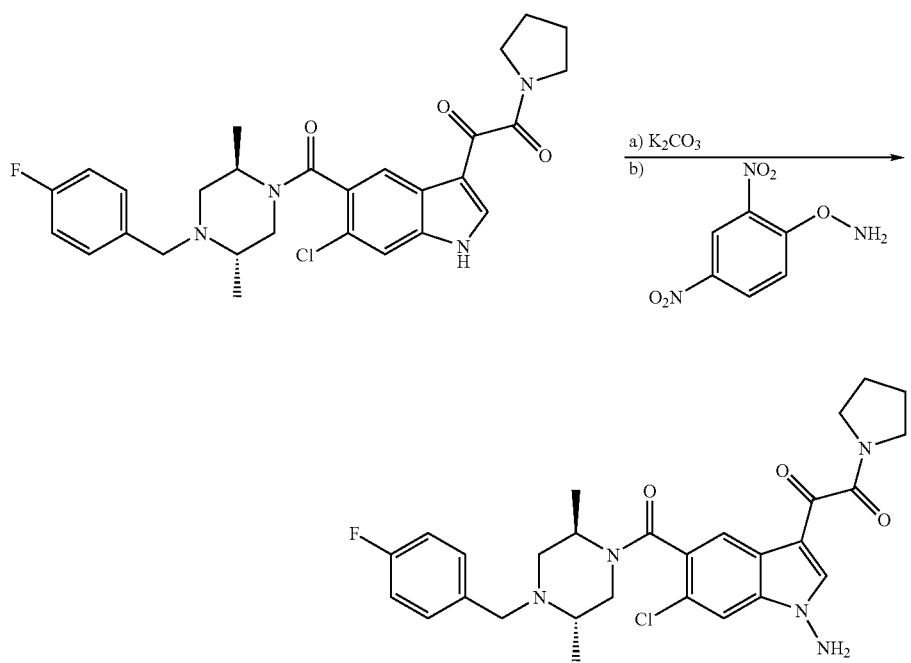

A suspension of indole 1-{6-Chloro-5-[4-(4-fluoro-benzyl)-2R,5S-dimethyl-piperazine-1-carbonyl]-1H-indol-3-yl}-2-pyrrolidin-1-yl-ethane-1,2-dione (2.4 g, 4.6 mmol) and fine powdered K$_2$CO$_3$ (1.9 g, 13.7 mmol) in DMF (22 mL) was stirred for 3 hours at RT. 2,4-Dinitrophenylhydroxyamine (1.2 g, 6 mmol) was added and the resulting mixture was stirred at rt. for 10 h. Then poured into water (200 mL), the mixture was extracted with dichloromethane (50 mL×4). The combined organic layer was dried (Na$_2$SO$_4$) and concentrated. The residue was purified by chromatography on silica gel eluting with 3% MeOH in CH$_2$Cl$_2$ to give 1.6 g (66%) of the desired product as a white solid. M+H$^+$(541).

EXAMPLE 4

2-{1-Amino-6-chloro-5-[4-(4-fluoro-benzyl)-2R,5S-dimethyl-piperazine-1-carbonyl]-1H-indol-3-yl}-N-methyl-2-oxo-acetamide Step A

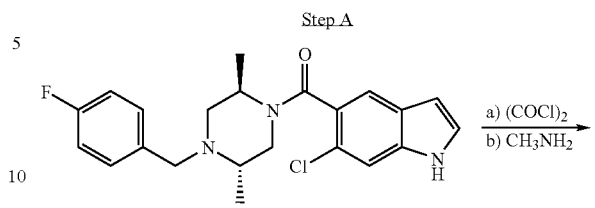

Step B

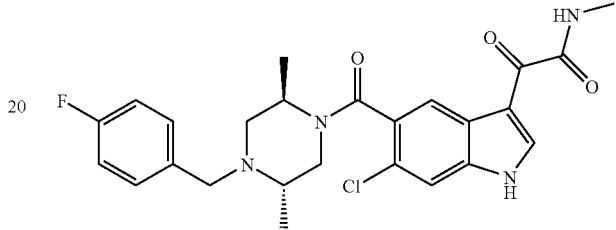

Prepared from (6-Chloro-1H-indol-5-yl)-[4-(4-fluorobenzyl)-2R,5S-dimethyl-piperazin-1-yl]-methanone as in Example 3, Step G using methylamine in place of pyrrolidine. M+H$^+$(485).

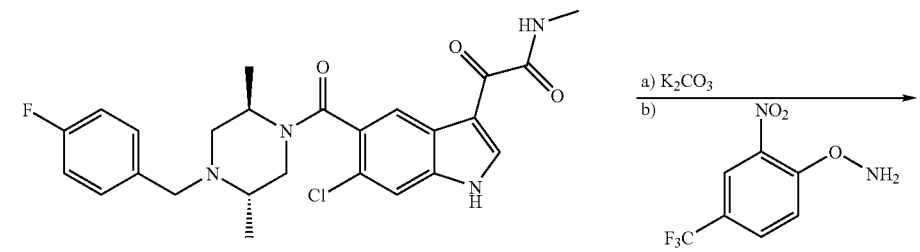

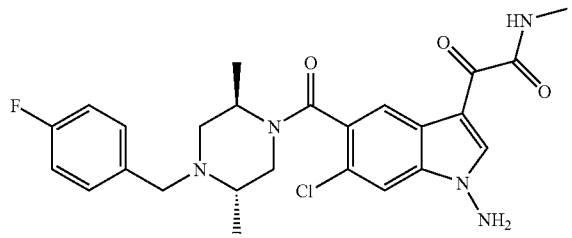

Prepared from 2-{6-Chloro-5-[4-(4-fluoro-benzyl)-2R,5S-dimethyl-piperazine-1-carbonyl]-1H-indol-3-yl}-N-methyl-2-oxo-acetamide as in Example 3, Step H, method 2 using O-(2-Nitro-4-trifluoromethyl-phenyl)-hydroxylamine as the aminating agent. M+H$^+$(500).

EXAMPLE 5

2-(1-Amino-6-chloro-5-{4-[4-(4-fluoro-benzyl)-2R,5S-dimethyl-piperazine-1-carbonyl]-1H-indol-3-yl}-2-oxo-acetamide

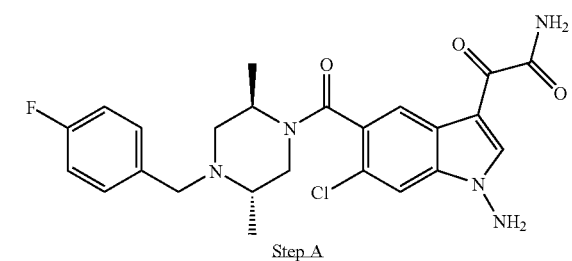

Step A

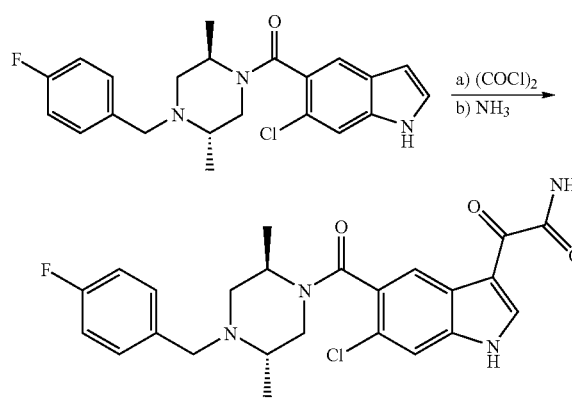

Prepared from (6-Chloro-1H-indol-5-yl)-{4-[4-(4-fluoro-benzyl)-2R,5S-dimethyl-piperazine-1-yl]-methanone as in Example 3, Step G using ammonia in dioxane in place of pyrrolidine. M+H$^+$(471).

Step B

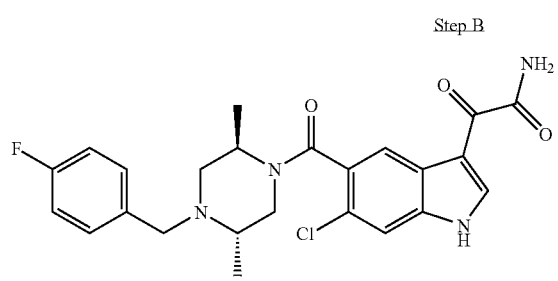

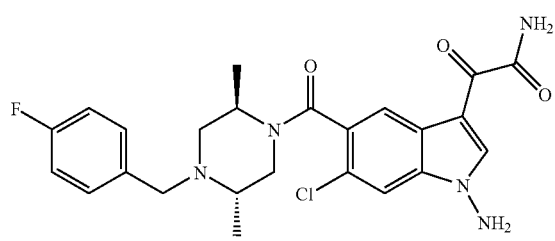

Prepared from 2-(6-Chloro-5-{4-[4-(4-fluoro-benzyl)-2R,5S-dimethyl-piperazine-1-carbonyl]-1H-indol-3-yl}-2-oxo-acetamide as in Example 3, Step H, method 2 using O-(2-Nitro-4-trifluoromethyl-phenyl)-hydroxylamine as the aminating agent. M+H$^+$(486).

EXAMPLE 6

Preparation of 2-{1-Amino-5-[4-(4-fluoro-benzyl)-2R,5S-dimethyl-piperazine-1-carbonyl]-6-methoxy-1H-indol-3-yl}-N,N-dimethyl-2-oxo-acetamide

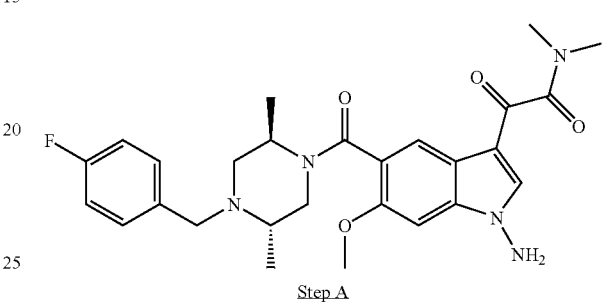

Step A

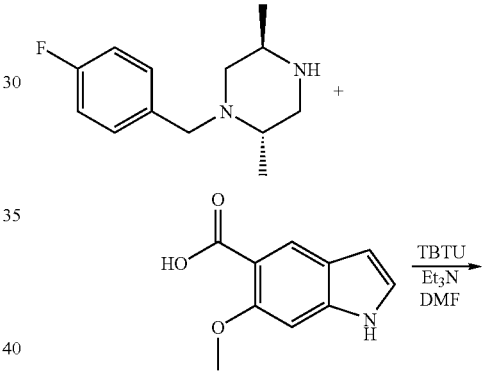

-continued

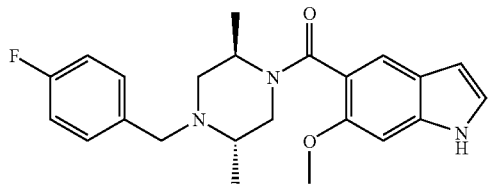

To a solution of 6-methoxyindole-5-carboxylic acid (1.0 g, 5.25 mmol) and 4-fluorobenzyl-2S,5R-dimethylpiperazine (1.2 g, 5.25 mmol) in dimethylforamide (DMF) was added TBTU (1.7 g, 5.25 mmol), followed by triethylamine (2.2 mL, 15.6 mmol). The reaction mixture was stirred overnight at RT and then poured into ice water. The mixture was extracted with dichloromethane. The combined organic layer was washed with brine, dried and concentrated. The residue was purified by chromatography on silica gel eluting with EtOAc:hexane(2:3) to give 1.3 g (63%) of the desired product as a white solid. M+H$^+$(396).

Step B

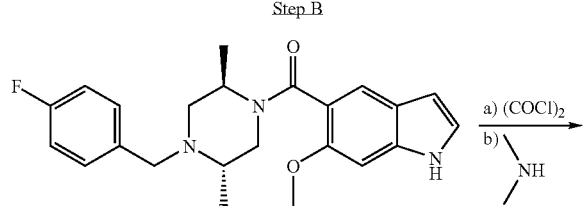

-continued

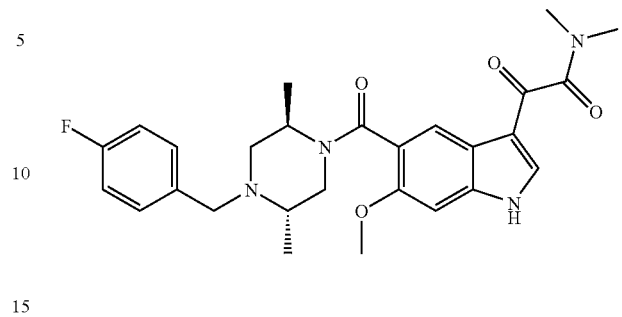

To a solution of [4-(4-Fluoro-benzyl)-2R,5S-dimethyl-piperazin-1-yl]-(6-methoxy-1H-indol-5-yl)-methanone (650 mg, 1.65 mmol) in anhydrous $CH_2Cl_2$ (15 mL) was added oxaly chloride (2.5 mL, 5 mmol, 2 M in $CH_2Cl_2$) dropwise with an ice bath cooling. The reaction mixture was stirred at 0° C. for 30 min, and warmed up to RT and stirred for 5 h. A yellow suspension was formed during the reaction. The solvent and excess oxalyl chloride were removed. The yellow solid formed was dried under vacuum. The solid was redissolved in $CH_2Cl_2$ and cooled in ice bath. An excess amount of dimethylamine (5 mL, 10 mmol, 2 M in THF) was added to the reaction mixture. Stirred for 1 h, the reaction mixture was treated with water (20 mL). The organic layer was separated and washed with brine, dried and concentrated. The residue was purified by chromatography on silica gel eluting with $CH_2Cl_2$:MeOH (95:5) to give the desired product (760 mg) in 93% yield as a white solid. M+H$^+$(495).

Step C

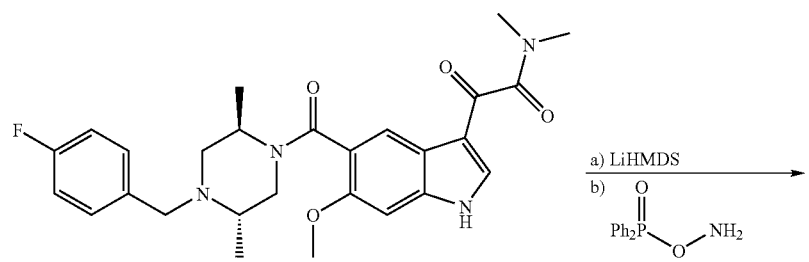

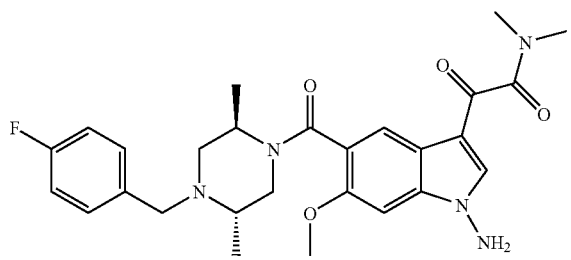

To a solution of indole 2-{5-[4-(4-Fluoro-benzyl)-2R,5S-dimethyl-piperazine-1-carbonyl]-6-methoxy-1H-indol-3-yl}-N,N-dimethyl-2-oxo-acetamide (500 mg, 1 mmol) in DMF (10 mL) was added lithium bis(trimethylsilyl)amide (3 mL, 3 mmol, 1.0 M in THF) at 0° C. The reaction mixture was stirred for 1 h, and then o-(diphenylphosphinyl)hydroxylamine (700 mg, 3 mmol) was added. The reaction mixture was allowed to warm to RT and continually stirred for 6 h, then quenched with water (50 mL). The resulting mixture was extracted with EtOAc, washed with brine, dried ($Na_2SO_4$) and concentrated. The residue was purified by radial chromatography eluting with 3% MeOH in $CH_2Cl_2$ to give 360 mg (47%) of the desired product as a white solid. M+H$^+$(510).

EXAMPLE 7

1-{1-Amino-5-[4-(4-fluoro-benzyl)-2R,5S-dimethyl-piperazine-1-carbonyl]-6-methoxy-1H-indol-3-yl}-2-pyrrolidin-1-yl-ethane-1,2-dione

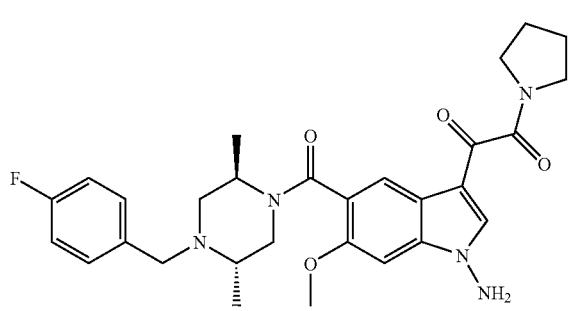

Step A

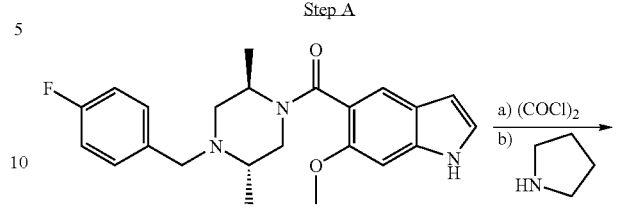

Prepared from [4-(4-fluoro-benzyl)-2R,5S-dimethyl-piperazin-1-yl]-(6-methoxy-1H-indol-5-yl)-methanone as in Example 3, Step G. M+H$^+$(521).

Step B

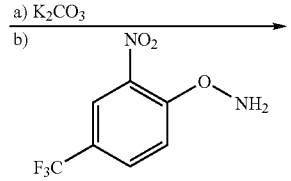

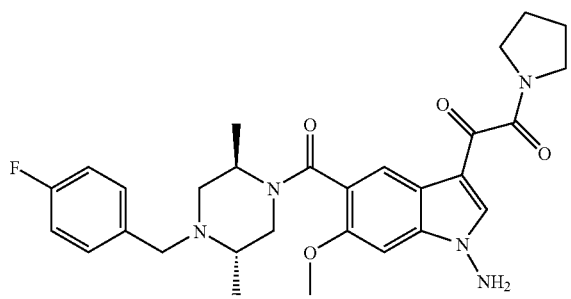

Prepared from 1-{5-[4-(4-fluoro-benzyl)-2R,5S-dimethyl-piperazine-1-carbonyl]-6-methoxy-1H-indol-3-yl}-2-pyrrolidin-1-yl-ethane-1,2-dione as in Example 3, Step H, method 2 using O-(2-Nitro-4-trifluoromethyl-phenyl)-hydroxylamine as the aminating agent. M+H⁺(536).

EXAMPLE 8

2-{1-Amino-5-[4-(4-fluoro-benzyl)-2R,5S-dimethyl-piperazine-1-carbonyl]-6-methoxy-1H-indol-3-yl}-N-methyl-2-oxo-acetamide

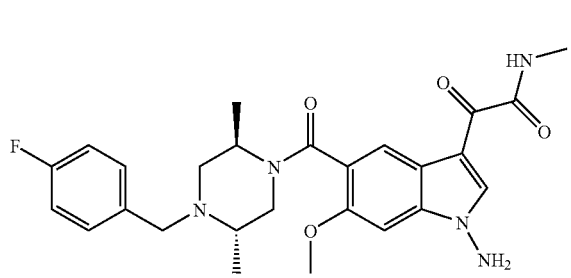

Step A

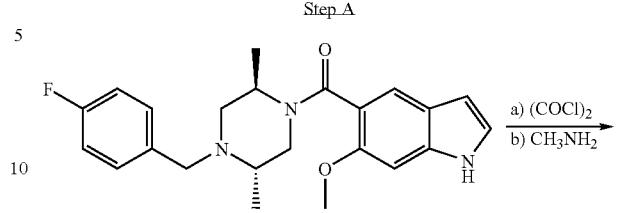

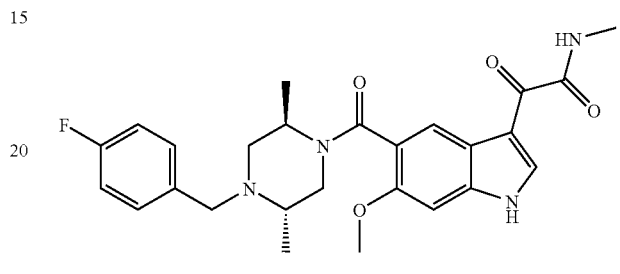

Prepared from [4-(4-fluoro-benzyl)-2R,5S-dimethyl-piperazin-1-yl]-(6-methoxy-1H-indol-5-yl)-methanone as in Example 3, Step G using methylamine in place of pyrrolidine. M+H⁺(481).

Step B

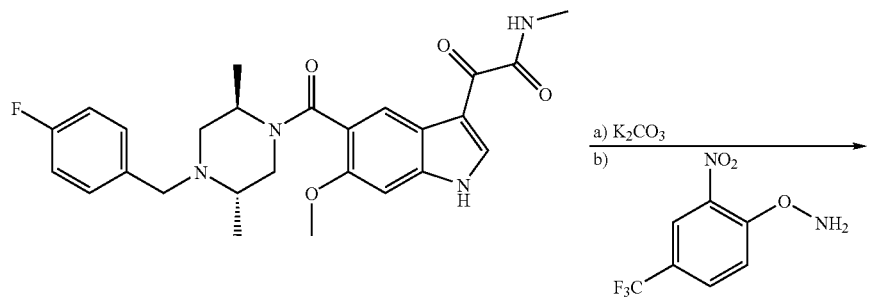

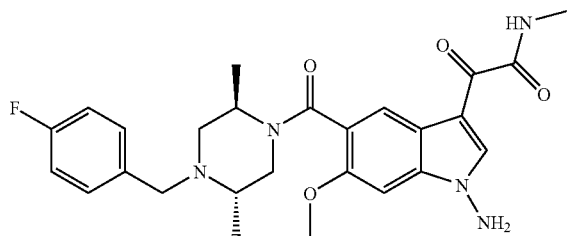

Prepared from 2-{5-[4-(4-Fluoro-benzyl)-2R,5S-dimethyl-piperazine-1-carbonyl]-6-methoxy-1H-indol-3-yl}-N-methyl-2-oxo-acetamide as in Example 3, Step H, method 2 using O-(2-Nitro-4-trifluoromethyl-phenyl)-hydroxylamine as the aminating agent. M+H$^+$(496).

EXAMPLE 9

Preparation of 1-{1-Amino-5-[4-(4-fluoro-benzyl)-piperidine-1-carbonyl]-6-methoxy-1H-indol-3-yl}-2-pyrrolidin-1-yl-ethane-1,2-dione -continued Step A

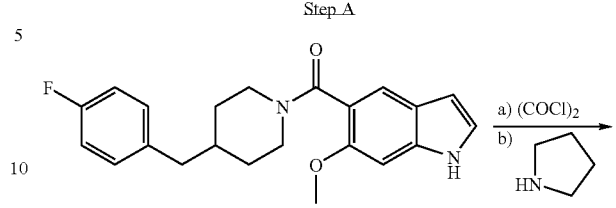

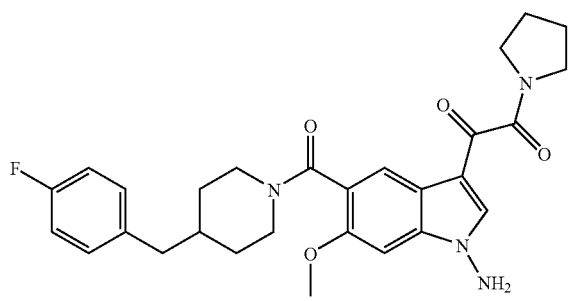

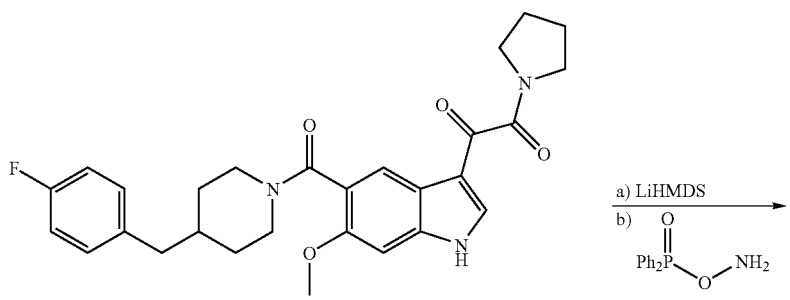

Prepared from [4-(4-Fluoro-benzyl)-piperidin-1-yl]-(6-methoxy-1H-indol-5-yl)-methanone as in Example 2, Step B using pyrrolidine in place of dimethylamine in 68% yield. M+H$^+$ (491).

Step B

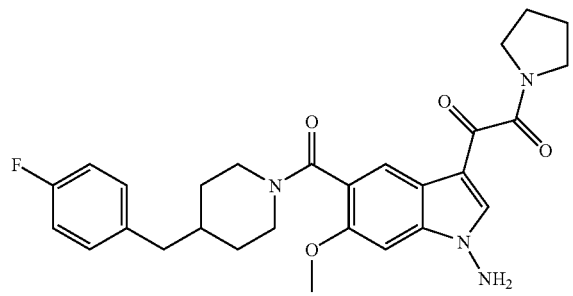

Prepared from 1-{5-[4-(4-Fluoro-benzyl)-piperidine-1-carbonyl]-6-methoxy-1H-indol-3-yl}-2-pyrrolidin-1-yl-ethane-1,2-dione as in Example 2, Step C in 48% yield. M+H$^+$ (507).

EXAMPLE 10

Preparation of 1-{1-Amino-5-[4-(4-fluoro-benzyl)-piperidine-1-carbonyl]-6-methoxy-1H-indol-3-yl}-2-(3-hydroxy-pyrrolidin-1-yl)-ethane-1,2-dione

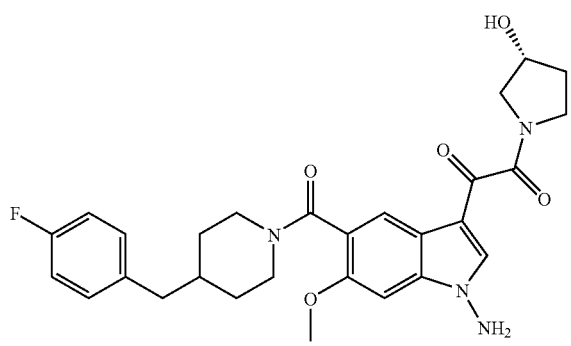

-continued
Step A

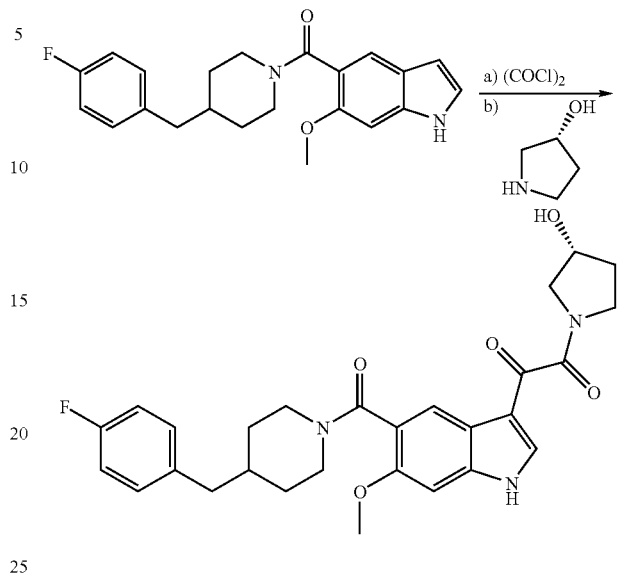

Prepared from [4-(4-Fluoro-benzyl)-piperidin-1-yl]-(6-methoxy-1H-indol-5-yl)-methanone as in Example 2, Step B using R-(+)-3-hydroxypyrrolidine in place of dimethylamine in 67% yield. M+H$^+$ (508).

Step B

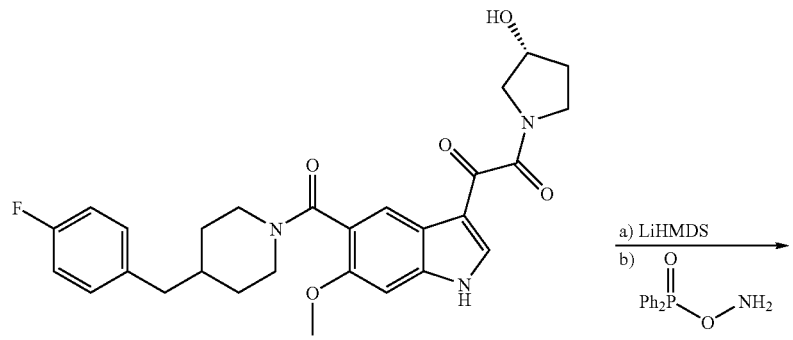

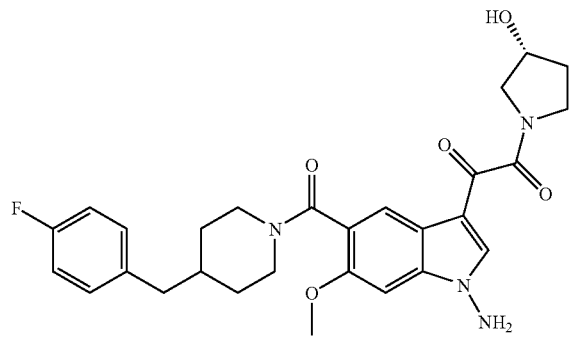

Prepared from 1-{5-[4-(4-Fluoro-benzyl)-piperidine-1-carbonyl]-6-methoxy-1H-indol-3-yl}-2-(3-hydroxy-pyrrolidin-1-yl)-ethane-1,2-dione as in Example 2, Step C in 32% yield. M+H⁺ (523).

EXAMPLE 11

Preparation of 1-{1-Amino-6-chloro-5-[4-(4-fluoro-benzyl)-2R,5S-dimethyl-piperazine-1-carbonyl]-1H-indol-3-yl}-2-(S-(−)-3-hydroxy-pyrrolidin-1-yl)-ethane-1,2-dione

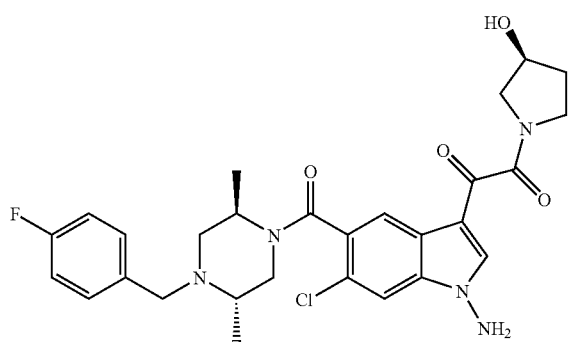

-continued
Step A

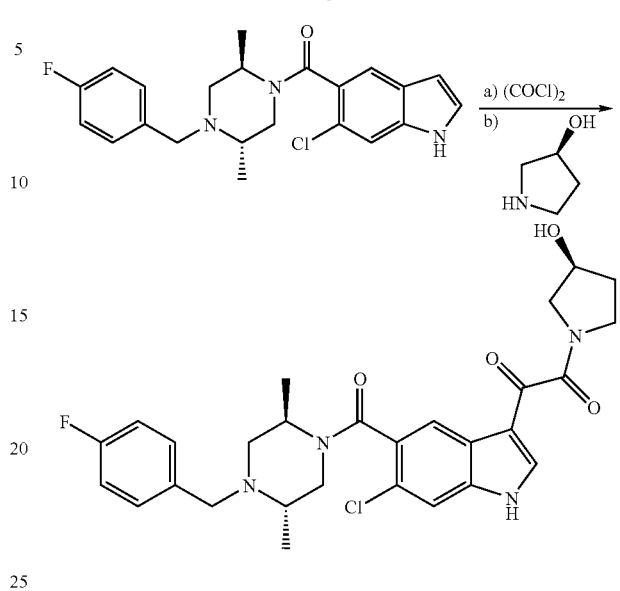

Prepared from (6-Chloro-1H-indol-5-yl)-[4-(4-fluoro-benzyl)-2R,5S-dimethyl-piperazin-1-yl]-methanone as in Example 3, Step G using S-(−)-3-hydroxypyrrolidine in place of pyrrolidine in 68% yield. M+H⁺ (542).

Step B

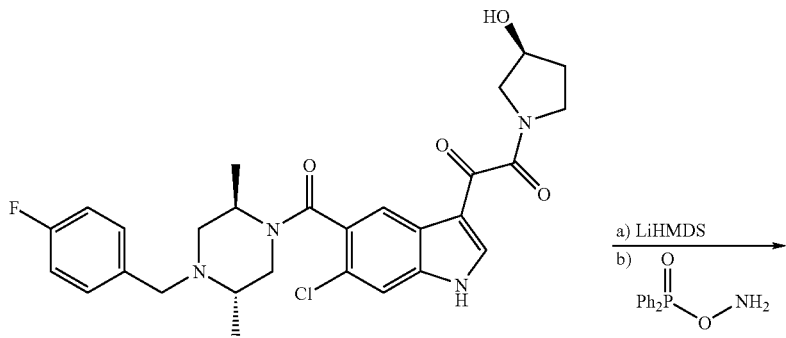

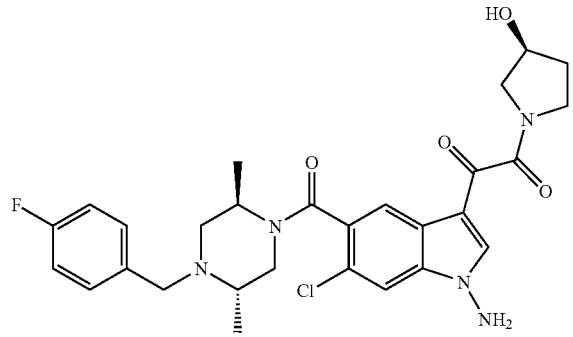

Prepared from 1-{6-Chloro-5-[4-(4-fluoro-benzyl)-2R,5S-dimethyl-piperazine-1-carbonyl]-1H-indol-3-yl}-2-(S-(−)-3-hydroxy-pyrrolidin-1-yl)-ethane-1,2-dione as in Example 2, Step C in 73% yield. M+H⁺ (557).

EXAMPLE 12

Preparation of 1-{1-Amino-6-chloro-5-[4-(4-fluoro-benzyl)-2R,5S-dimethyl-piperazine-1-carbonyl]-1H-indol-3-yl}-2-(R-(+)-3-hydroxy-pyrrolidin-1-yl)-ethane-1,2-dione

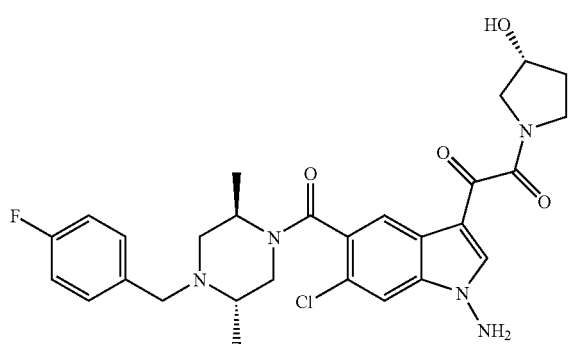

-continued
Step A

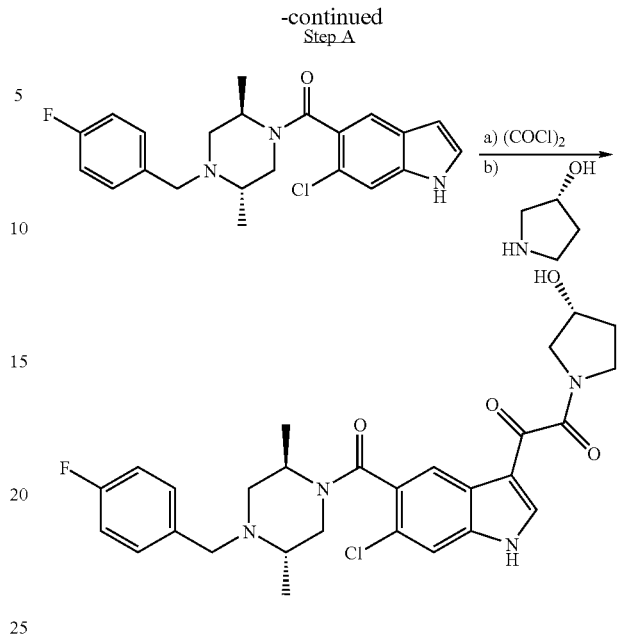

Prepared from (6-Chloro-1H-indol-5-yl)-[4-(4-fluoro-benzyl)-2R,5S-dimethyl-piperazin-1-yl]-methanone as in Example 3, Step G using R-(+)-3-hydroxypyrrolidine in place of pyrrolidine in 62% yield. M+H⁺ (542).

Step B

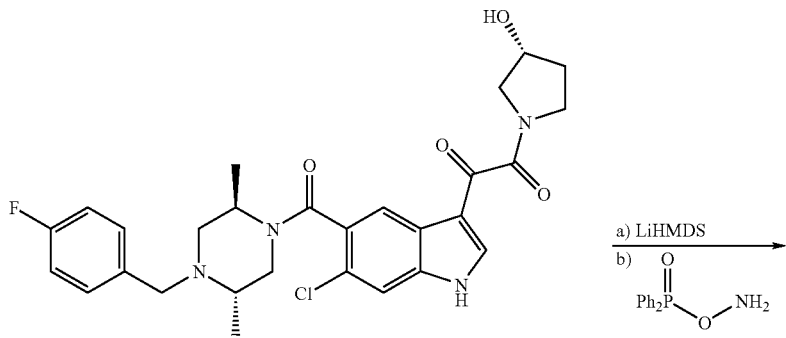

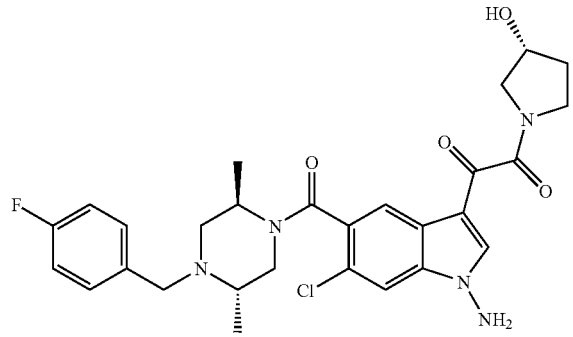

Prepared from 1-{6-Chloro-5-[4-(4-fluoro-benzyl)-2R,5S-dimethyl-piperazine-1-carbonyl]-1H-indol-3-yl}-2-(R-(+)-3-hydroxy-pyrrolidin-1-yl)-ethane-1,2-dione as in Example 2, Step C in 6% yield. M+H⁺ (557).

EXAMPLE 13

2-{1-Amino-6-chloro-5-[4-(4-fluoro-benzyl)-2R,5S-dimethyl-piperazine-1-carbonyl]-1H-indol-3-yl}-N,N-dimethyl-2-oxo-acetamide

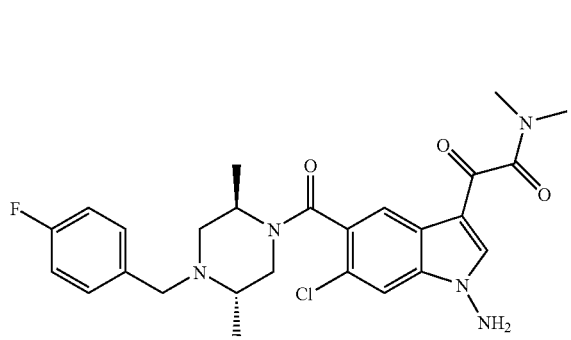

Step A

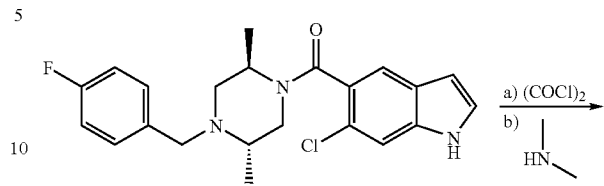

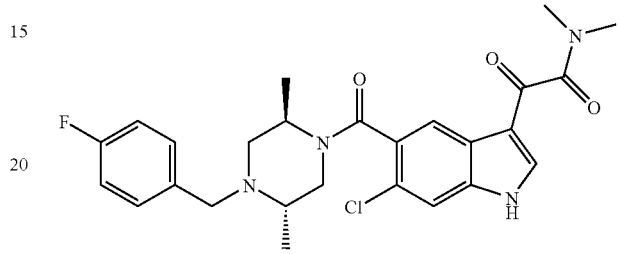

Prepared from (6-Chloro-1H-indol-5-yl)-[4-(4-fluoro-benzyl)-2R,5S-dimethyl-piperazin-1-yl]-methanone as in Example 3, Step G using dimethylamine in place of pyrrolidine. M+H⁺ (499).

Step B

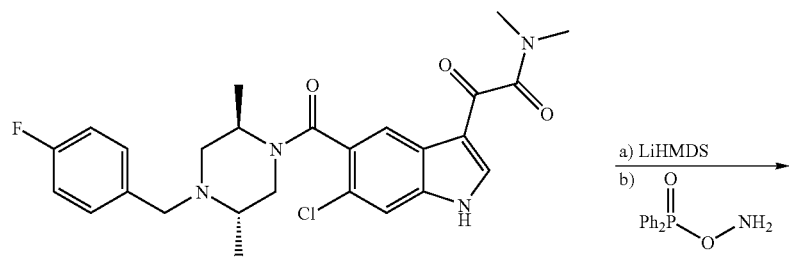

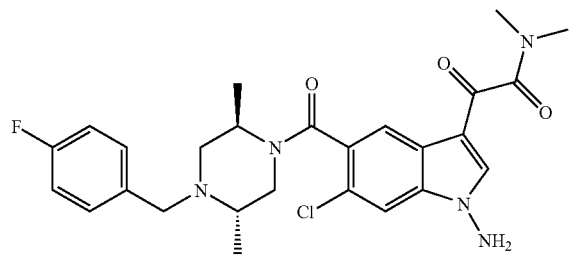

Prepared from 2-{6-Chloro-5-[4-(4-fluoro-benzyl)-2R,5S-dimethyl-piperazine-1-carbonyl]-1H-indol-3-yl}-N,N-dimethyl-2-oxo-acetamide as in Example 2, Step C. M+H+ (514).

EXAMPLE 14

2-{6-Chloro-1-dimethylamino-5-[4-(4-fluoro-benzyl)-2R,5S-dimethyl-piperazine-1-carbonyl]-1H-indol-3-yl}-N,N-dimethyl-2-oxo-acetamide Prepared as in Example 2, Step C using o-(diphenylphosphinyl)hydroxyldimethylamine. The residue was purified by radial chromatography to give 160 mg (29%) of the desired product. M+H+ (443).

Prepared from (6-Chloro-1-dimethylamino-1H-indol-5-yl)-[4-(4-fluoro-benzyl)-2R,5S-dimethyl-piperazin-1-yl]-methanone as in Example 3, Step G. The crude was purified by radial chromatography with 3-5% of MeOH in CHCl₃ to give 30 mg (9.2%) of the desired product. M+H+ (542).

EXAMPLE 15

Preparation of 1-{6-Chloro-1-dimethylamino-5-[4-(4-fluoro-benzyl)-2R,5S-dimethyl-piperazine-1-carbonyl]-1H-indol-3-yl}-2-(3-hydroxy-pyrrolidin-1-yl)-ethane-1,2-dione

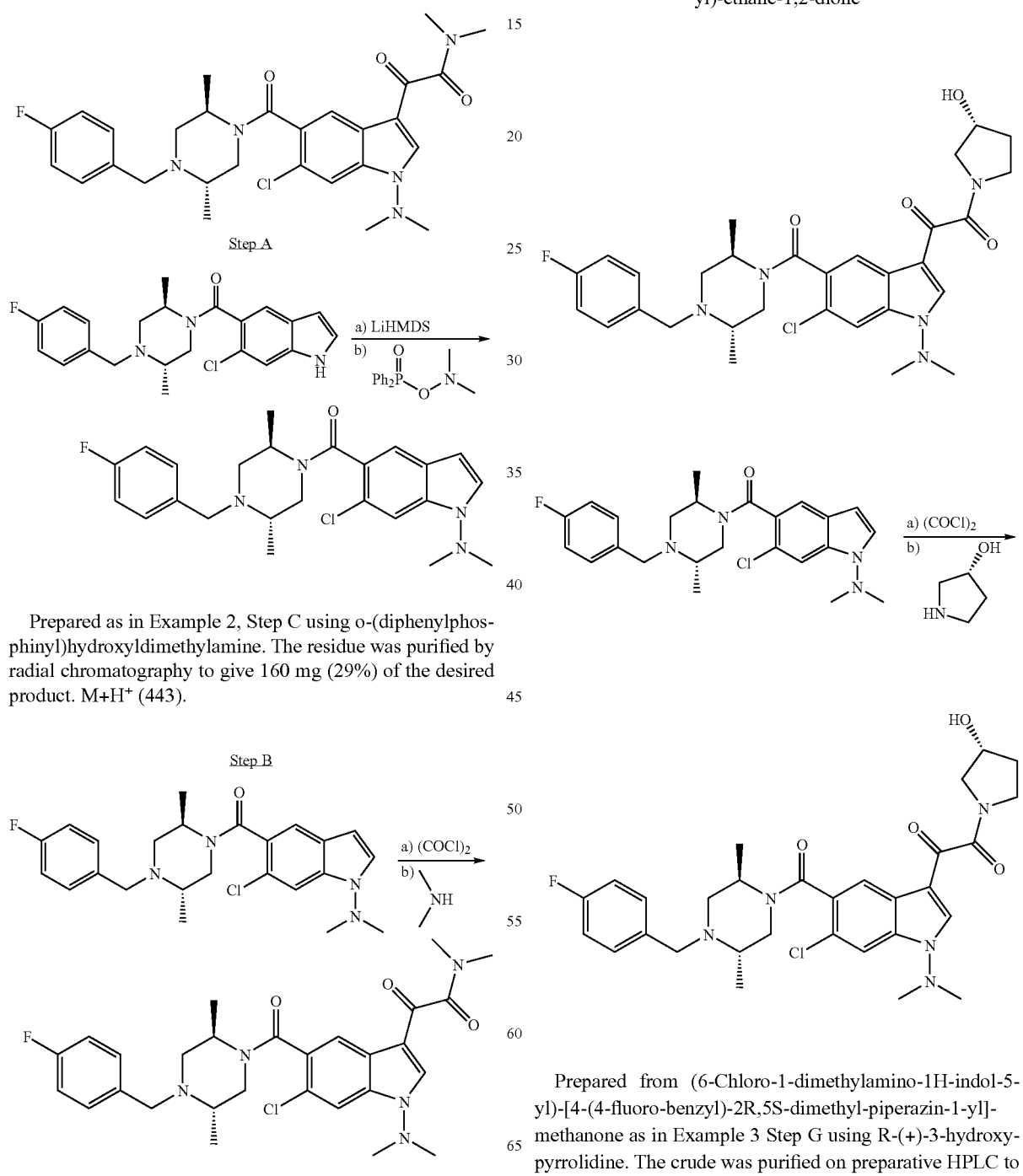

Prepared from (6-Chloro-1-dimethylamino-1H-indol-5-yl)-[4-(4-fluoro-benzyl)-2R,5S-dimethyl-piperazin-1-yl]-methanone as in Example 3 Step G using R-(+)-3-hydroxy-pyrrolidine. The crude was purified on preparative HPLC to give 3.4 mg (1.7%) of the desired product. M+H+ (584).

EXAMPLE 16

Preparation of {1-Amino-6-chloro-5-[4-(4-fluoro-benzyl)-2R,5S-dimethyl-piperazine-1-carbonyl]-1H-indol-3-yl}-oxo-acetic acid methyl ester

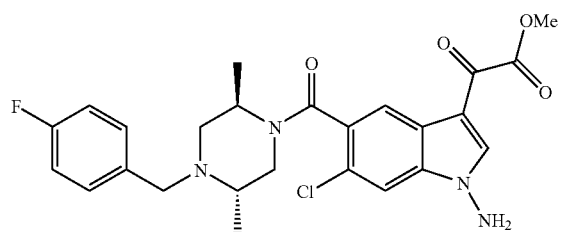

Step A

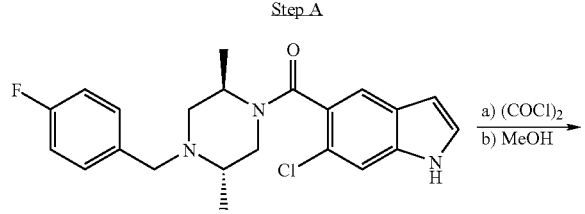

Prepared from (6-Chloro-1H-indol-5-yl)-[4-(4-fluoro-benzyl)-2R,5S-dimethyl-piperazin-1-yl]-methanone as in Example 2, Step B using methanol in place of dimethylamine.

Step B

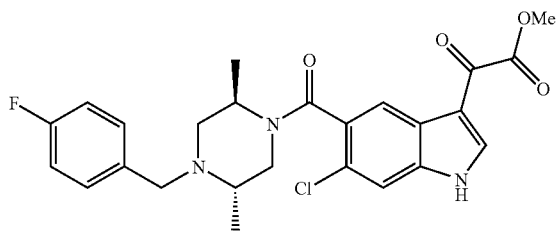

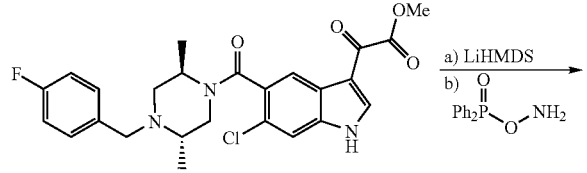

Prepared from {6-Chloro-5-[4-(4-fluoro-benzyl)-2R,5S-dimethyl-piperazine-1-carbonyl]-1H-indol-3-yl}-oxo-acetic acid methyl ester as in Example 2, Step C. The crude material was purified by radial chromatography with 5% MeOH in CHCl₃ first, then re-purified on silica gel column with 1% MeOH in CHCl₃ to give 17 mg (5.2%) of the desired product. M+H⁺ (501).

EXAMPLE 17

1-{1-Amino-5-[4-(4-fluoro-benzyl)-2R,5S-dimethyl-piperazine-1-carbonyl]-6-ethoxy-1H-indol-3-yl}-2-pyrrolidin-1-yl-ethane-1,2-dione

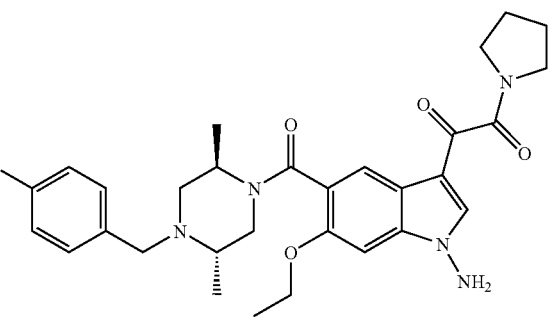

Step A

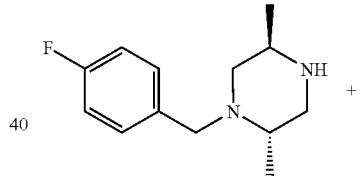

+

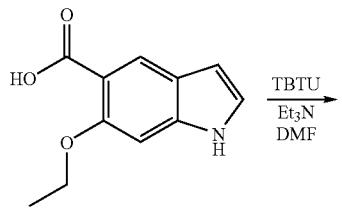

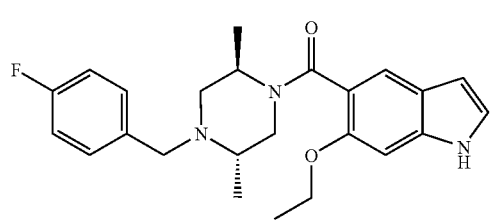

Prepared from 6-Ethoxy-1H-indole-5-carboxylic acid as in Example 3, Step F. M+H⁺(410).

Prepared from 1-{5-[4-(2-Chloro-benzyl)-2R,5S-dimethyl-piperazine-1-carbonyl]-6-ethoxy-1H-indol-3-yl}-2-pyrrolidin-1-yl-ethane-1,2-dione as in Example 3, Step H, method 2 (74% yield). M+H⁺(550).

EXAMPLE 18

1-{1-Amino-5-[4-(3-chloro-benzyl)-2R,5S-dimethyl-piperazine-1-carbonyl]-6-ethoxy-1H-indol-3-yl}-2-pyrrolidin-1-yl-ethane-1,2-dione Step B

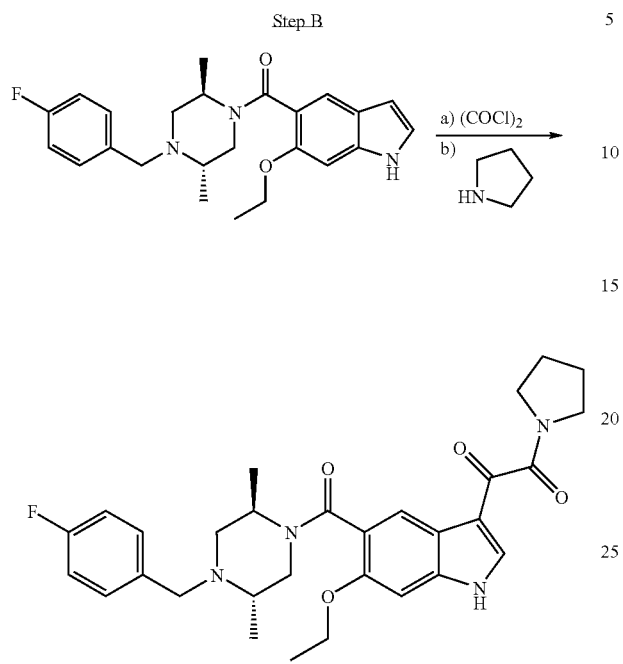

Prepared from [4-(4-fluoro-benzyl)-2R,5S-dimethyl-piperazin-1-yl]-(6-ethoxy-1H-indol-5-yl)-methanone as in Example 3, Step G (51% yield). M+H⁺(535).

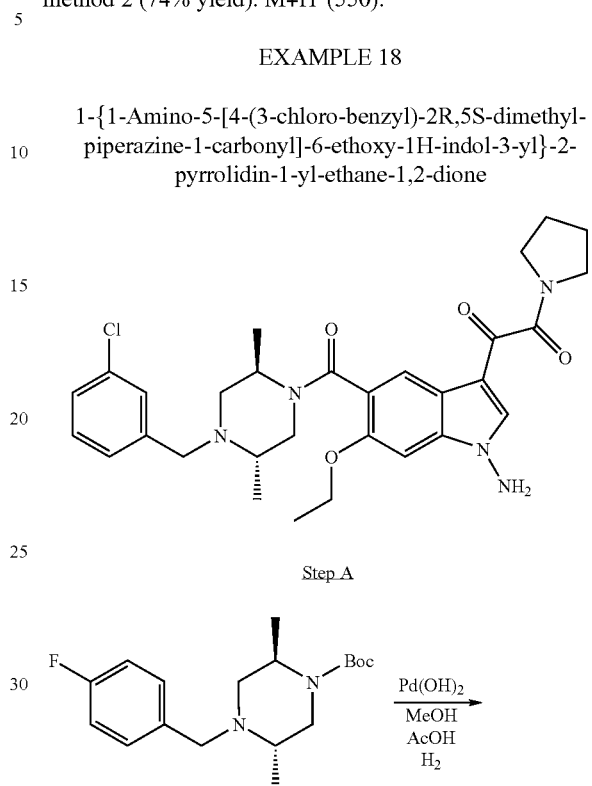

Step C

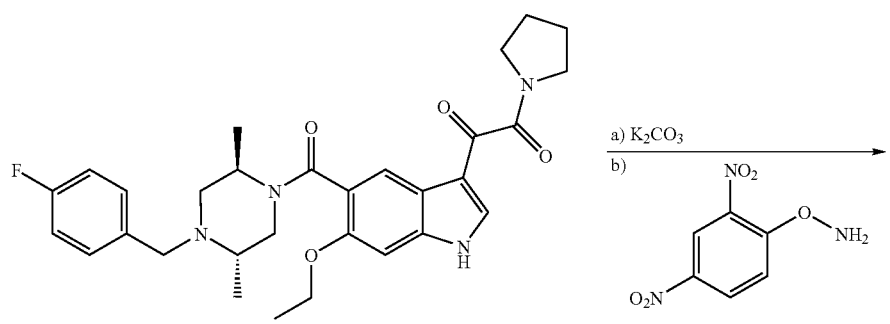

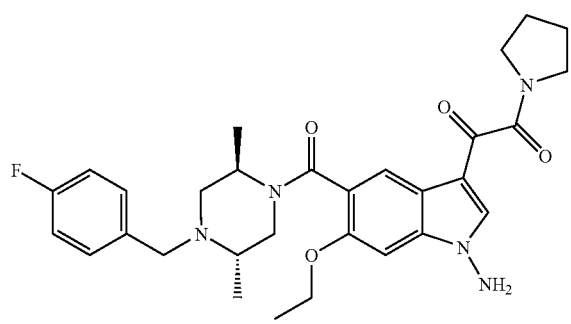

-continued

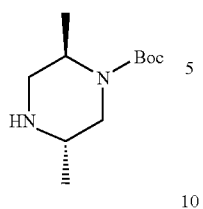

A solution of 4-(4-Fluoro-benzyl)-2R,5S-dimethyl-piperazine-1-carboxylic acid tert-butyl ester (37.8 g, 117.4 mmol) in MeOH (250 mL) and glacial aceticic acid ( 30 mL) was stirred and purged with $N_2$ for 10 min in a 2-L hydrogenation flask. To the mixture was added palladium hydroxide (3.8 g, 20 wt. %) and it was shaking for 48 h at RT under 40 psi $H_2$. The resulting mixture was filtered with Celite and washed with MeOH. The filtrate was evaporated on rotavap and pumped to dryness to give 37.64 g (100%) of the desired product. M+H$^+$ (215).

Step B

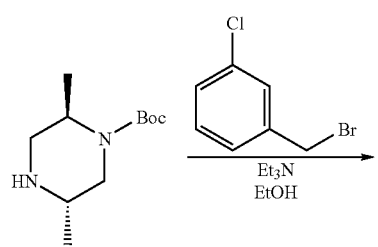

To the solution of 2R,5S-Dimethyl-piperazine-1-carboxylic acid tert-butyl ester (10.34 g, 37.74 mmol) in ethanol (100 mL) was added 3-chloro-benzyl bromide (4.96 mL, 37.74 mmol) and triethylamine (21 mL, 150 mmol). The mixture was stirred at RT for 16 h. The reaction was evaporated on rotavap and was extracted with EtOAc from water. The crude material was purified on silica gel with 0-5% EtOAc in hexane to give 8.4 g (66%) of the desired product. M+H$^+$ (339).

Step C

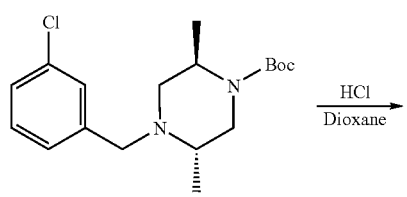

-continued

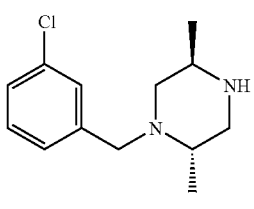

4-(3-Chloro-benzyl)-2R,5S-dimethyl-piperazine-1-carboxylic acid tert-butyl ester (5.8 g, 17.2 mmol) was dissolved into 30 mL 4 M HCl in 1,4-dioxane. The reaction mixture was stirred at RT overnight. The crude was filtered and washed with ether. The solid was dissolve into 20% NaOH aqueous solution. The aqueous solution was extracted with EtOAc. The combined organics were washed with brine, dried and concentrated. The product was obtained as white solid (4.0 g, 98%). M+H$^+$(239).

Step D

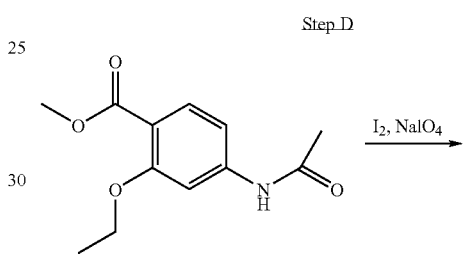

A mixture of methyl ester (30 g, 126 mmol), iodine (32 g, 126 mmol) and sodium periodate (13.5 g, 63 mmol) in anhydrous DMF (700 mL) was heated up at 70° C. for 24 h. The reaction mixture was poured into ice water and a solution of sodium thiosulfate (10% water solution) was added to destroy the excess iodine. The yellow precipitate formed was filtered and dried to give 35 g of the desired product in 76% yield. The crude product was used in the next reaction without further purification. M+H$^+$(364).

Step E

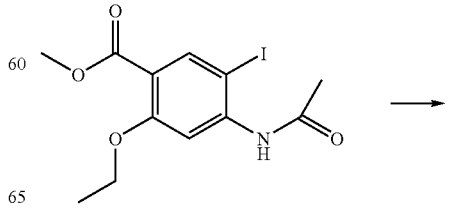

-continued

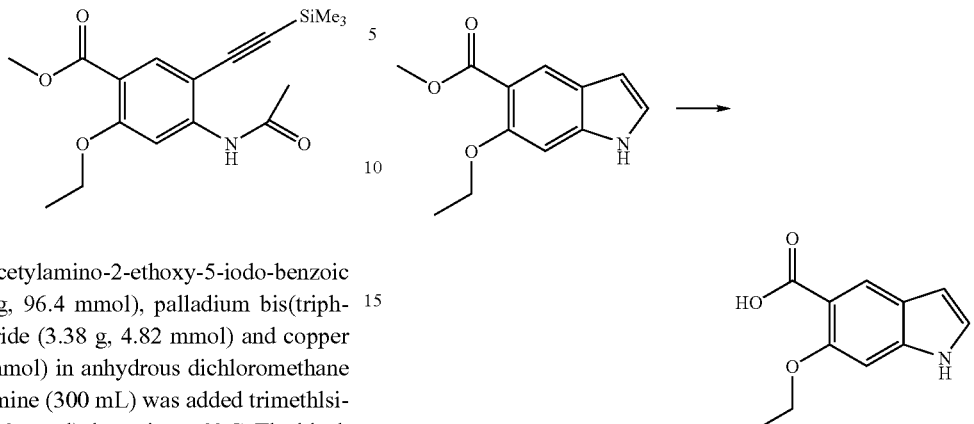

To a solution of 4-acetylamino-2-ethoxy-5-iodo-benzoic acid methyl ester (35 g, 96.4 mmol), palladium bis(triphenylphosphane) dichloride (3.38 g, 4.82 mmol) and copper iodide (918 mg, 4.82 mmol) in anhydrous dichloromethane (300 mL) and triethylamine (300 mL) was added trimethlsilyacetylene (15 mL, 10.6 mmol) dropwise at 0° C. The black reaction mixture was warmed to RT and stirred overnight, filtered through a plug of celite and concentrated. The residue was taken up into ethyl acetate, and washed with water and brine, dried and concentrated. The residue was dry loaded on a silica gel column and purified by eluting with EtOAc:hexane (1:4) to give 28 g (67%) of the desired product. M+H$^+$ (334).

Step F

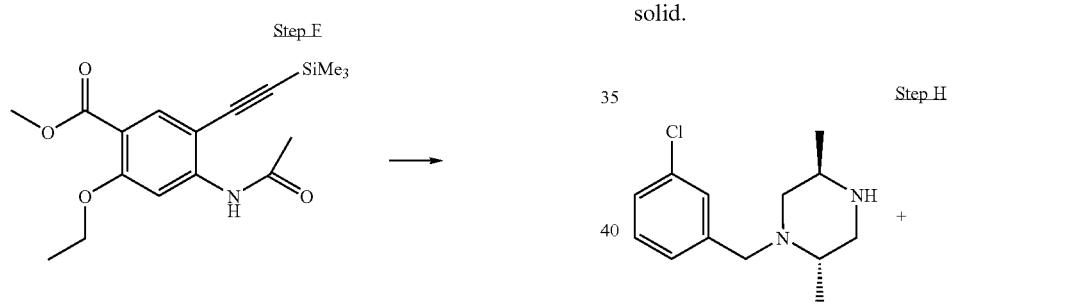

A mixture of 4-Acetylamino-2-ethoxy-5-trimethylsilanylethynyl-benzoic acid methyl ester (28 g, 84 mmol) and tetrabutylammonium fluoride (168 mL, 168 mmol, 1.0 M in THF) in anhydrous THF was heated at reflux for 4 h. The reaction mixture was concentrated and the residue was taken up into ethyl acetate. The organic layer was washed with water, brine, dried and concentrated. The product was crystallized from ethyl acetate, filtered and dried. The filtrate was filtered through a plug of silica gel. M+H$^+$(220)

Step G

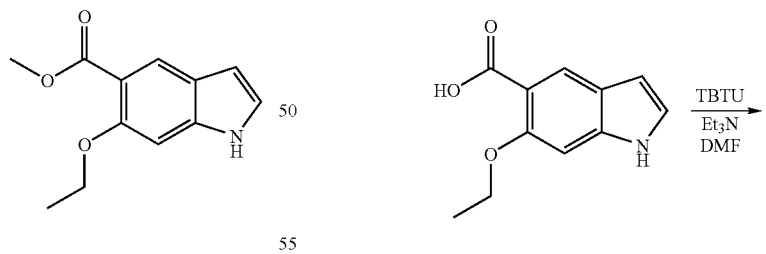

NaOH (17.7 g, 10% water solution) was added to a solution of indole methyl ester (19.4 g, 88.6 mmol) in MeOH (350 mL). The reaction mixture was heated at reflux for 2 h and then the solvent was removed. The resulting mixture was acidified with 10% HCl solution and a precipitate was formed. The suspension was extracted with EtOAc. The combined organic layer was washed with brine, dried and concentrated to give 18 g (89%) of the title compound as a yellow solid.

Step H

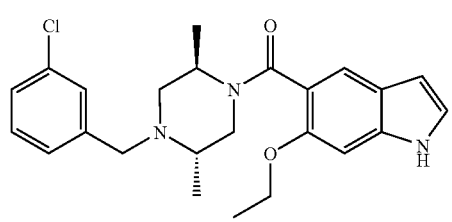

Prepared from 6-Ethoxy-1H-indole-5-carboxylic acid as in Example 3, Step F (72% yield). M+H⁺(426).

EXAMPLE 19

1-{1-Amino-5-[4-(2-chloro-benzyl)-2R,5S-dimethyl-piperazine-1-carbonyl]-6-ethoxy-1H-indol-3-yl}-2-pyrrolidin-1-yl-ethane-1,2-dione

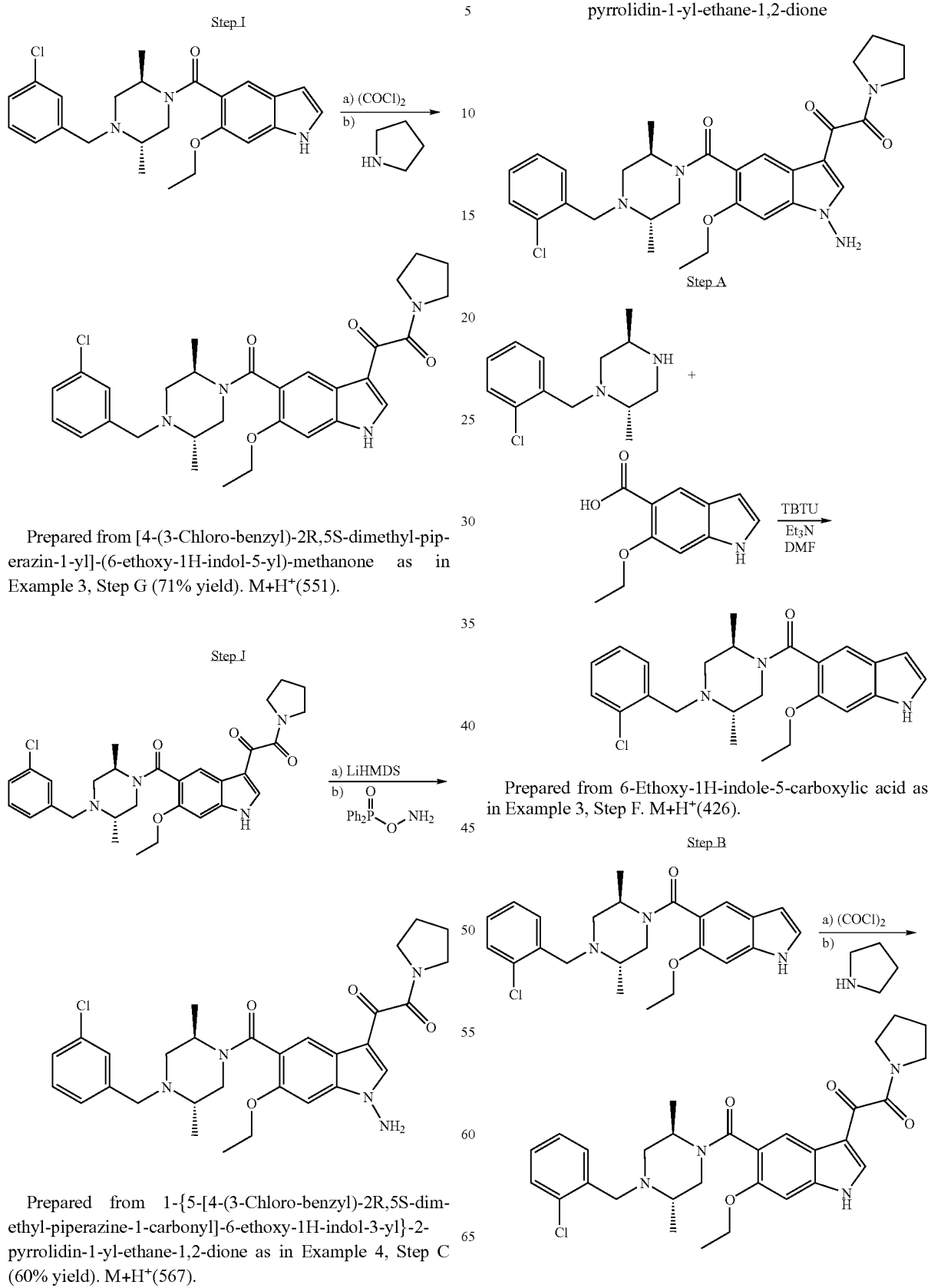

Prepared from [4-(3-Chloro-benzyl)-2R,5S-dimethyl-piperazin-1-yl]-(6-ethoxy-1H-indol-5-yl)-methanone as in Example 3, Step G (71% yield). M+H⁺(551).

Prepared from 6-Ethoxy-1H-indole-5-carboxylic acid as in Example 3, Step F. M+H⁺(426).

Prepared from 1-{5-[4-(3-Chloro-benzyl)-2R,5S-dimethyl-piperazine-1-carbonyl]-6-ethoxy-1H-indol-3-yl}-2-pyrrolidin-1-yl-ethane-1,2-dione as in Example 4, Step C (60% yield). M+H⁺(567).

Prepared from [4-(2-Chloro-benzyl)-2R,5S-dimethyl-piperazin-1-yl]-(6-ethoxy-1H-indol-5-yl)-methanone as in Example 3, Step G (53% yield). M+H⁺(551).

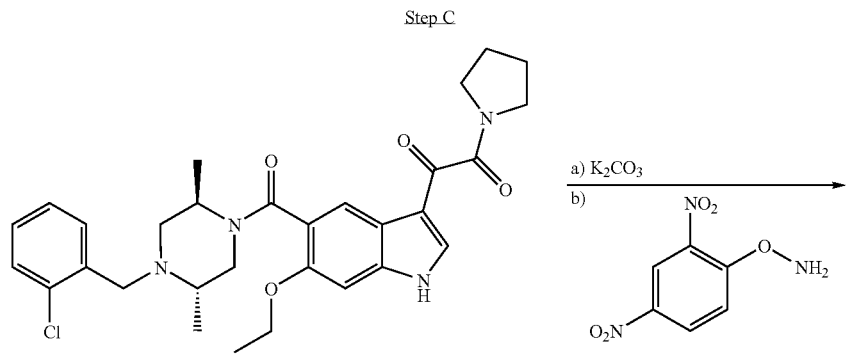

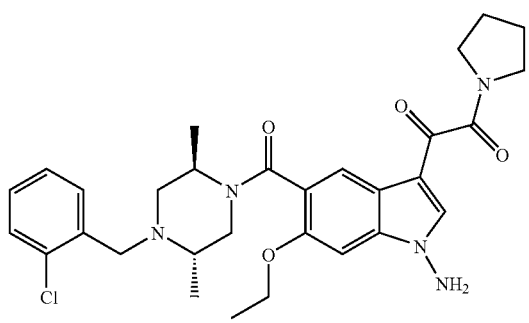

Prepared from 1-{5-[4-(2-Chloro-benzyl)-2R,5S-dimethyl-piperazine-1-carbonyl]-6-ethoxy-1H-indol-3-yl}-2-pyrrolidin-1-yl-ethane-1,2-dione as in Example 3, Step H, method 2 (58% yield). M+H⁺(567).

EXAMPLE 20

2-{1-Amino-6-chloro-5-[4-(3-chloro-benzyl)-2R,5S-dimethyl-piperazine-1-carbonyl]-1H-indol-3-yl}-2-oxo-acetamide

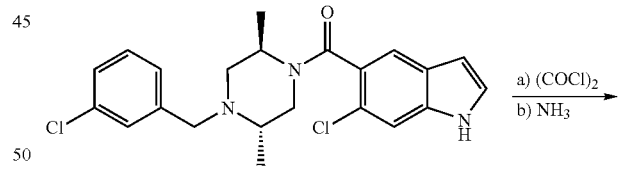

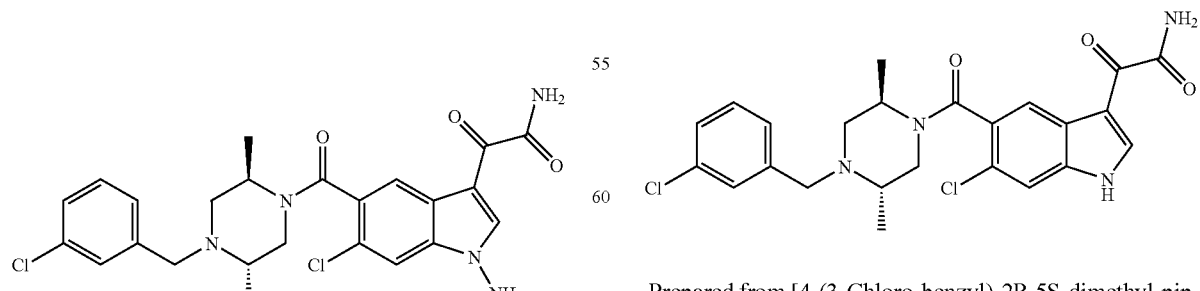

Prepared from [4-(3-Chloro-benzyl)-2R,5S-dimethyl-piperazin-1-yl]-(6-chloro-1H-indol-5-yl)-methanone as in Example 3, Step G using ammonia in dioxane in place of pyrrolidine (62% yield). M+H⁺(488).

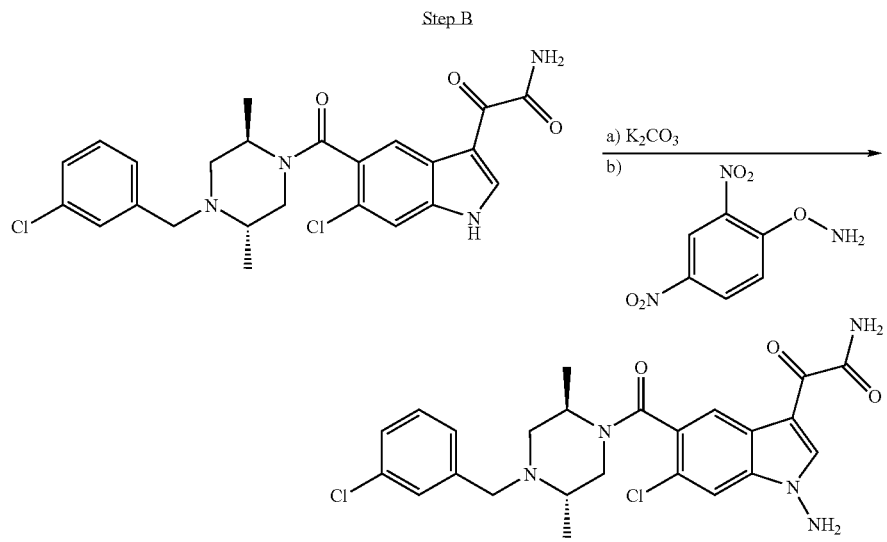

Performed using 2-{6-Chloro-5-[4-(3-chloro-benzyl)-2R, 5S-dimethyl-piperazine-1-carbonyl]-1H-indol-3-yl}-2-oxo-acetamide as in Example 3, Step H, Method 1 (54% yield). M+H⁺(503).

EXAMPLE 21

2-{1-Amino-6-chloro-5-[4-(3-chloro-benzyl)-2R,5S-dimethyl-piperazine-1-carbonyl]-1H-indol-3-yl}-N-methyl-2-oxo-acetamide

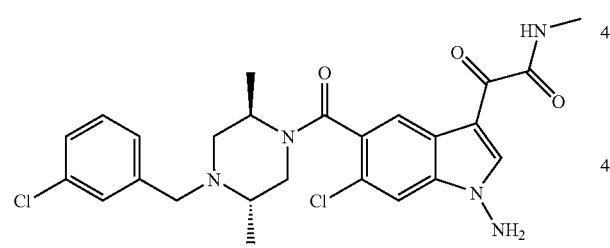

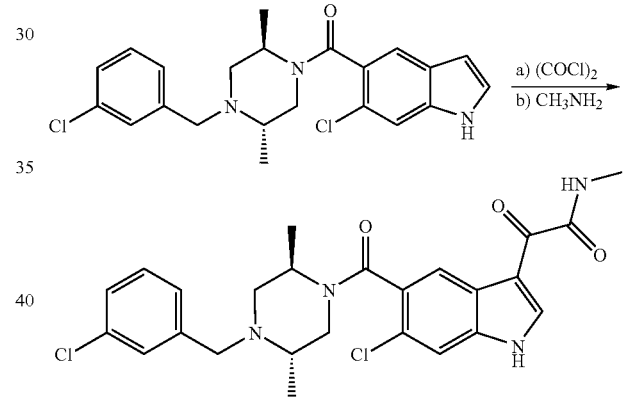

Prepared from [4-(3-Chloro-benzyl)-2R,5 S-dimethyl-piperazin-1-yl]-(6-chloro-1H-indol-5-yl)-methanone as in Example 3, Step G using methylamine in place of pyrrolidine (88% yield). M+H⁺(502).

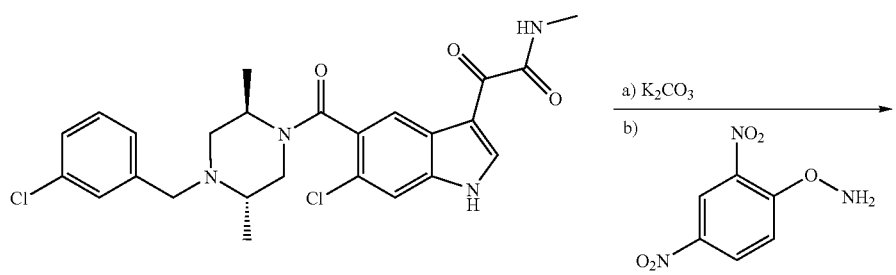

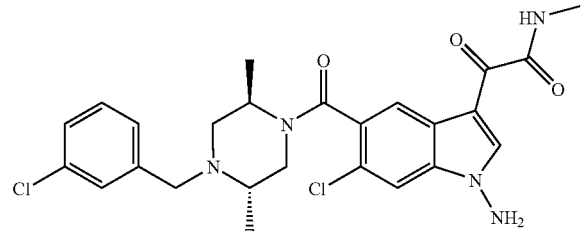

Performed using 2-{6-Chloro-5-[4-(3-chloro-benzyl)-2R,5S-dimethyl-piperazine-1-carbonyl]-1H-indol-3-yl}-N-methyl-2-oxo-acetamide as in Example 3, Step H, Method 1 (32% yield). M+H⁺(517).

EXAMPLE 22

2-{1-Amino-5-[4-(3-chloro-benzyl)-2R,5S-dimethyl-piperazine-1-carbonyl]-6-ethoxy-1H-indol-3-yl}-N,N-dimethyl-2-oxo-acetamide

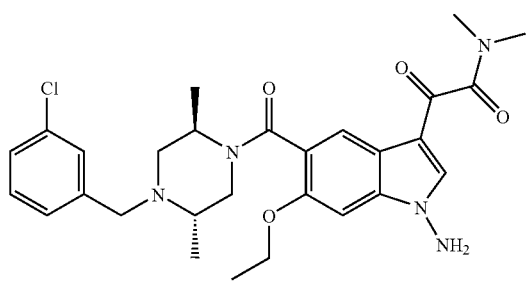

Step A

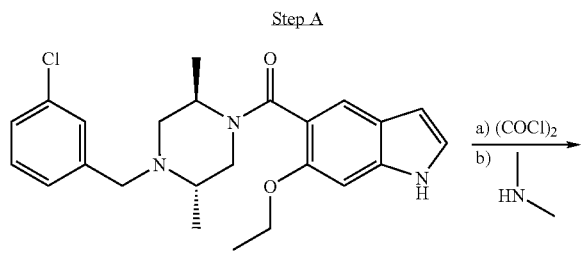

Prepared from [4-(3-chloro-benzyl)-2R,5S-dimethyl-piperazin-1-yl]-(6-ethoxy-1H-indol-5-yl)-methanone and dimethylamine as in Example 2, Step B. M+H⁺(526).

Step B

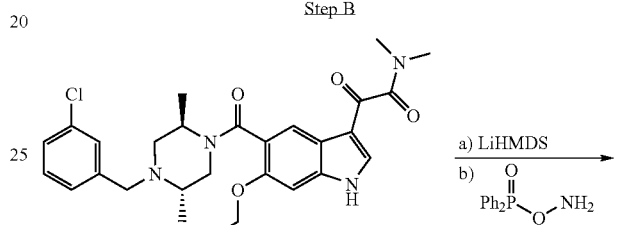

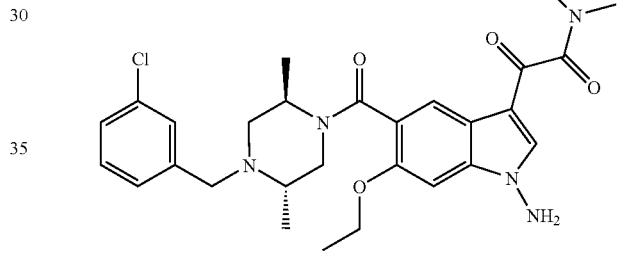

Prepared from 2-{5-[4-(3-chloro-benzyl)-2R,5S-dimethyl-piperazine-1-carbonyl]-6-ethoxy-1H-indol-3-yl}-N,N-dimethyl-2-oxo-acetamide as in Example 4, Step C. M+H⁺ (541).

EXAMPLE 23

Preparation of 1-{1-Amino-6-chloro-5-[4-(4-fluoro-benzyl)-trans-2,5-dimethyl-piperazine-1-carbonyl]-1H-indol-3-yl}-2-pyrrolidin-1-yl-ethane-1,2-dione

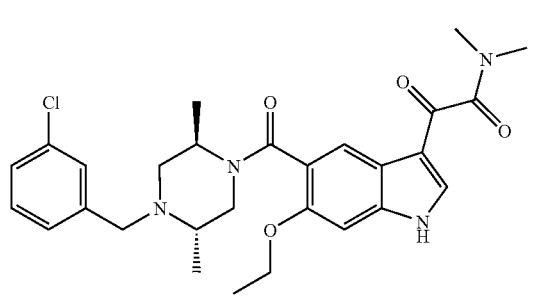

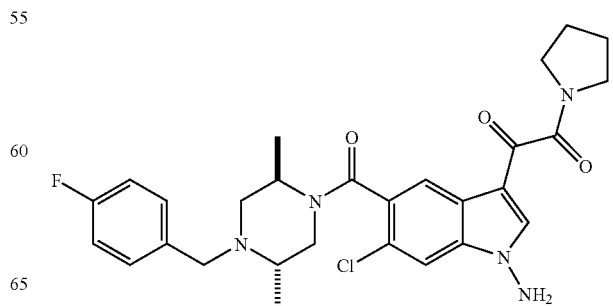

Step A

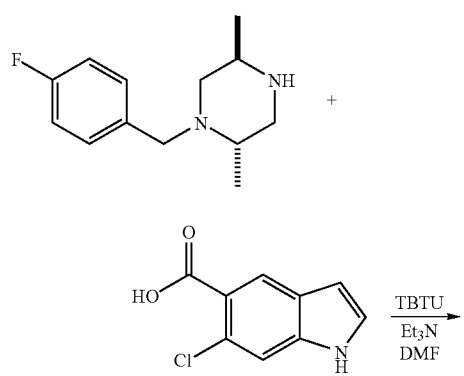

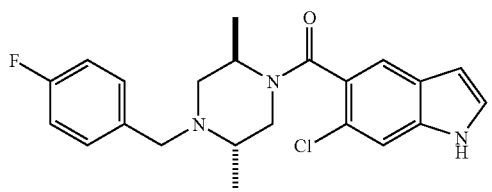

To a solution of 6-chloroindole-5-carboxylic acid (3.9 g, 19.8 mmol) and 4-fluorobenzyl-trans-2,5-dimethyl piperazine (4.4 g, 19.8 mmol) in THF was added TBTU (6.4 g, 19.8 mmol), followed by triethylamine (6.1 g, 60 mmol). The reaction mixture was stirred overnight at RT. and then poured into ice water. The mixture was extracted with dichloromethane. The combined organic layer was washed with brine, dried and concentrated. The residue was purified by chromatography on silica gel eluting with EtOAc:hexane(2:3) to give 6.1 g (77%) of the desired product as a white solid. M+H$^+$(400).

Step B

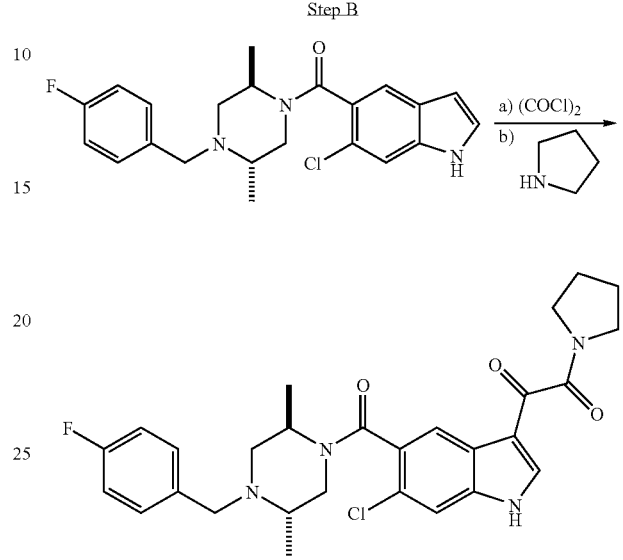

Performed using (6-Chloro-1H-indol-5-yl)-[4-(4-fluorobenzyl)-trans-2,5-dimethyl-piperazin-1-yl]-methanone as in Example 3, Step G (80% yield). M+H$^+$(526).

Step C

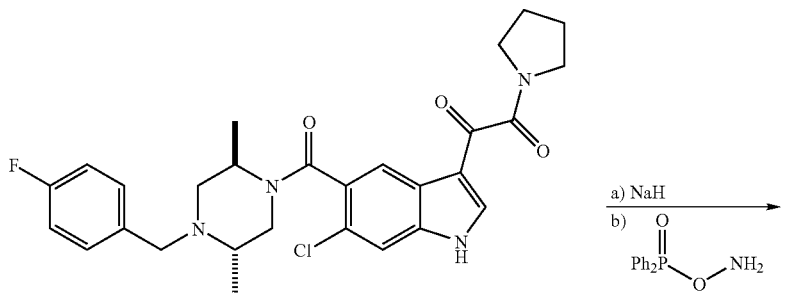

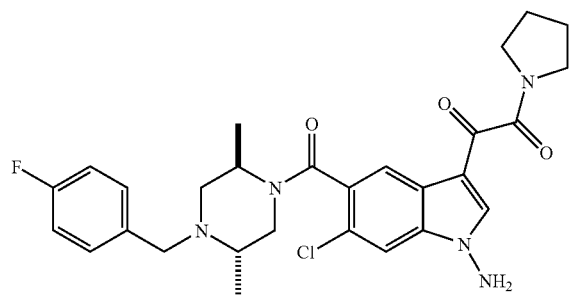

Performed using 1-{6-Chloro-5-[4-(4-fluoro-benzyl)-trans-2,5-dimethyl-piperazine-1-carbonyl]-1H-indol-3-yl}-2-pyrrolidin-1-yl-ethane-1,2-dione as in Example 3, Step H (Method 1) (98% yield). M+H+(541).

EXAMPLE 24

1-{1-Amino-6-chloro-5-[4-(4-fluoro-benzyl)-2R,5S-dimethyl-piperazine-1-carbonyl]-1H-indol-3-yl}-2-(R-(+)-3-methoxy-pyrrolidin-1-yl)-ethane-1,2-dione

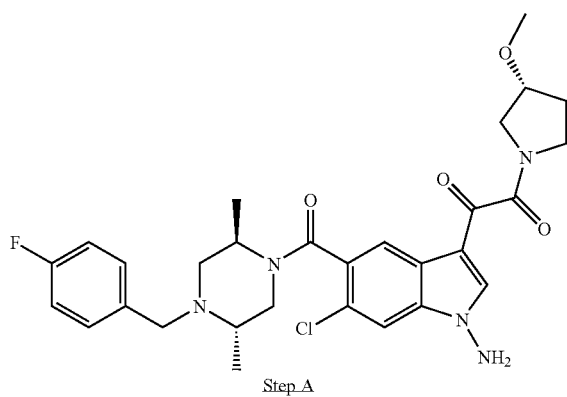

Step A

A solution of (R)-1-benzyl-3-pyrolidinol (500 mg, 2.82 mmol) in DMF (10 mL) was added to a suspension of NaH (135 mg, 5.65 mmol) in DMF dropwise at RT. The reaction mixture was stirred for 30 min. Methyl iodide was added dropwise. The reaction mixture was continually stirred for 2 h, quenched with Na₂CO₃, extracted with EtOAc. The combined organic layer was washed with water, brine, dried and concentrated. The residue was purified by chromatography on silica gel eluting with EtOAc to give 240 mg (44%) of the desired product. M+H+(192).

Step B

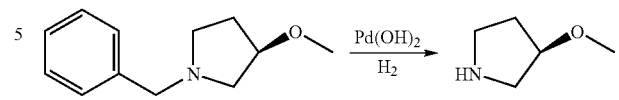

A mixture of 1-benzyl-3-(R)-methoxy-pyrrolidine (240 mg), Pd(OH)₂ (75 mg) and HOAc (0.1 mL) in ethanol (20 mL) was hydrogenated at 50° C. under 40 psi for 3 h. The reaction mixture was filtered through a plug of celite. The filtrate was concentrated and dried to give 100 mg (79%) of the desired product.

Step C

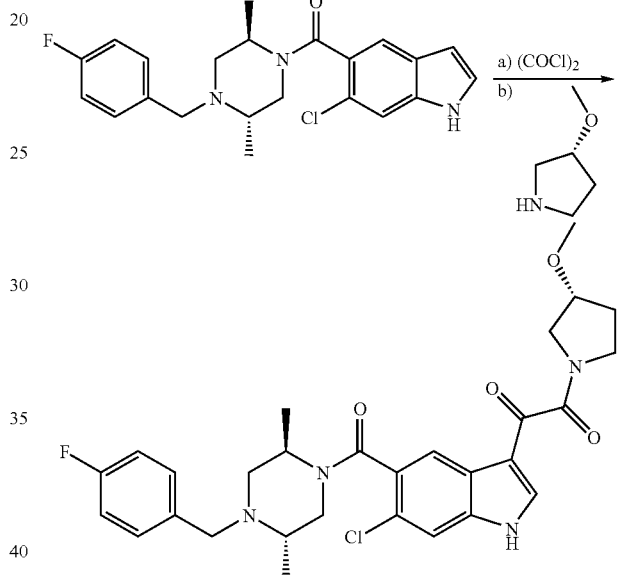

Prepared from (6-Chloro-1H-indol-5-yl)-[4-(4-fluoro-benzyl)-2R,5S-dimethyl-piperazine-1-yl]-methanone as in Example 3, Step G using R-(+)-3-methoxypyrrolidine in place of pyrrolidine. M+H+ (556).

Step D

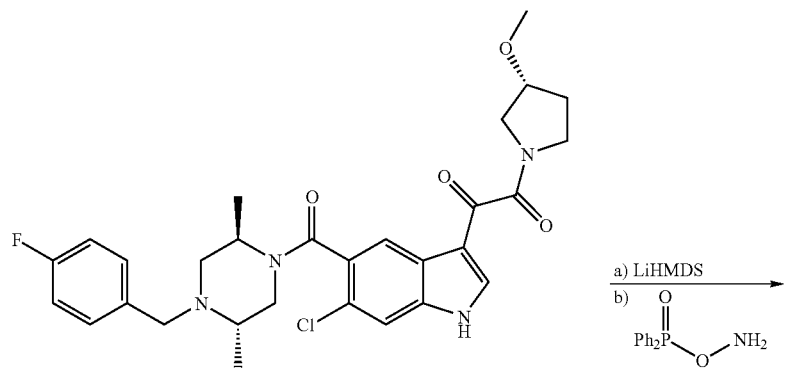

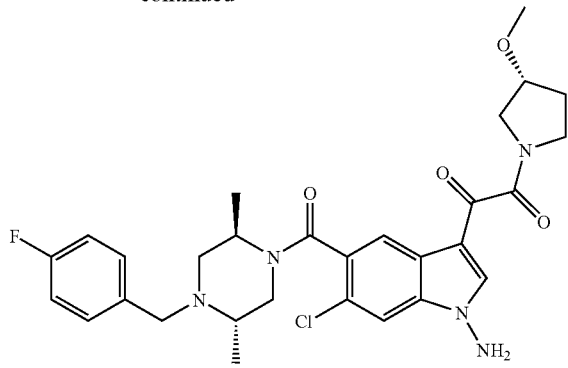

Prepared from 1-{6-Chloro-5-[4-(4-fluoro-benzyl)-2R,5S-dimethyl-piperazine-1-carbonyl]-1H-indol-3-yl}-2-(R-(+)-3-methoxy-pyrrolidin-1-yl)-ethane-1,2-dione as in Example 2, Step C. M+H⁺ (571).

EXAMPLE 25

Preparation of 1-{1-Amino-6-chloro-5-[4-(4-fluoro-benzyl)-2R,5S-dimethyl-piperazine-1-carbonyl]-1H-indol-3-yl}-2-azetidin-1-yl-ethane-1,2-dione

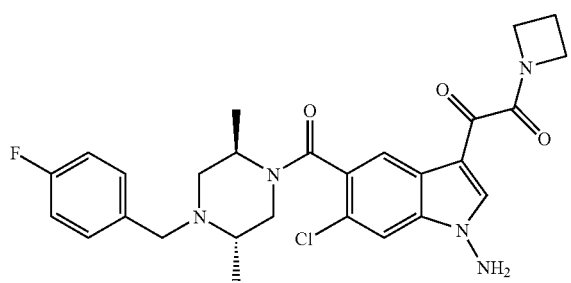

-continued
Step A

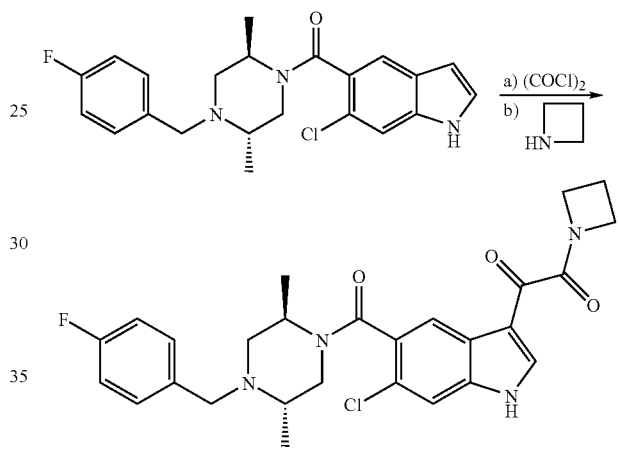

Prepared from (6-Chloro-1H-indol-5-yl)-[4-(4-fluoro-benzyl)-2R,5S-dimethyl-piperazine-1-yl]-methanone as in Example 3, Step G using azetidine in place of pyrrolidine. M+H⁺(511).

Step B

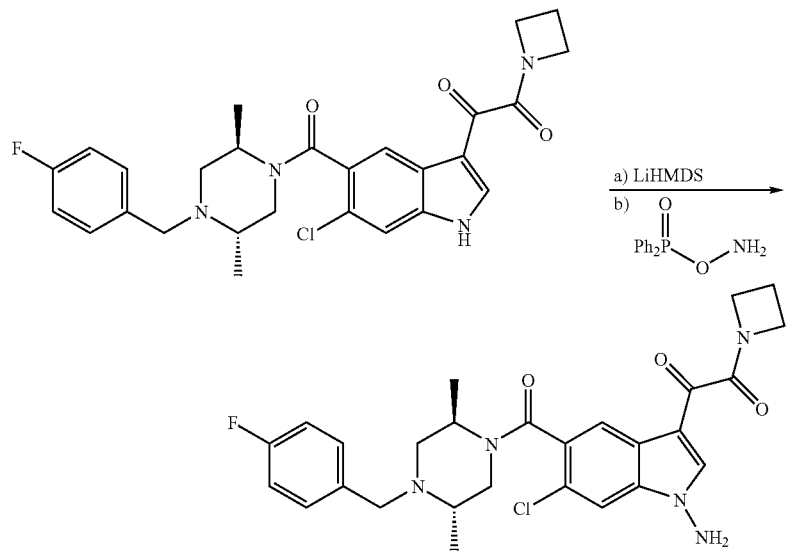

Prepared from 1-Azetidin-1-yl-2-{6-chloro-5-[4-(4-fluoro-benzyl)-2R,5S-dimethyl-piperazine-1-carbonyl]-1H-indol-3-yl}-ethane-1,2-dione as in Example 3, Step H. M+H⁺ (527).

EXAMPLE 26

1-{1-Amino-6-chloro-5-[4-(4-fluoro-benzyl)-2R-methyl-piperazine-1-carbonyl]-1H-indol-3-yl}-2-pyrrolidin-1-yl-ethane-1,2-dione

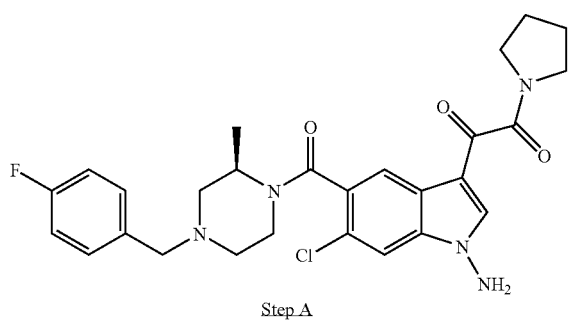

Step A

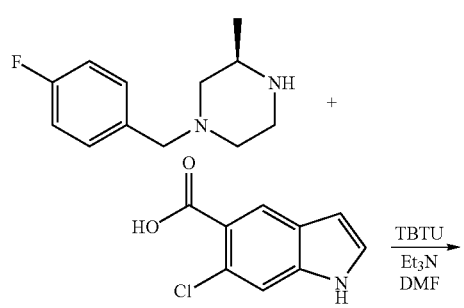

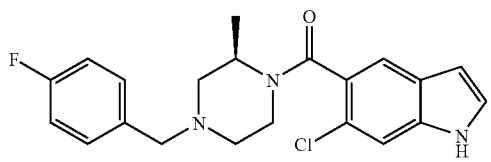

-continued

Prepared 1-(4-Fluoro-benzyl)-3R-methyl-piperazine and 6-chloroindole-5-carboxylic acid as in Example 3 Step F. M+H⁺(386).

Step B

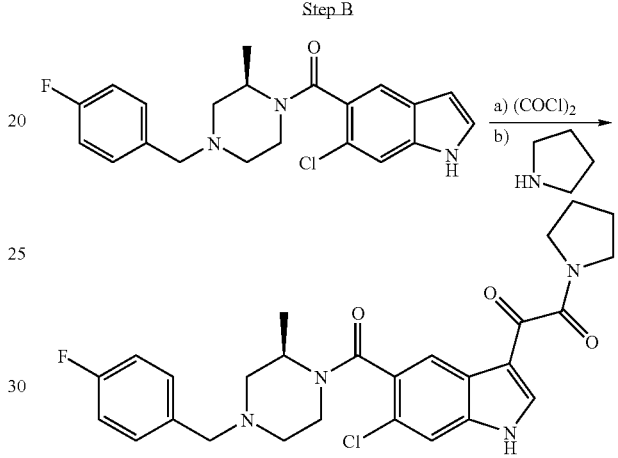

Performed using (6-Chloro-1H-indol-5-yl)-[4-(4-fluoro-benzyl)-2R-methyl-piperazin-1-yl]-methanone as in Example 3, Step G. M+H⁺(511).

Step C

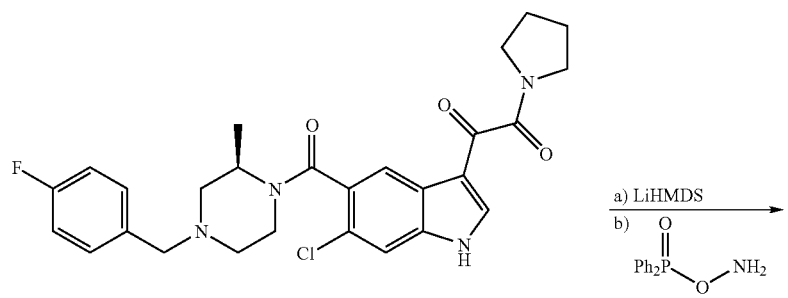

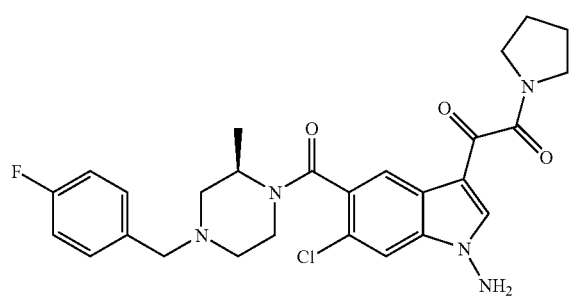

Performed using 1-{6-Chloro-5-[4-(4-fluoro-benzyl)-2R-methyl-piperazine-1-carbonyl]-1H-indol-3-yl}-2-pyrrolidin-1-yl-ethane-1,2-dione as in Example 3, Step H (Method 1). M+H⁺(526).

EXAMPLE 27

2-[1-Amino-6-chloro-5-[4-(4-fluoro-benzyl)-2R-methyl-piperazine-1-carbonyl]-1H-indol-3-yl}-N-methoxy-N-methyl-2-oxo-acetamide Step A

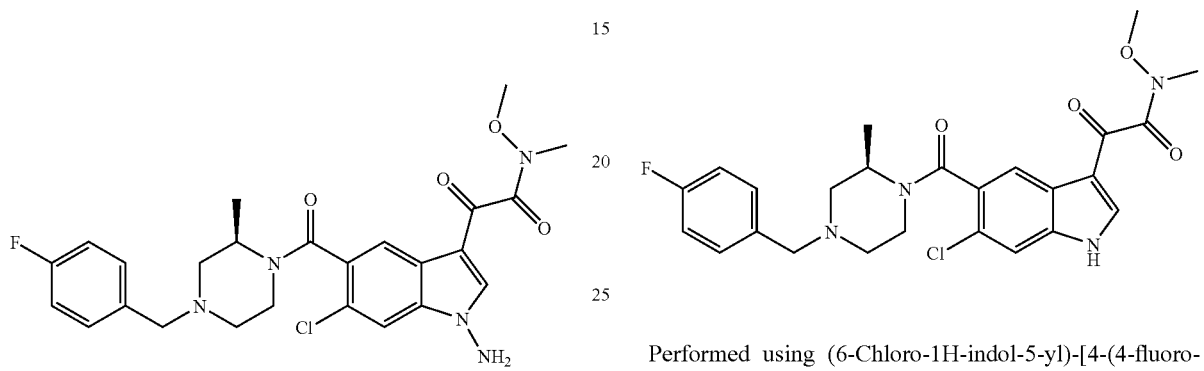

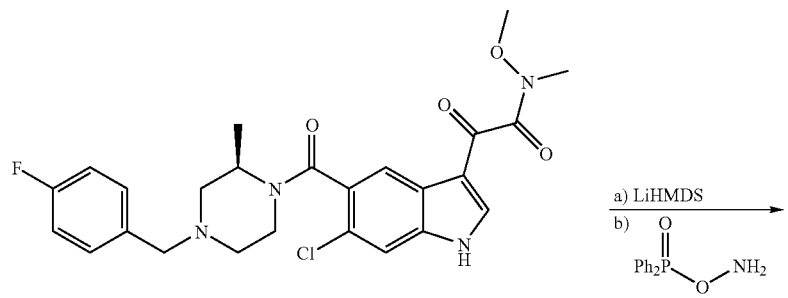

Performed using (6-Chloro-1H-indol-5-yl)-[4-(4-fluoro-benzyl)-2R-methyl-piperazine-1-yl]-methanone as in Example 3, Step G using N,O-dimethylhydroxylamine in place of pyrrolidine. M+H⁺(501).

Step B

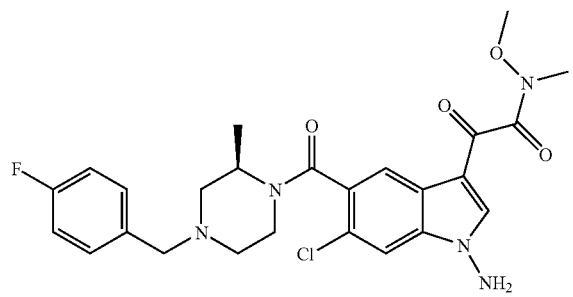

Performed using 2-{6-Chloro-5-[4-(4-fluoro-benzyl)-2R-methyl-piperazine-1-carbonyl]-1H-indol-3-yl}-N-methoxy-N-methyl-2-oxo-acetamide as in Example 3, Step H (Method 1). M+H⁺(516).

EXAMPLE 28

1-{1-Amino-6-chloro-5-[4-(4-fluoro-benzyl)-2R-methyl-piperazine-1-carbonyl]-1H-indol-3-yl}-2-(R-(+)-3-hydroxy-pyrrolidin-1-yl)-ethane-1,2-dione -continued Step A

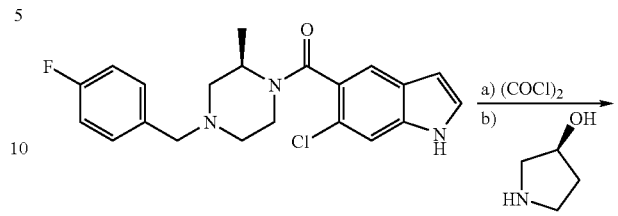

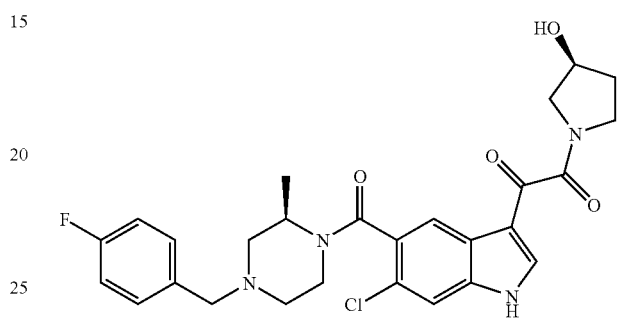

Performed using (6-Chloro-1H-indol-5-yl)-[4-(4-fluoro-benzyl)-2R-methyl-piperazin-1-yl]-methanone as in Example 3, Step G using S-(−)-3-hydroxypyrrolidine in place of pyrrolidine. M+H⁺(527).

Step B

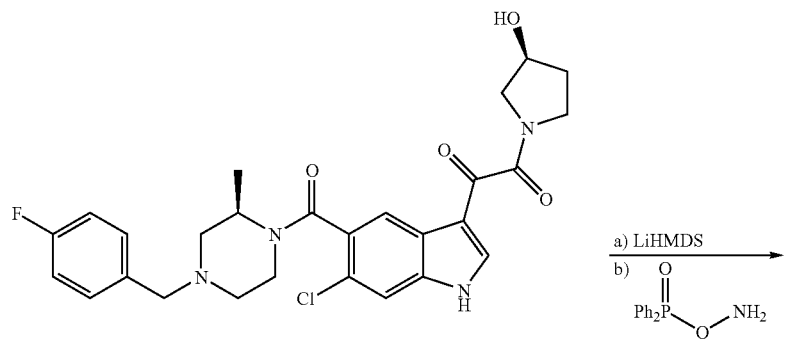

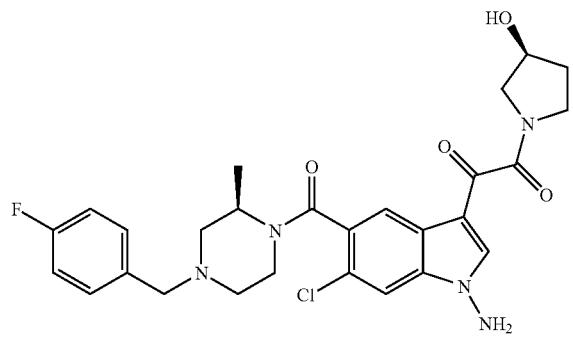

Performed using 1-{6-Chloro-5-[4-(4-fluoro-benzyl)-2R-methyl-piperazine-1-carbonyl]-1H-indol-3-yl}-2-(S-(−)-3-hydroxy-pyrrolidin-1-yl)-ethane-1,2-dione as in Example 3, Step H (Method 1). M+H$^+$(542).

EXAMPLE 29

1-{1-Amino-5-[4-(4-fluoro-benzyl)-2R,5S-dimethyl-piperazine-1-carbonyl]-6-methyl-1H-indol-3-yl}-2-pyrrolidin-1-yl-ethane-1,2-dione

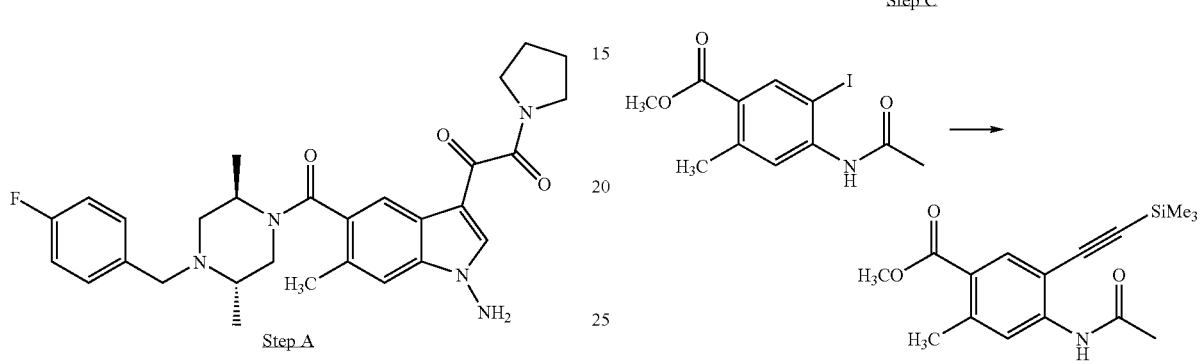

Step A

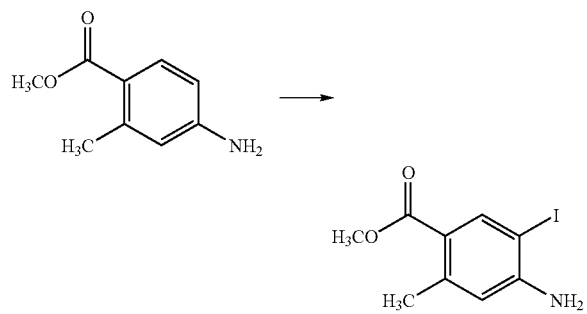

To a solution of methyl 5-methyl-4-aminobenzoate (1.1 g, 6.7 mmol) in 4 mL DMF was added NaIO$_4$ (573 mg, 2.68 mmol) and iodine (1.35 g, 5.3 mmol). The mixture was warmed at 50° C. for 4 h. It was then cooled and diluted with water and the product was extracted with ethyl acetate. The organic layer was dried with Na$_2$SO$_4$ and concentrated. The residue was purified by column chromatography using 10% EtOAc and hexane to give 2.2 g of product as brown solids. M+H$^+$(292).

Step B

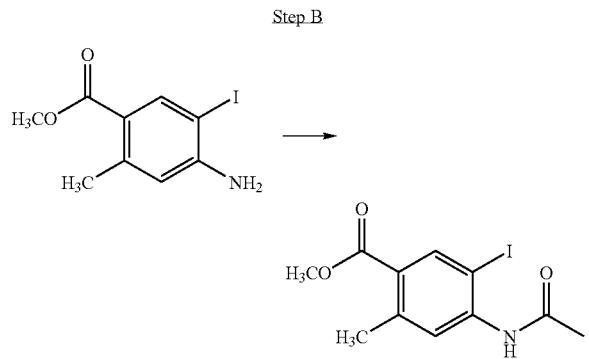

To a solution of 4-amino-5-iodo-2-methyl-benzoic acid methyl ester (2.2 g, 7.5 mmol) in 20 mL THF was added pyridine (888 mg, 11.25 mmol). The solution was cooled to 0° C. and acetyl chloride (765 mg, 9.75 mmol) was added slowly. Stirring was continued for 3 h and the mixture was poured into EtOAc, washed with water and brine. The organic layer was dried with Na$_2$SO$_4$ and concentrated. The residue was purified by column chromatography using 25% EtOAc and hexane to give the desired product. M+H$^+$(334).

Step C

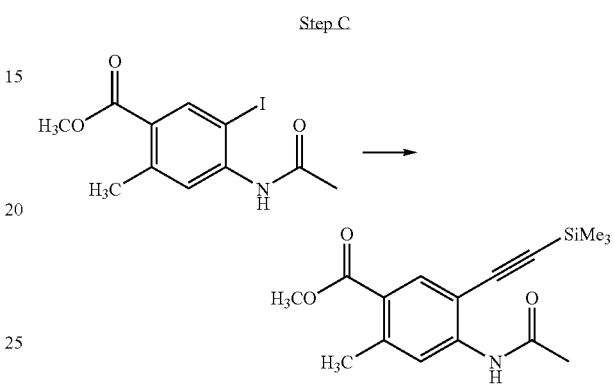

To a solution of compound 4-acetylamino-5-iodo-2-methyl-benzoic acid methyl ester (850 mg, 2.56 mmol) in 10 mL Et$_3$N and 10 mL CH$_2$Cl$_2$ was added CuI (20 mg, 0.11 mmol) and (Ph$_3$P)$_2$PdCl$_2$ (77 mg, 0.11 mmol). It was then cooled to 0° C. and trimethylsilylacetylene (276 mg, 2.81 mmol) was added slowly. The temperature was raised to RT and stirring continued for 2 h. The mixture was poured into EtOAc and washed with water and brine. The organic layer was dried with Na$_2$SO$_4$ and concentrated. The residue was purified by column chromatography using EtOAc and hexane to give 720 mg (93%) of product. M+H$^+$(304).

Step D

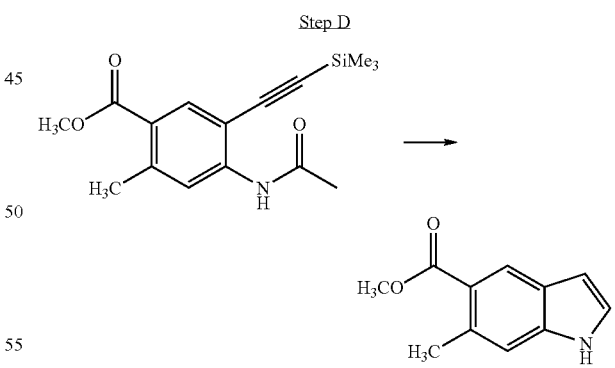

To a solution of compound 4-acetylamino-2-methyl-5-trimethylsilanylethynyl-benzoic acid methyl ester (720 mg, 2.37 mmol) in 2 mL THF was added 5 mL of 1M solution of tetrabutylammonium fluoride in THF and refluxed for 2 h. Extracted with EtOAc and washed with water and brine. The organic layer was dried with Na$_2$SO$_4$ and concentrated. The residue was purified by column chromatography using EtOAc and hexane to give 108 mg (25%) of product as white solids. M+H$^+$(190).

Step E

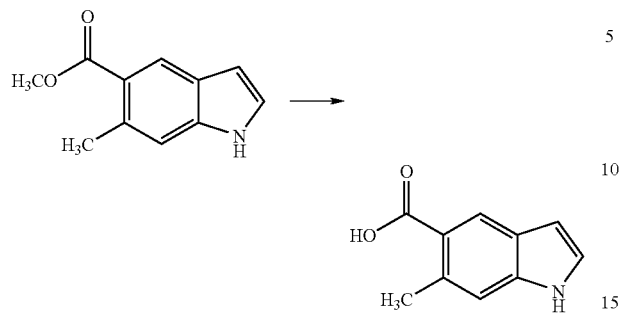

To a solution of 6-methyl-1H-indole-5-carboxylic acid methyl ester (108 mg, 0.57 mmol) in 5 mL MeOH and 5 mL water was added NaOH (116 mg, 2.9 mmol) and the mix was heated at 50° C. overnight. The solution was cooled, diluted with water and acidified to pH 3 and extracted with EtOAc, washed with water and brine. The organic layer was dried with Na$_2$SO$_4$ and concentrated to give 80 mg (80%) of product as white solids.

Step F

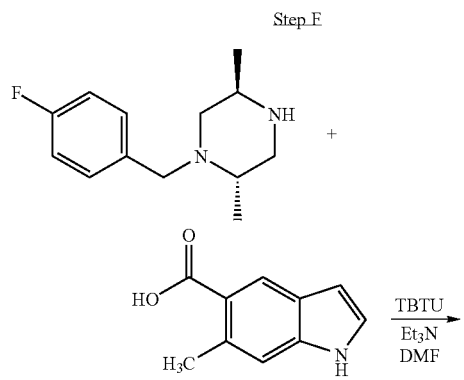

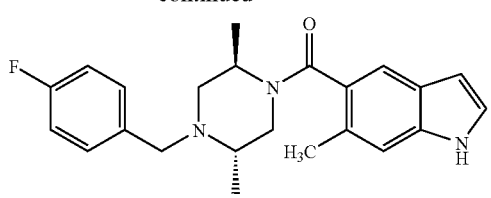

Prepared from 6-methyl-1H-indole-5-carboxylic acid as in Example 3, Step F. M+H$^+$(380).

Step G

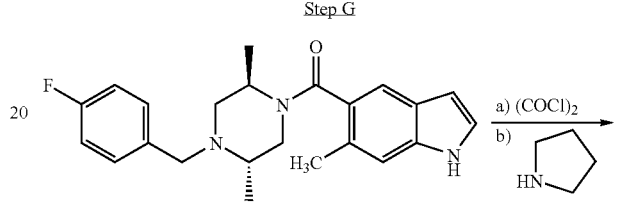

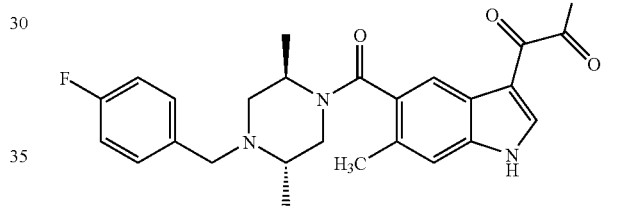

Prepared from [4-(4-Fluoro-benzyl)-2R,5S-dimethyl-piperazin-1-yl]-(6-methyl-1H-indol-5-yl)-methanone as in Example 3, Step G. M+H$^+$(505).

Step H

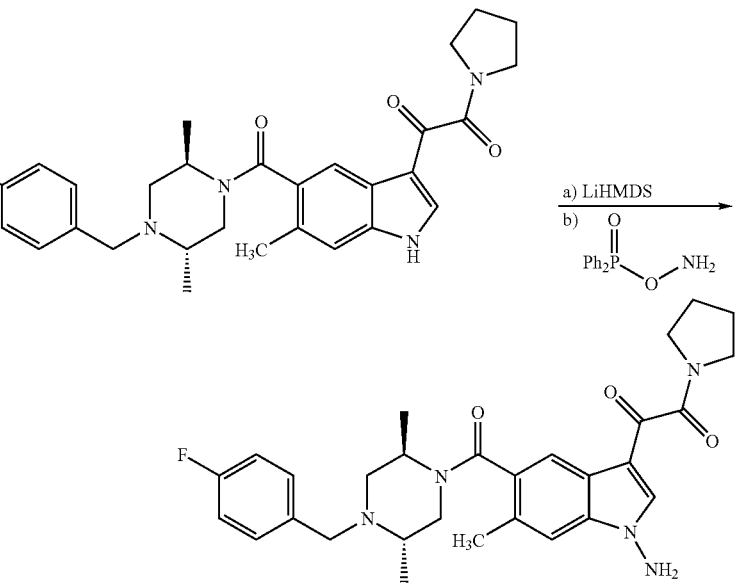

Prepared from 1-{5-[4-(4-Fluoro-benzyl)-2R,5S-dimethyl-piperazine-1-carbonyl]-6-methyl-1H-indol-3-yl}-2-pyrrolidin-1-yl-ethane-1,2-dione as in Example 6, Step C. M+H⁺(520).

EXAMPLE 30

1-[1-Amino-5-(4-benzyl-2R,5S-dimethyl-piperazine-1-carbonyl)-6-chloro-1H-indol-3-yl]-2-pyrrolidin-1-yl-ethane-1,2-dione

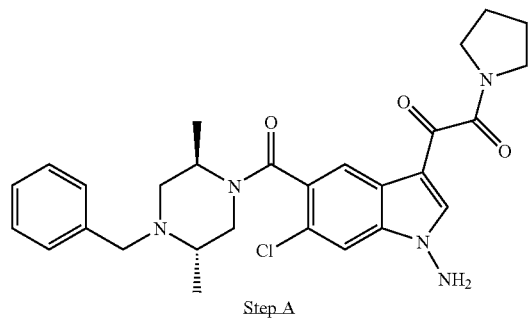

Step A

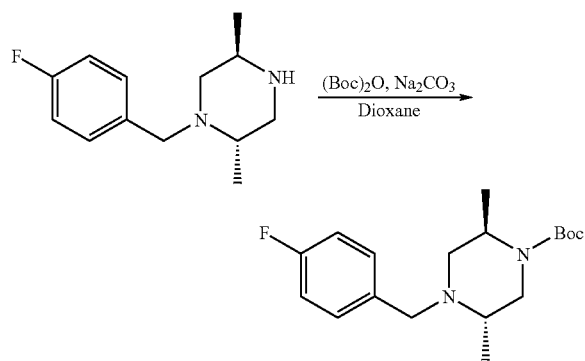

To the dioxane solution of 1-(4-Fluoro-benzyl)-2S,5R-dimethyl-piperazine (3.34 g, 15.05 mmol) was added Boc anhydride (4.92 g, 22.6 mmol) and sodium carbonate (1.59 g, 15.05 mmol) sequentially. The reaction was then stirred overnight at RT. After removing the reaction solvent, the residue was dissolved in 200 mL ethyl acetate. The ethyl acetate suspension was then washed with water 200 mL. After separation, the water layer was extracted with ethyl acetate (200 mL×2). The organic layers were combined and washed with water (200 mL×2) and saturated sodium chloride solution, dried over sodium sulfate. After concentration, the residue was purified with flash column eluding with 5-10% ethyl acetate in hexane. An oil-like product (2.21 g) was obtained.

Step B

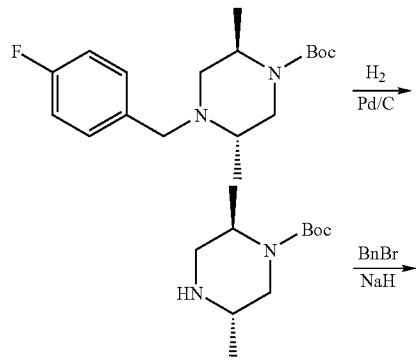

-continued

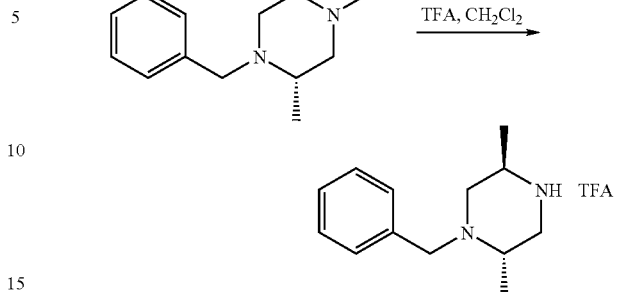

To the ethanol solution of 4-(4-fluoro-benzyl)-2R,5S-dimethyl-piperazine-1-carboxylic acid tert-butyl ester was added 500 mg Pd/C (10% wet), the reaction was hydrogenated at 40 psi overnight. After filtration and evaporating solvent, 1.75 g 2R,5S-dimethyl-piperazine-1-carboxylic acid tert-butyl ester was obtained. After vacuum drying, the material was dissolved in 20 mL DMF. To the DMF solution of was added sodium hydride (656 mg, 16.4 mmol, 60% oil dispersion). After stirring for 15 min, benzyl bromide (2.1 g, 12.3 mmol) was added to the reaction. After stirring overnight, the reaction was diluted with ethyl acetate (100 mL) and water (100 mL) was added to quench the reaction. The water layer was then extracted with ethyl acetate (100 mL×2). The organic layers were combined and washed with water (100 mL×2) and brine, dried over sodium sulfate and evaporated. 3.8 g of an oil-like crude product was obtained which was pure enough to undergo next reaction.

To the 10 ml dichloromethane solution of 4-benzyl-2R,5S-dimethyl-piperazine-1-carboxylic acid tert-butyl ester was add trifluoroacetic acid (20 ml) at 0° C. Reaction was then warmed to RT and stirred overnight. The solvent was removed and the product dried under vaccum. 5.6 g of 1-benzyl-2R,5S-dimethyl-piperazine was obtained and was used in the next step reaction directly.

Step C

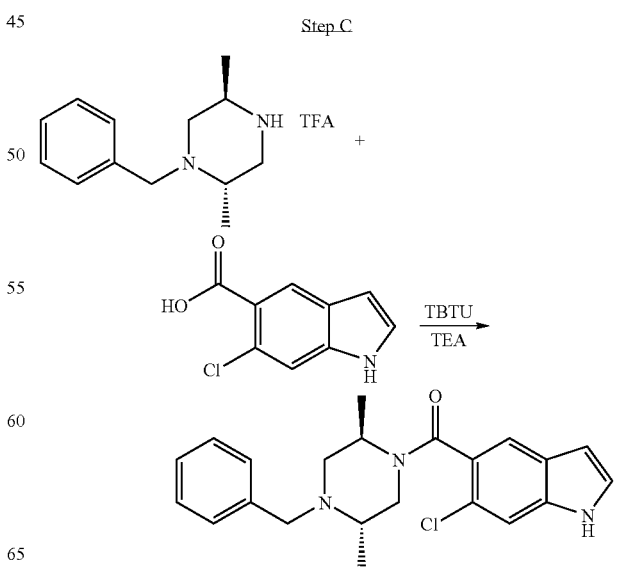

85

Prepared from 6-methyl-1H-indole-5-carboxylic acid and 1-benzyl-2S,5R-dimethyl-piperazine as in Example 3, Step F. M+H⁺(382).

Prepared from (4-Benzyl-2S,5R-dimethyl-piperazin-1-yl)-(6-chloro-1H-indol-5-yl)-methanone as in Example 3, Step G. M+H⁺(508).

Prepared from 1-[5-(4-Benzyl-2,5-dimethyl-piperazine-1-carbonyl)-6-chloro-1H-indol-3-yl]-2-pyrrolidin-1-yl-ethane-1,2-dione as in Example 6, Step C. M+H⁺(523).

86

EXAMPLE 31

1-[1-Amino-5-(4-benzyl-2R,5S-dimethyl-piperazine-1-carbonyl)-6-ethoxy-1H-indol-3-yl]-2-pyrrolidin-1-yl-ethane-1,2-dione

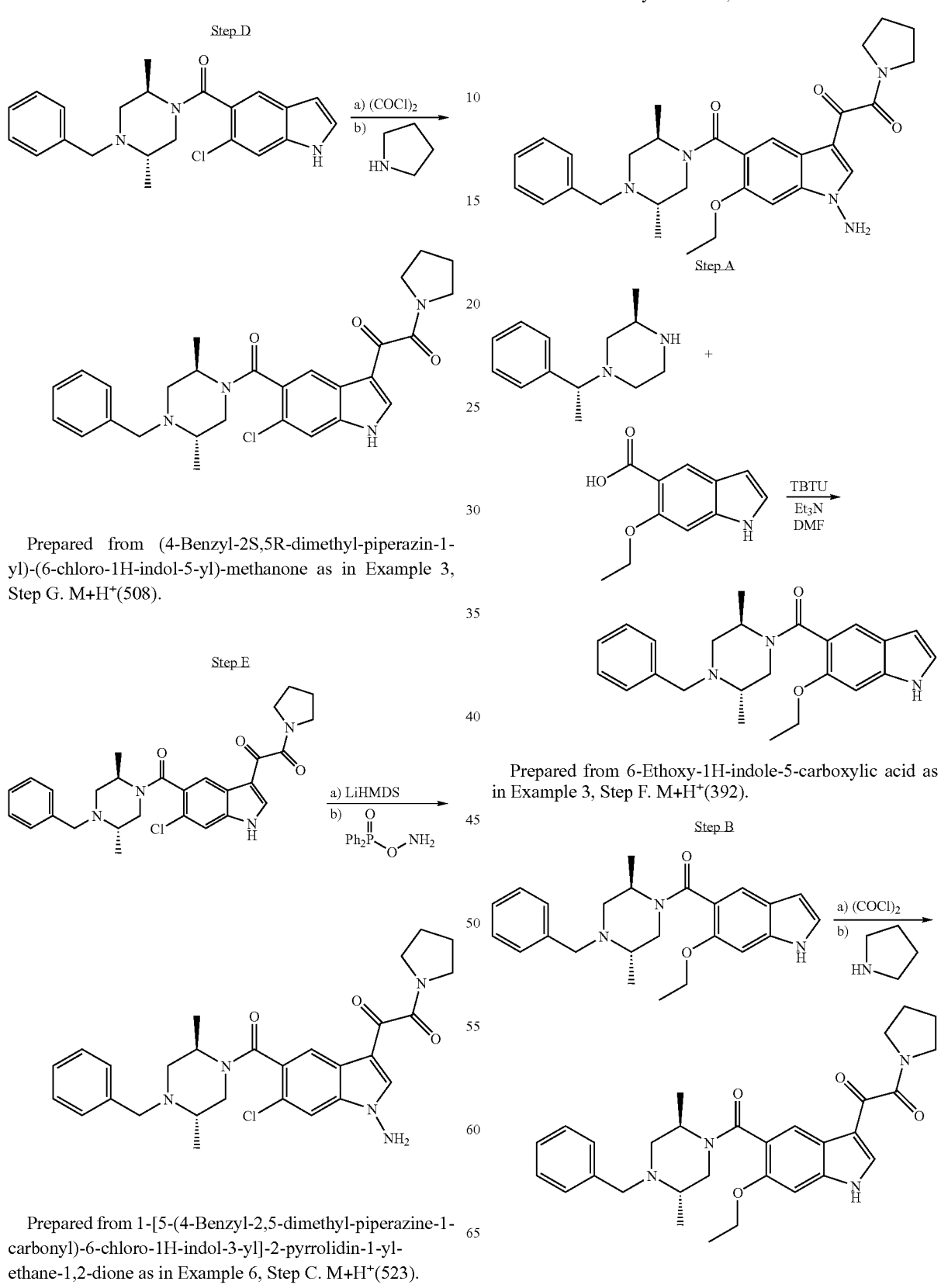

Prepared from 6-Ethoxy-1H-indole-5-carboxylic acid as in Example 3, Step F. M+H⁺(392).

Prepared from (4-Benzyl-2R,5S-dimethyl-piperazin-1-yl)-(6-ethoxy-1H-indol-5-yl)-methanone as in Example 3, Step G (78% yield). M+H⁺(517).

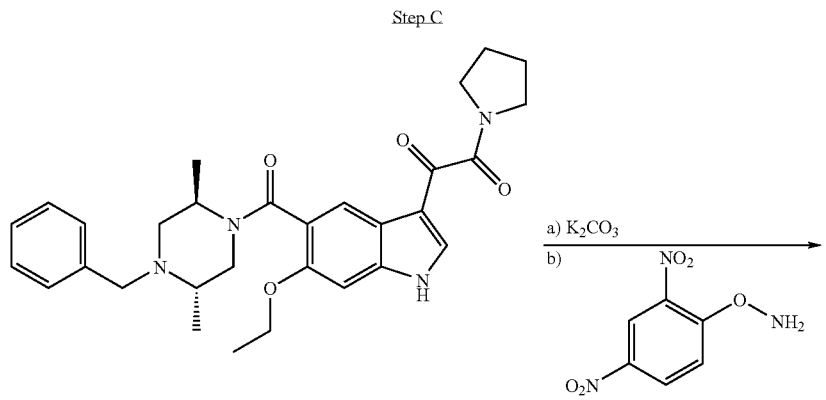

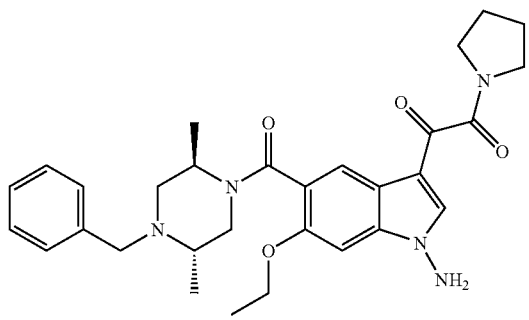

Prepared from 1-[5-(4-Benzyl-2R,5S-dimethyl-piperazine-1-carbonyl)-6-ethoxy-1H-indol-3-yl]-2-pyrrolidin-1-yl-ethane-1,2-dione as in Example 3, Step H, method 2 (50% yield). M+H⁺(532).

EXAMPLE 32

2-{1-Amino-6-chloro-5-[4-(4-fluoro-benzyl)-2R,5S-dimethyl-piperazine-1-carbonyl]-1H-indol-3-yl}-2-oxo-acetamide

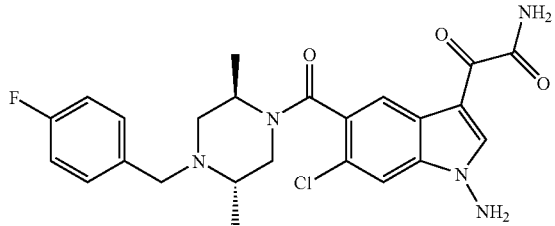

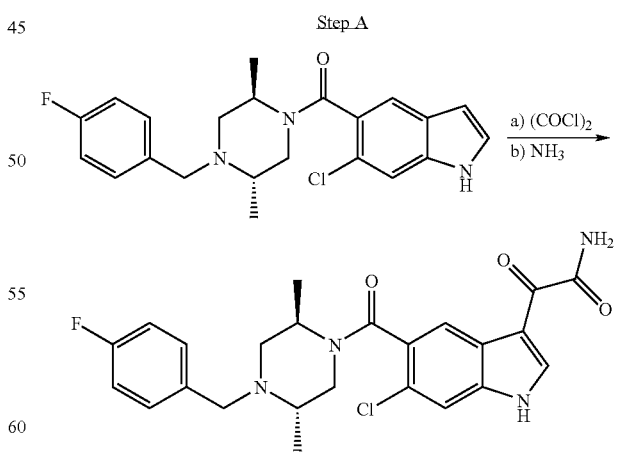

Prepared from (6-Chloro-1H-indol-5-yl)-[4-(4-fluoro-benzyl)-2R,5S-dimethyl-piperazin-1-yl]-methanone as in Example 3, Step G using ammonia in dioxane in place of pyrrolidine. M+H⁺(471).

Step B

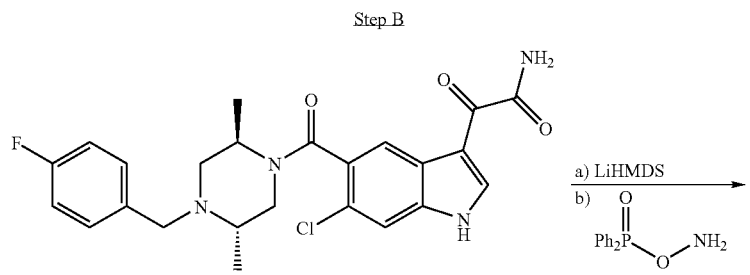

a) LiHMDS
b) Ph₂P(O)-O-NH₂

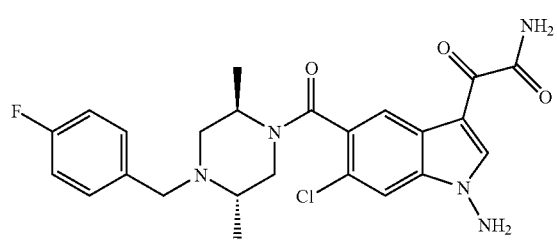

Performed using 2-{6-Chloro-5-[4-(4-fluoro-benzyl)-2R,5S-dimethyl-piperazine-1-carbonyl]-1H-indol-3-yl}-2-oxo-acetamide as in Example 3, Step H (Method 1). M+H⁺(486).

EXAMPLE 33

1-(1-Amino-6-chloro-5-{4-[1-(4-fluoro-phenyl)-ethyl]-2R-methyl-piperazine-1-carbonyl}-1H-indol-3-yl)-2-pyrrolidin-1-yl-ethane-1,2-dione

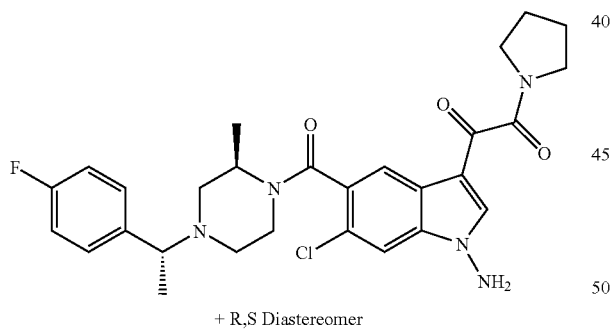

+ R,S Diastereomer

Step A

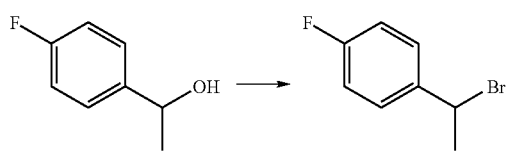

4-Fluoro-α-methylbenzyl alcohol (7 g, 6.3 ml, 50 mmol) was added to 50 mL 48% aqueous solution of HBr at 0° C. The solution was allowed to stir at room temperature three hoursat which time it was extracted with hexane. After drying and concentrated, 10 g of a colorless oil was obtained. M+H⁺ (203).

Step B

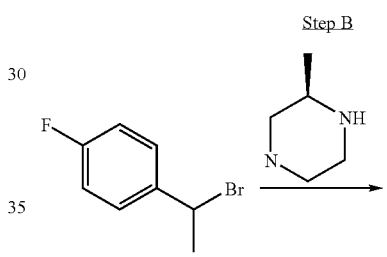

To 6.4 g 1-(4-fluorophenyl)-ethyl bromine in 100 mL DMF was added the piperazine. The mixture was then stirred overnight at room temperature. The solution was evaporated and the residue was then filtrated on a small quantity of silica gel, washing with ethyl acetate and methanol. Purification was carried out using flash chromatography, CHCl₃/MeOH/Et₃N=90/8/2 (or AcOEt/MeOH=90/10). 6.2 g (90%) of pure compound (mixture inseparable of two diasteromers) was obtained. M+H⁺(223).

Step C

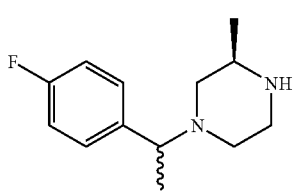

Separation of Diastereomers

To the mixture of two diastereomers (1 g, 4.5 mmol) in methanol (2.5 mL), was added a solution of L-tartaric acid (1.4 g, 9 mmol) in methanol (4.2 mL). Crystallization is effected by keeping the resulting mixture at 0° C. over 30 h. The resulting material was filtered and then 15% NaOH was added to the mother liquid. The free base was extracted with ethyl acetate. Upon concentrated the resulting colorless oil was recrystallized in hexane two or three times until the desired purity is obtained (determined by proton NMR). M+H$^+$(223).

The other diastereomer can be obtained by using D-tartaric acid and following the same procedure.

Step D

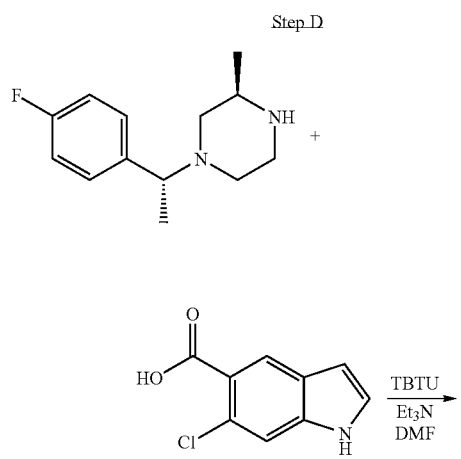

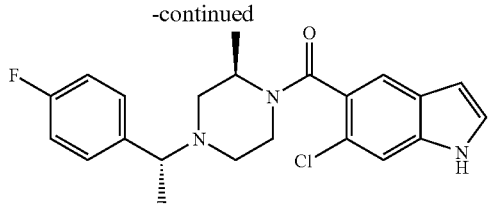

Prepared from 6-methyl-1H-indole-5-carboxylic acid and 1-[1-(4-Fluoro-phenyl)-ethyl]-3R-methyl-piperazine as in Example 3, Step F. M+H$^+$(400).

Step E

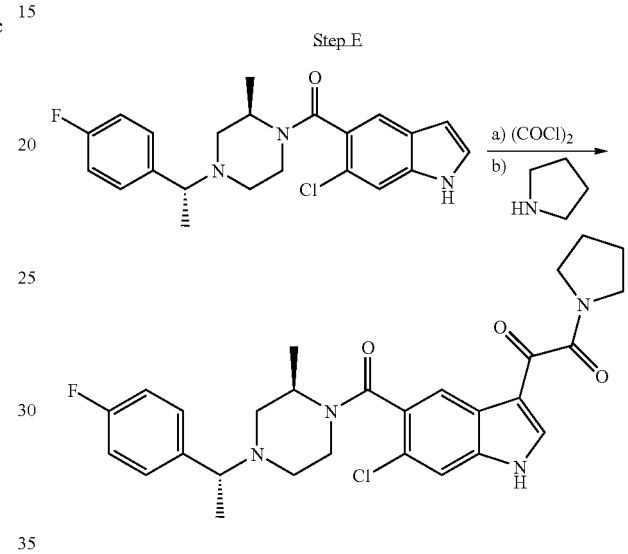

Prepared from (6-Chloro-1H-indol-5-yl)-{4-[1-(4-fluoro-phenyl)-ethyl]-2R-methyl-piperazine-1-yl}-methanone as in Example 3, Step G. M+H$^+$(526).

Step F

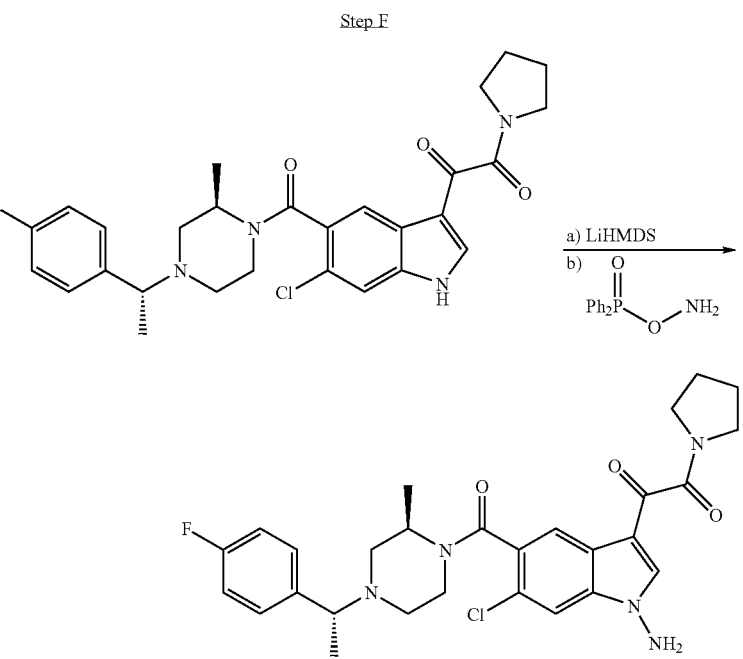

Prepared from 1-(6-Chloro-5-{4-[1-(4-fluoro-phenyl)-ethyl]-2-methyl-piperazine-1-carbonyl}-1H-indol-3-yl)-2-pyrrolidin-1-yl-ethane-1,2-dione as in Example 4, Step C. M+H⁺(541).

The opposite diastereomer is prepared from the piperazine obtained through crystallization with D-tartaric acid and using steps D through F. The racemic material can be obtained by using a 50:50 mixture of piperazine diastereomers.

EXAMPLE 34

2-[1-Amino-5-(4-benzhydryl-2R,5S-dimethyl-piperazine-1-carbonyl)-6-chloro-1H-indol-3-yl]-N,N-dimethyl-2-oxo-acetamide

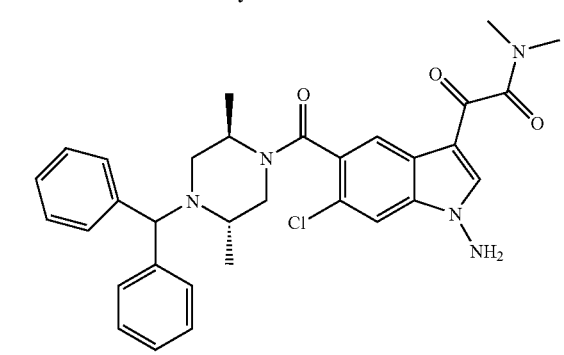

Step A

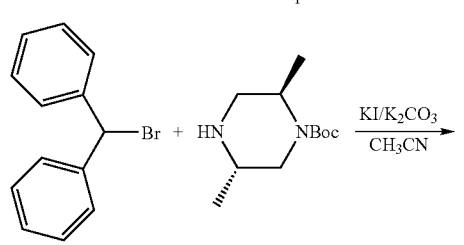

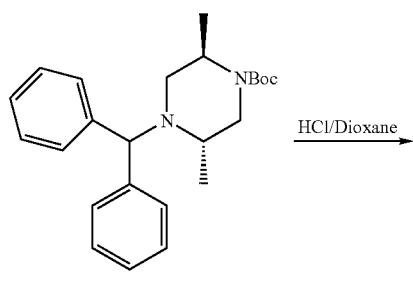

2R,5S-dimethyl-piperazine-1-carboxylic acid tert-butyl ester was dissolved in acetonitrile (600 mL) and potassium iodide (45.2 g, 272 mmol), potassium carbonate (37.7 g, 272 mmol) and α-bromodiphenylmethane (73.9 g, 299 mmol). The mixture was stirred at room temperature overnight and the solvent was removed. The residue was taken up in EtOAc, washed with 5% potassium carbonate, brine, dried over sodium sulfate and concentrated. This material was dissolved in 4 M HCl in dioxane and stirred for 1 h. After removal of the solvent, the residue was dissolved in EtOAc, washed with 10% NaOH, brine, dried over sodium sulfate and concentrated to give crude 1-Benzhydryl-2S,5R-dimethyl-piperazine which was purified using flash chromatography (EtOAc/hexanes) to give 37 g pure 1-Benzhydryl-2S,5R-dimethyl-piperazine. M+H⁺(281).

Step B

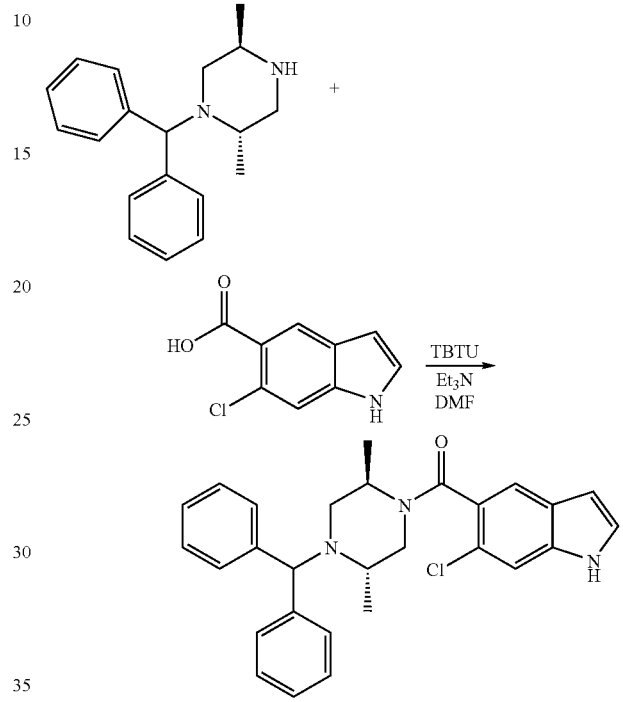

Prepared using 1-Benzhydryl-2S,5R-dimethyl-piperazine and 6-chloroindole-5-carboxylic acid as in Example 3, Step F in 86% yield. M+H⁺(458).

Step C

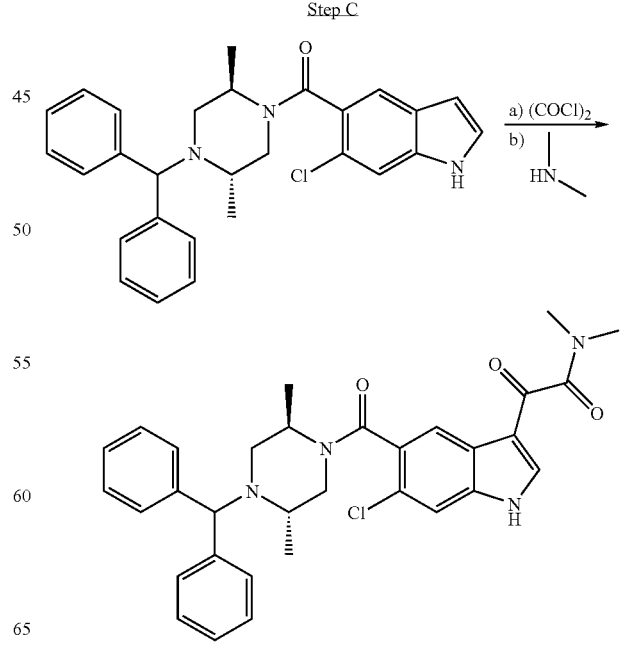

Performed using (4-benzhydryl-2R,5S-dimethyl-piperazin-1-yl)-(6-chloro-1H-indol-5-yl)-methanone and dimethylamine as in Example 3, Step G (89% yield). M+H⁺(558).

Step D

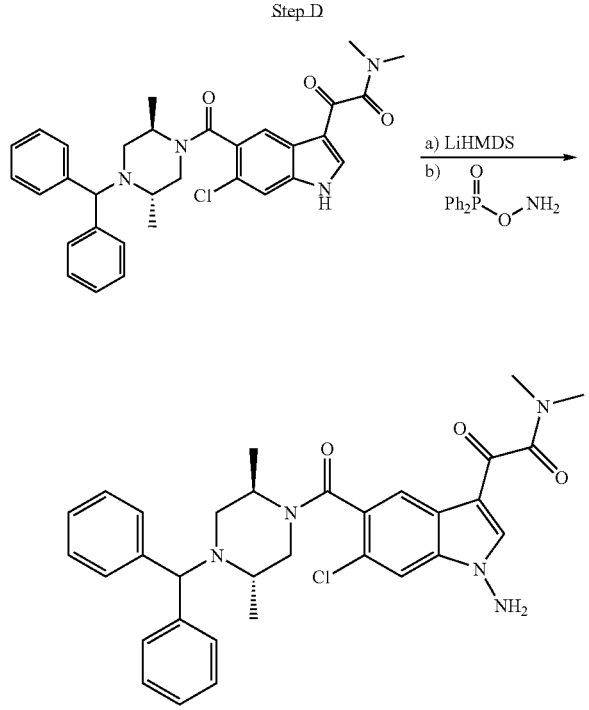

Performed using 2-[5-(4-Benzhydryl-2R,5S-dimethyl-piperazine-1-carbonyl)-6-chloro-1H-indol-3-yl]-N,N-dimethyl-2-oxo-acetamide as in Example 3, Step H (Method 1) (49% yield). M+H⁺(573).

EXAMPLE 35

1-[1-Amino-5-(4-benzhydryl-2R,5S-dimethyl-piperazine-1-carbonyl)-6-chloro-1H-indol-3-yl]-2-pyrrolidin-1-yl-ethane-1,2-dione -continued Step A

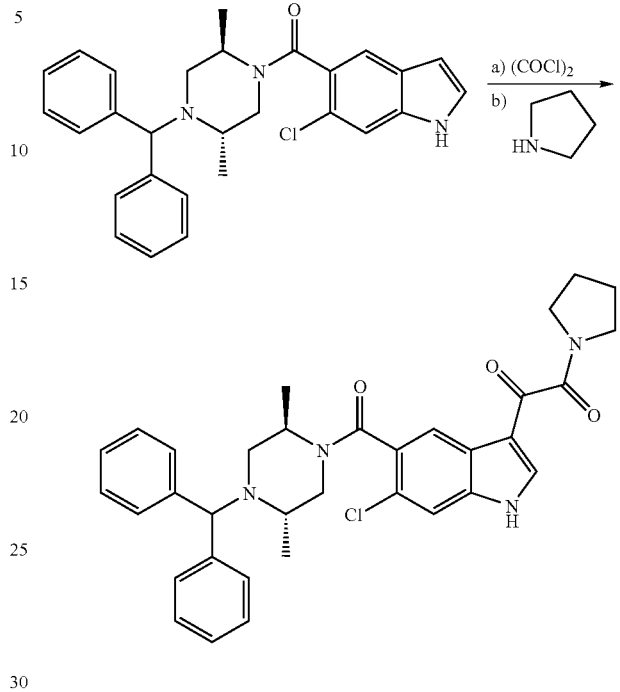

Performed using (4-benzhydryl-2R,5S-dimethyl-piperazin-1-yl)-(6-chloro-1H-indol-5-yl)-methanone as in Example 3, Step G (91% yield). M+H⁺(583).

Step B

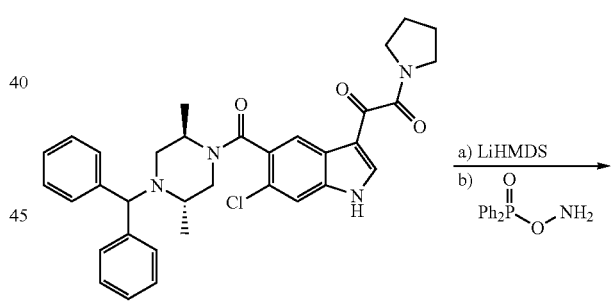

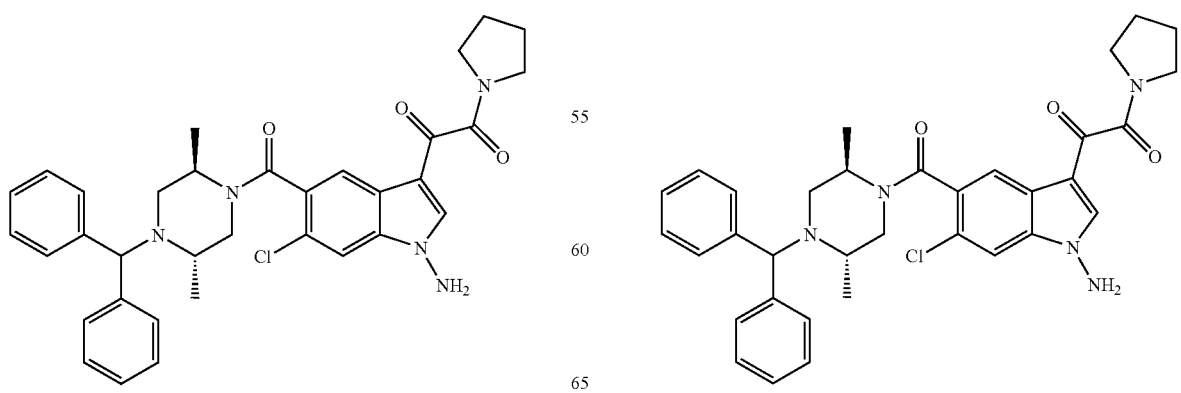

Performed using 1-[5-(4-Benzhydryl-2R,5S-dimethyl-piperazine-1-carbonyl)-6-chloro-1H-indol-3-yl]-2-pyrrolidin-1-yl-ethane-1,2-dione as in Example 3, Step H (Method 1) (67% yield). M+H⁺(599).

EXAMPLE 36

1-[1-Amino-5-(4-benzhydryl-2R,5S-dimethyl-piperazine-1-carbonyl)-6-chloro-1H-indol-3-yl]-2-(R-(+)-3-hydroxy-pyrrolidin-1-yl)-ethane-1,2-dione

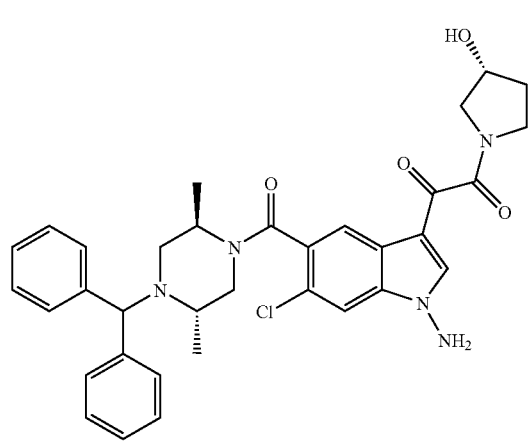

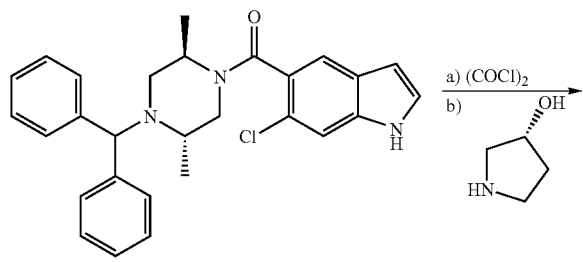

Performed using (4-Benzhydryl-2R,5S-dimethyl-piperazin-1-yl)-(6-chloro-1H-indol-5-yl)-methanone as in Example 3, Step G (63% yield). M+H⁺(599).

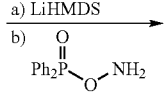

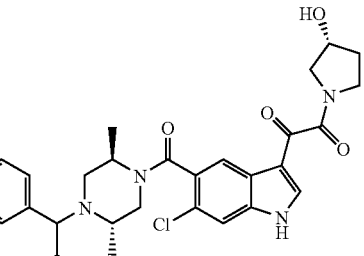

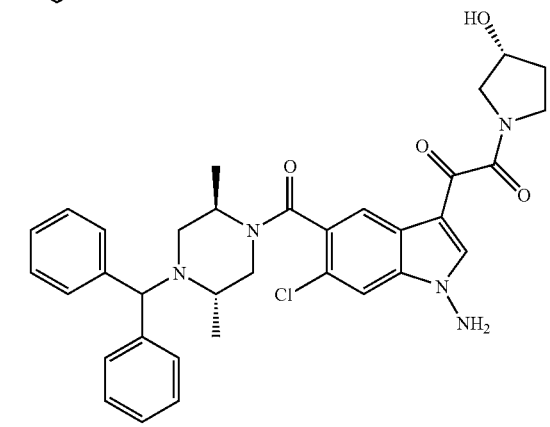

Performed using 1-[5-(4-Benzhydryl-2R,5S-dimethyl-piperazine-1-carbonyl)-6-chloro-1H-indol-3-yl]-2-(R-(+)-3-hydroxy-pyrrolidin-1-yl)-ethane-1,2-dione as in Example 3, Step H (Method 1) (63% yield). M+H⁺(614).

EXAMPLE 37

1-[1-Amino-5-(4-benzhydryl-2R-methyl-piperazine-1-carbonyl)-6-chloro-1H-indol-3-yl]-2-(R-(+)-3-hydroxy-pyrrolidin-1-yl)-ethane-1,2-dione

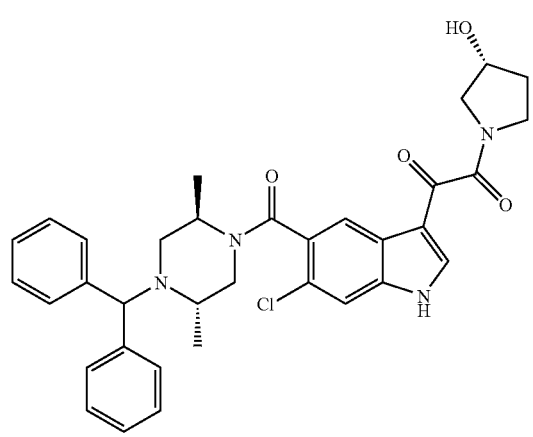

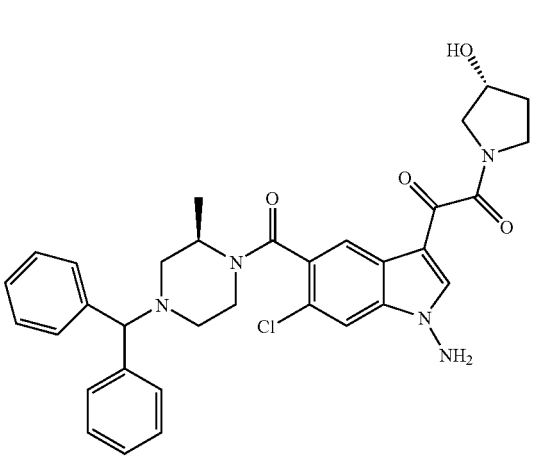

-continued

Step A

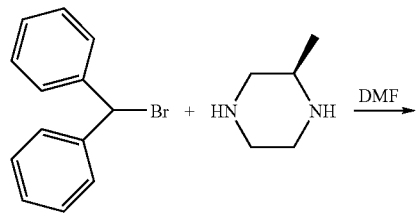

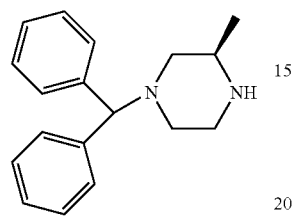

α-Bromodiphenylmethane (1.23 g, 4.99 mmol) was added to a solution of [R]-2-methylpiperazine (500 mg, 4.99 mmol) in DMF (20 mL) and stirred overnight. EtOAc and 15% NaOH were added and the layers were separated. The EtOAc layer was washed with 15% NaOH, brine, dried over sodium sulfate and concentrated. The residue was purified via radial chromatography (EtOAc/hexanes) to give 565 mg 1-benzhydryl-5R-methyl-piperazine. M+H$^+$(267).

Step B

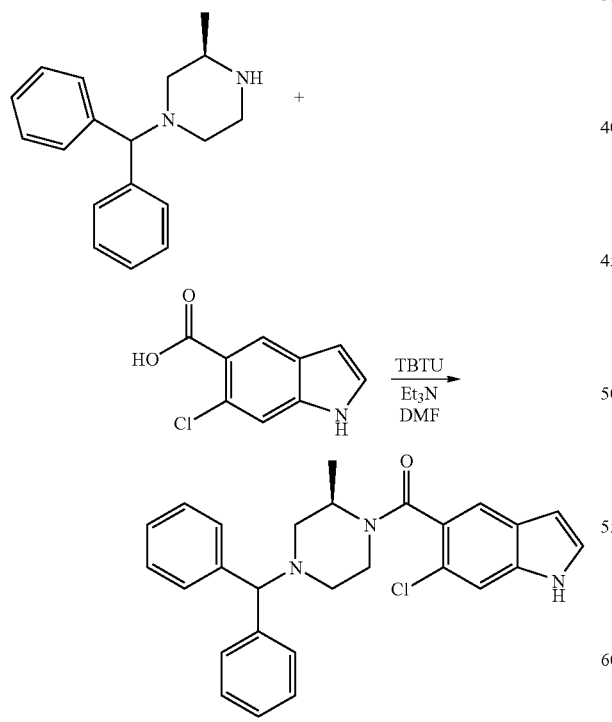

Prepared using 1-benzhydryl-5R-methyl-piperazine and 6-chloroindole-5-carboxylic acid as in Example 3, Step F in 95% yield. M+H$^+$(444).

Step C

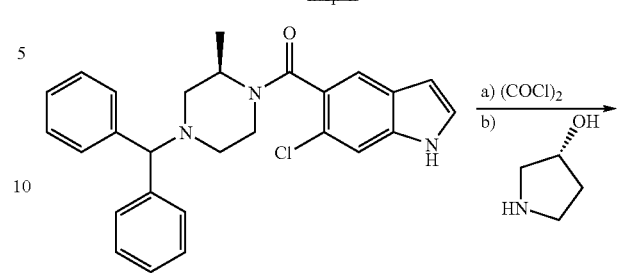

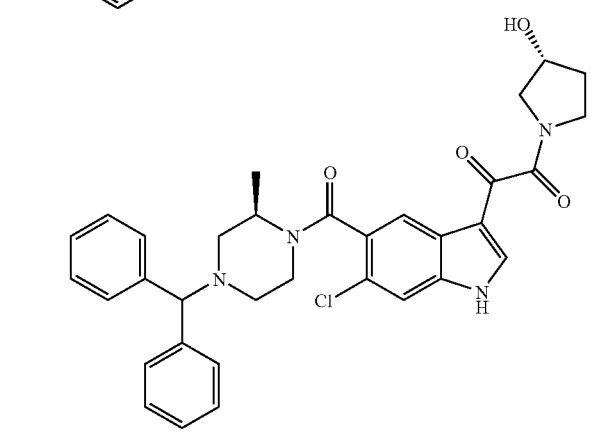

Performed using (4-benzhydryl-2R-methyl-piperazin-1-yl)-(6-chloro-1H-indol-5-yl)-methanone as in Example 3, Step G (93% yield). M+H$^+$(585).

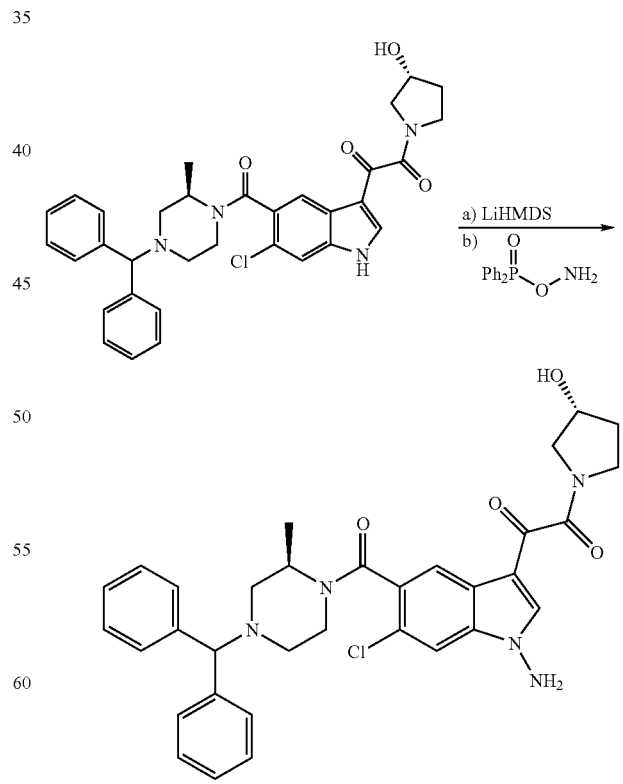

Performed using 1-[5-(4-Benzhydryl-2R-methyl-piperazine-1-carbonyl)-6-chloro-1H-indol-3-yl]-2-(R-(+)-3-hydroxy-pyrrolidin-1-yl)-ethane-1,2-dione as in Example 3, Step H (Method 1) (73% yield). M+H⁺(600).

EXAMPLE 38

1-[1-Amino-5-(4-benzhydryl-2R-methyl-piperazine-1-carbonyl)-6-chloro-1H-indol-3-yl]-2-pyrrolidin-1-yl-ethane-1,2-dione

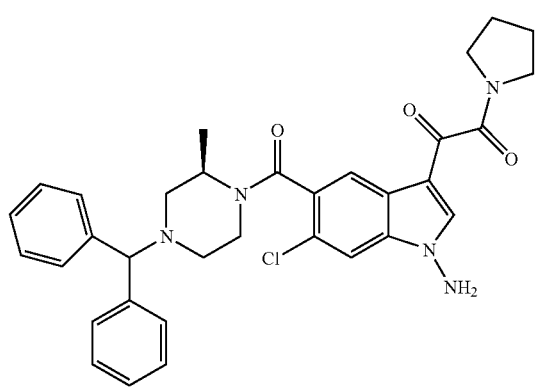

Step A

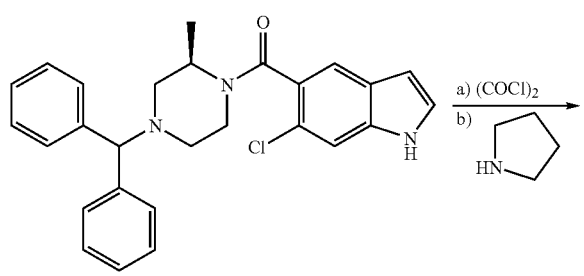

Performed using (4-Benzhydryl-2R-methyl-piperazin-1-yl)-(6-chloro-1H-indol-5-yl)-methanone as in Example 3, Step G (96% yield). M+H⁺(569).

Step B

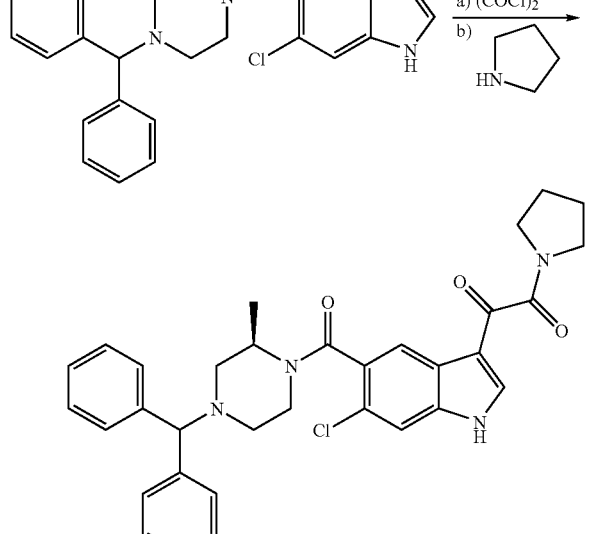

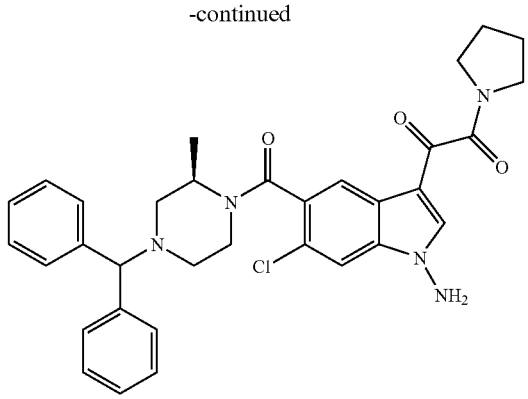

Performed using 1-[5-(4-Benzhydryl-2R-methyl-piperazine-1-carbonyl)-6-chloro-1H-indol-3-yl]-2-pyrrolidin-1-yl-ethane-1,2-dione as in Example 3, Step G (Method 1) (60% yield). M+H⁺(584).

EXAMPLE 39

2-[1-Amino-5-(4-benzhydryl-2R-methyl-piperazine-1-carbonyl)-6-chloro-1H-indol-3-yl]-N,N-dimethyl-2-oxo-acetamide

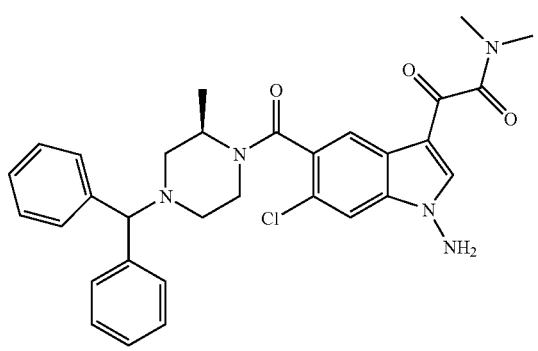

Step A

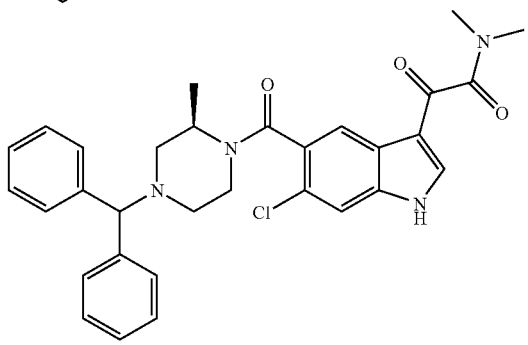

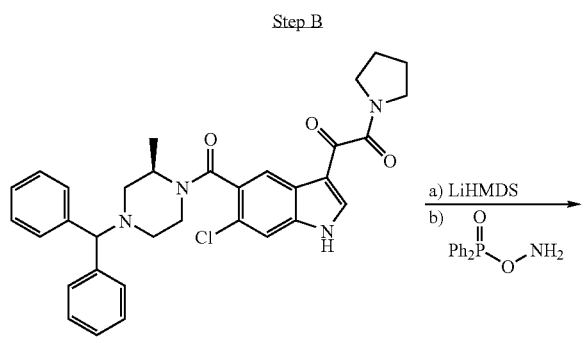

Performed using (4-Benzhydryl-2R-methyl-piperazin-1-yl)-(6-chloro-1H-indol-5-yl)-methanone and dimethyl amine as in Example 3, Step G (69% yield). M+H⁺(543).

EXAMPLE 40

N-Allyl-2-[1-amino-5-(4-benzhydryl-2R-methyl-piperazine-1-carbonyl)-6-chloro-1H-indol-3-yl]-N-methyl-2-oxo-acetamide

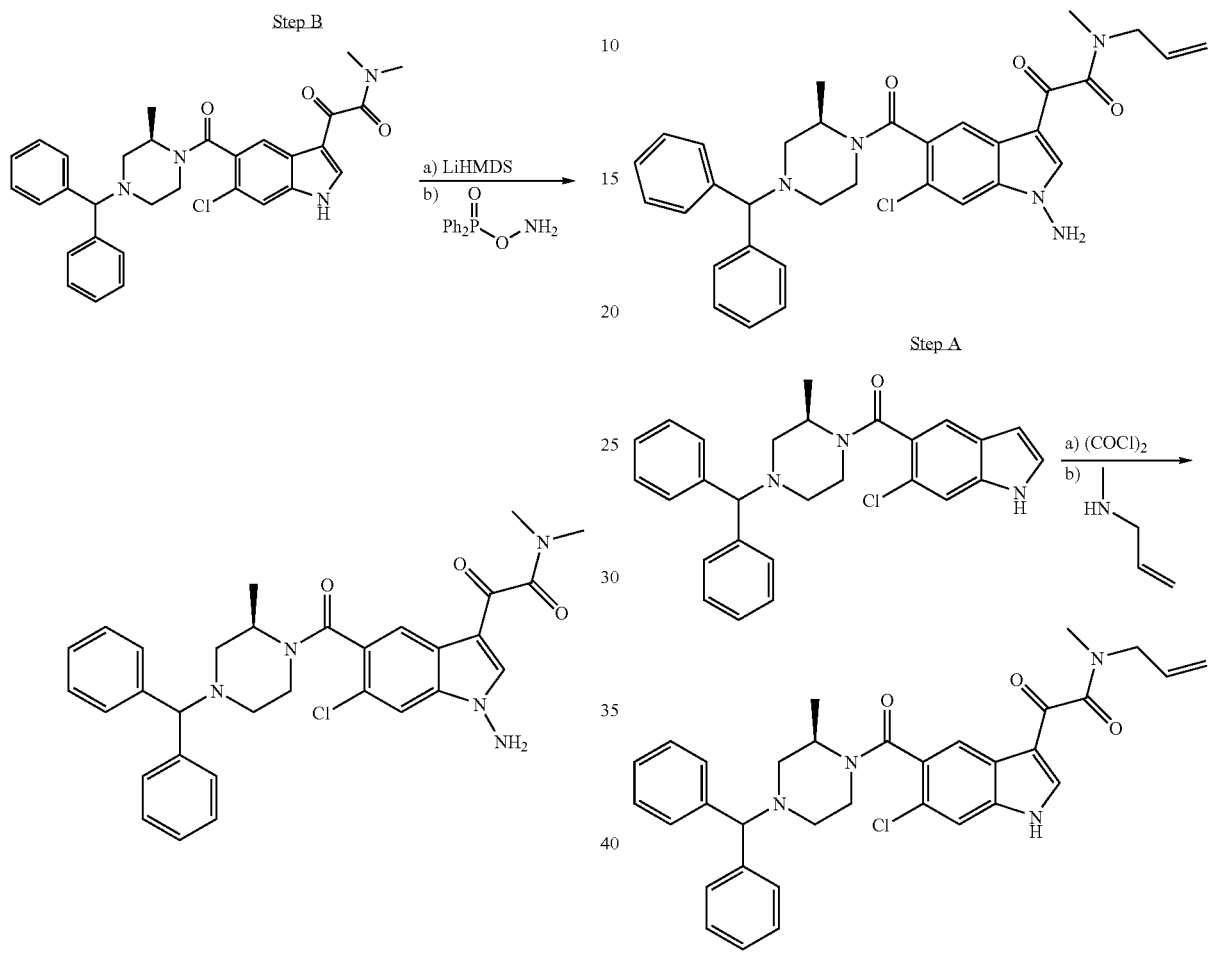

Performed using 2-[5-(4-benzhydryl-2R-methyl-piperazine-1-carbonyl)-6-chloro-1H-indol-3-yl]-N,N-dimethyl-2-oxo-acetamide as in Example 3, Step H (Method 1) (46% yield). M+H⁺(558).

Performed using (4-Benzhydryl-2R-methyl-piperazin-1-yl)-(6-chloro-1H-indol-5-yl)-methanone and N-methylallylamine as in Example 3, Step G (86% yield). M+H⁺(568).

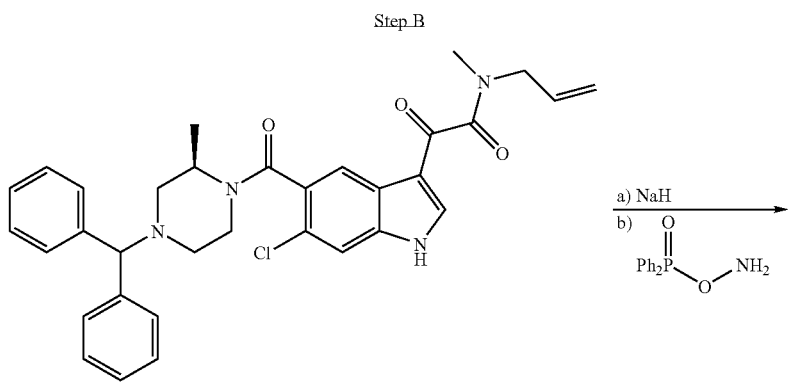

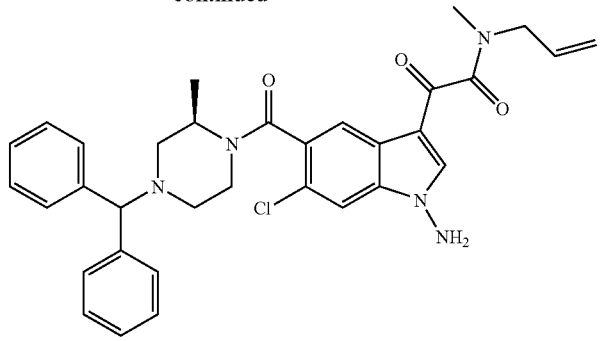

Performed using N-Allyl-2-[5-(4-benzhydryl-2-methyl-piperazine-1-carbonyl)-6-chloro-1H-indol-3-yl]-N-methyl-2-oxo-acetamide as in Example 3, Step H (Method 1) (49% yield). M+H⁺(584).

EXAMPLE 41

2-[1-Amino-6-methoxy-5-(4-thiophen-3-ylmethyl-piperidine-1-carbonyl)-1H-indol-3-yl]-N,N-dimethyl-2-oxo-acetamide

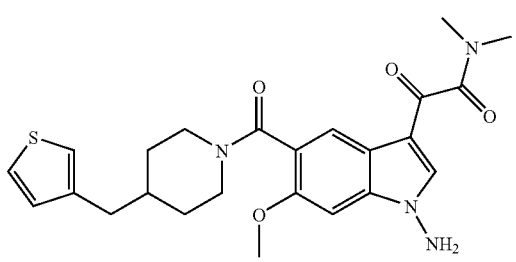

Step A

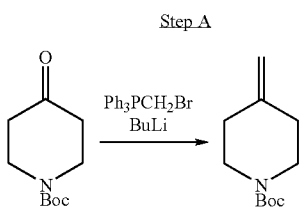

Butyllithium (18.8 mL, 47 mmol) was added to a suspension of methyltriphenyl phosphonium bromide (16.8 g, 60 mmol) in anhydrous ether (100 mL) dropwise at RT. The reaction mixture was stirred for 2 h at RT. Then Boc-piperidone (8 g, 50 mmol) in ether (30 mL) was added to the reaction mixture dropwise. A white suspension was formed during addition. The reaction mixture was continually stirred for 2 h and then filtered off the solid. The filtrate was washed with water, brine, dried and concentrated. The residue was purified by chromatography on silica gel eluting with EtOAc:hexane (1:9) to give 7.2 g (72%) of the desired product. M+H⁺(198).

Step B

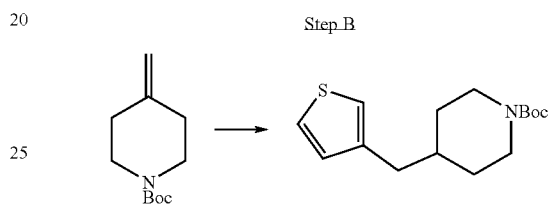

9-BBN (10 mL, 5.1 mmol, 0.5 M in THF) was added to a solution of 4-Methylene-piperidine-1-carboxylic acid tert-butyl ester (1 g, 5.1 mmol) in anhydrous THF (5 mL). The reaction mixture was refluxed for 1 h. Then a mixture of 2-thiophene bromide (759 mg, 4.66 mmol), 1,1'-bis(diphenylphosphino)ferocenepalladium (II) dichloride, dichloromethane (125 mg, 0.15 mmol), and potassium carbonate (952 mg) in water (1 mL) and DMF (10 mL) was added, The reaction mixture was heated at 60° C. for 3 h. The reaction mixture was treated with water, extracted with EtOAc. The combined organic layer was washed with water and brine, dried and concentrated. The residue was purified by chromatography on silica gel eluting with EtOAc:hexane (1:9) to give 600 mg (42%) of the desired product. M+H⁺ (281).

Step C

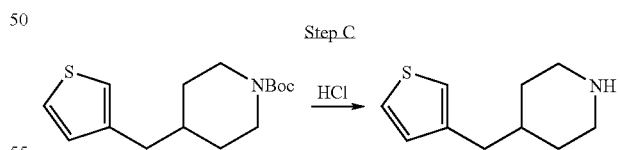

HCl (5 mL, 4 M in dioxane) was added to a solution of 4-thiophen-3-ylmethyl-piperidine-1-carboxylic acid tert-butyl ester (600 mg, 2.13 mmol). The reaction mixture was stirred overnight. The white precipitate was filtered and washed with ether. The product was dissolved in EtOAc, washed with Na₂CO₃ solution, dried and concentrated. The product (260 mg) obtained in 67% yield was used in the next reaction without further purification. M+H⁺(182).

Step D

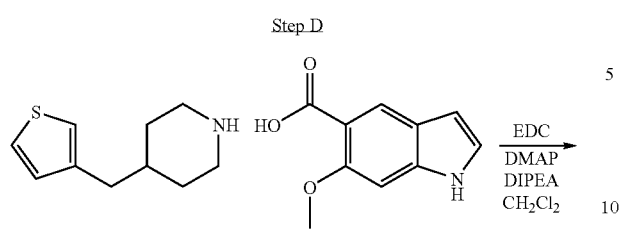

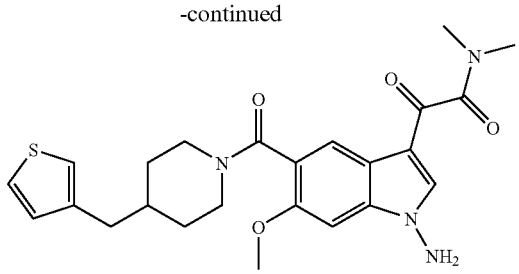

Prepared from 2-[6-Methoxy-5-(4-thiophen-3-ylmethyl-piperidine-1-carbonyl)-1H-indol-3-yl]-N,N-dimethyl-2-oxo-acetamide as in Example 2, Step C. M+H⁺(469).

EXAMPLE 42

1-[1-Amino-6-chloro-5-(2R,5S-dimethyl-4-thiophen-3-ylmethyl-piperazine-1-carbonyl)-1H-indol-3-yl]-2-pyrrolidin-1-yl-ethane-1,2-dione

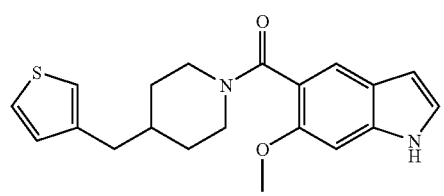

Prepared from 6-methoxyindole-5-carboxylic acid and 4-thiophen-3-ylmethyl-piperidine as in Example 2, Step A. M+H⁺(355).

Step E

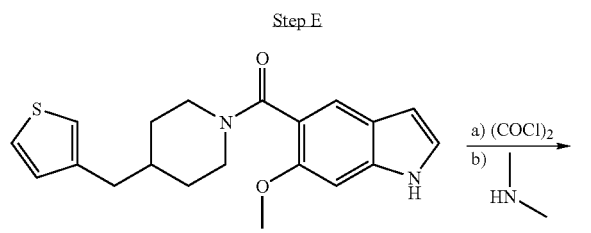

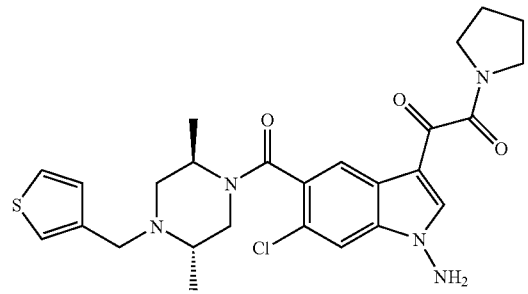

Step A

Prepared from (6-Methoxy-1H-indol-5-yl)-(4-thiophen-3-ylmethyl-piperidin-1-yl)-methanone as in Example 2, Step B. M+H⁺(454).

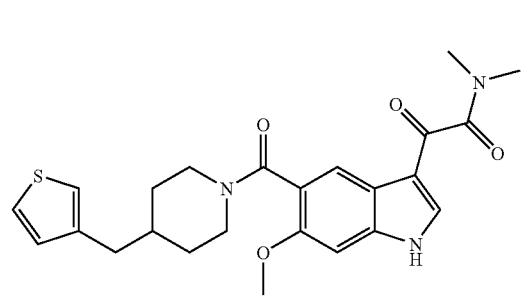

Step F

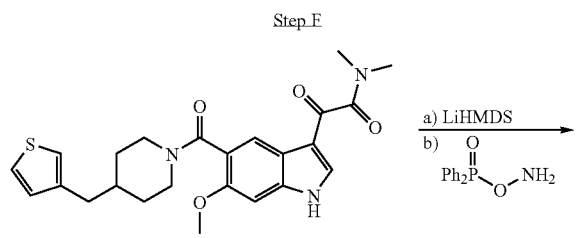

3-Thiophenecarboxaldehyde (1.2 mL, 12 mmol), 2R,5S-dimethyl-piperazine-1-carboxylic acid tert-butyl ester (2.0 g, 10 mmol) and Ti(OiPr)₄ (6 mL, 14.8 mmol) were mixed together and stirred at room temperature overnight. Then the reaction mixture was cooled to 0° C., and a pre-cooled solution of NaCNBH₃ (1.76 g, 28 mmol) in MeOH (12 mL) was added to the reaction mixture. The reaction mixture was allowed to warm up to room temperature and left to stir for 2 h. The reaction mixture was diluted with EtOAc and quenched with a mixture of 60 mL water and 20 mL conc. NH₄OH. The mixture was then left to stir for 1 h. The solution was filtered through Celite and washed with methanol. The methanol was removed under reduced pressure. The resulting product was dissolved in EtOAc, dried with MgSO$_4$ concentrated and purified via chromatography on silica gel with an eluent of ethyl acetate/hexane (2:1). The product was afforded in 97% yield (2.8 g, 9.03 mmol). M+H$^+$(311).

Step B

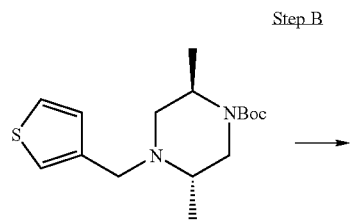

2R,5S-Dimethyl-4-thiophen-3-ylmethyl-piperazine-1-carboxylic acid tert-butyl ester (1.84 g, 6 mmol) was dissolved in 4.0 M HCl in dioxane (20 mL) and stirred for 1 h. The solvent was removed under reduced pressure and diluted with 15% KOH and washed with EtOAc, dried via Na$_2$SO$_4$ and concentrated in vacuo to give the desired product in 87% yield (1.10 g, 5.24 mmol). M+H$^+$(211).

Step C

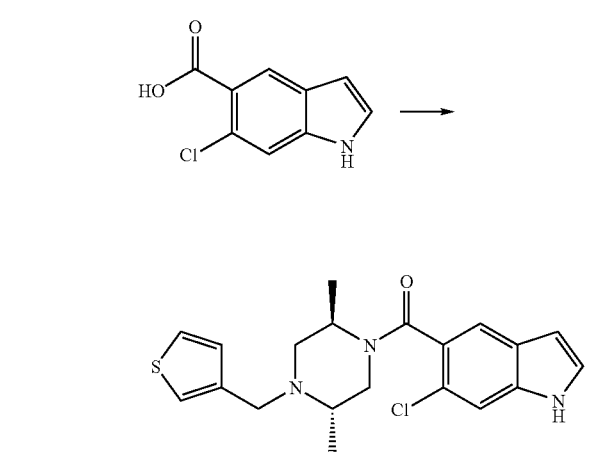

To the suspension of 6-chloroindole-5-carboxylic acid (1 g, 5.12 mmol) in anhydrous DMF (20 mL) under nitrogen atmosphere was added 3-thiophenepiperazine (1.40 g, 6.66 mmol) and TBTU (2 g, 6.14 mmol). The mixture was left to stir at room temperature for 10 min, then triethylamine was added (2.30 mL, 15.36 mmol). The reaction mixture was left to stir at room temperature for 6 h and then the reaction mixture was worked-up by diluting with water (40 mL) and extracting with ethyl acetate (2×40 mL) and dried (Na$_2$SO$_4$), gravity filtered and evaporated. The resultant solid was purified via column chromatography on silica gel eluting with EtOAc/Hexane (1:1) to give 1.8 g (89% yield) of the desired product as a white solid. M+H$^+$(388).

Step D

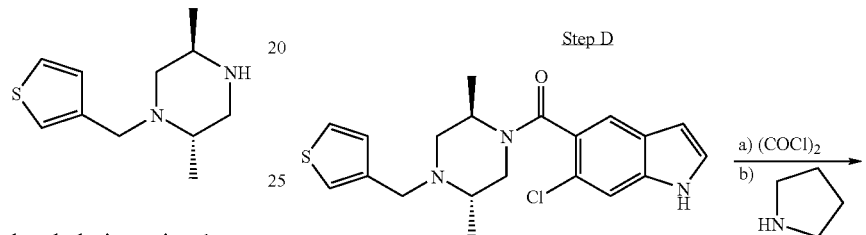

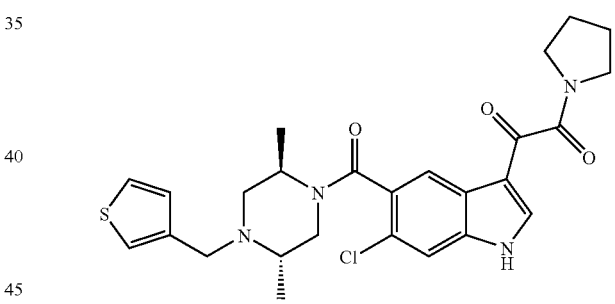

To the suspension of (6-chloro-1H-indol-5-yl)-(2R,5S-dimethyl-4-thiophen-3-ylmethyl-piperazin-1-yl)-methanone (600 mg, 1.55 mmol) in anhydrous DCM (15 mL) was added oxalyl chloride (1.63 mL, 3.85 mmol, 2 M in DCM) dropwise at 0° C. The reaction mixture was stirred at 0° C. for 1 hr, and at room temperature for an additional hour. The solvent and the excess oxalyl chloride was removed under reduced pressure. The yellow solid formed was dried under vacuum and dissolved in anhydrous DCM then cooled in an ice-bath. Pyrrolidine (33 mg, 4.65 mmol) was added. After 30 min, the reaction mixture was treated with water and extracted with DCM. The organic extracts were washed with water, brine, dried and concentrated. The residue was purified via chromatography on silica gel eluting with 2% of MeOH in DCM to give 650 mg (82%) of the desired product as a white solid. M+H$^+$(513).

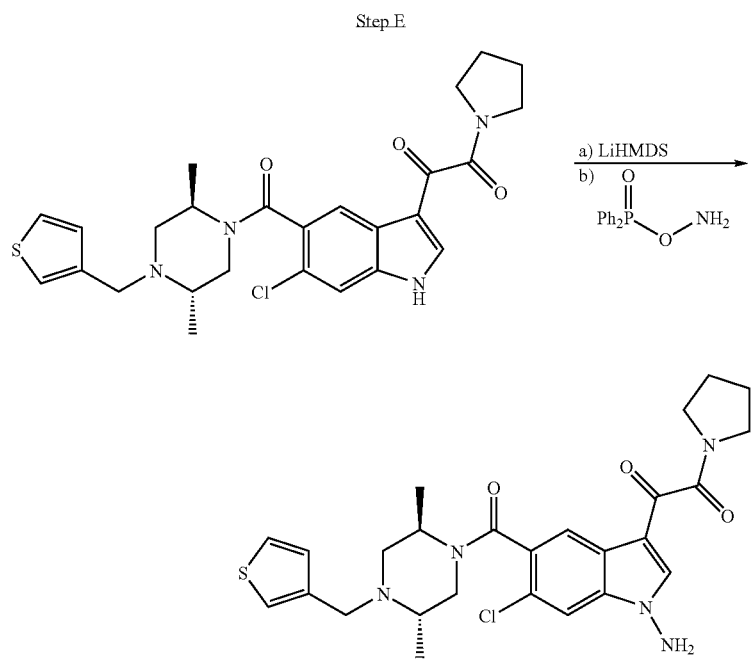

To a solution of 1-[6-Chloro-5-(2R,5S-dimethyl-4-thiophen-3-ylmethyl-piperazine-1-carbonyl)-1H-indol-3-yl]-2-pyrrolidin-1-yl-ethane-1,2-dione (200 mg, 0.40 mmol) in DMF (10 mL) was added lithium bis(trimethylsilyl)amide (1.0 mL, 0.710 mmol, 1.0 M in THF) at 0° C. After 20 min o-(diphenylphosphinyl)hydroxylamine (470 mg, 2.0 mmol) was added to the reaction mixture. After 1 h the reaction mixture was allowed to warm to RT and was left to stir 3 h. The reaction mixture was then quenched with water (10 mL) and extracted with EtOAc, washed with brine, dried with $Na_2SO_4$ and concentrated. The resulting product was purified via prep. HPLC (5% acetonitrile and 95% water with 0.1% TFA buffer). 95 mg (45%) of the free base of the resulting solid was obtained. $M+H^+$(528).

EXAMPLE 43

1-[1-Amino-6-chloro-5-(2S,5R-dimethyl-4-thiophen-3-ylmethyl-piperazine-1-carbonyl)-1H-indol-3-yl]-2-(3-hydroxy-pyrrolidin-1-yl)-ethane-1,2-dione

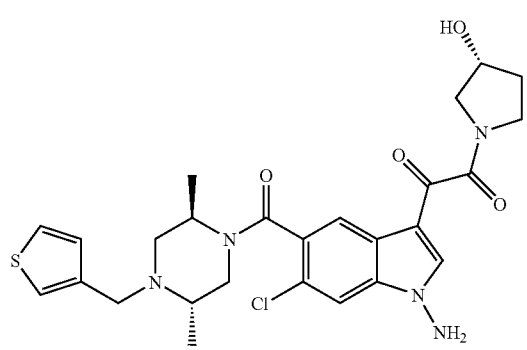

-continued

Step A

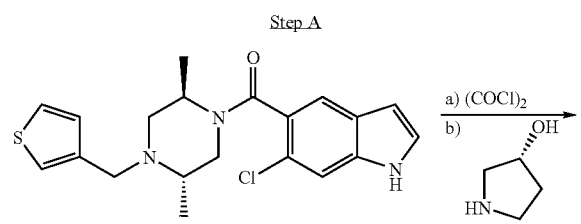

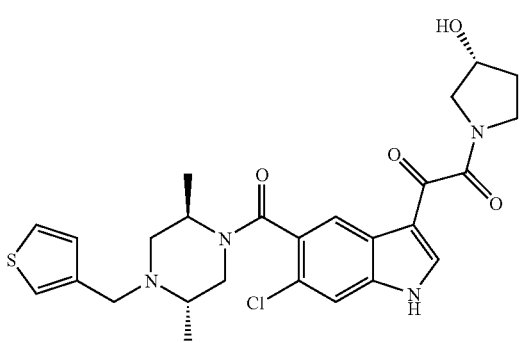

Performed using (6-Chloro-1H-indol-5-yl)-(2R,5S-dimethyl-4-thiophen-3-ylmethyl-piperazin-1-yl)-methanone as in Example 3, Step G (64% yield). $M+H^+$(529).

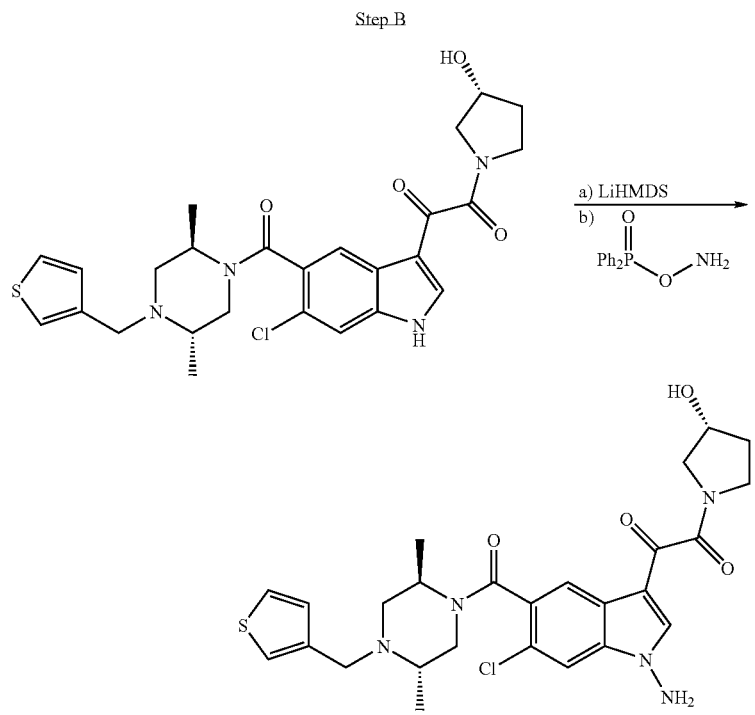

Performed using 1-[6-Chloro-5-(2R,5S-dimethyl-4-thiophen-3-ylmethyl-piperazine-1-carbonyl)-1H-indol-3-yl]-2-(3-hydroxy-pyrrolidin-1-yl)-ethane-1,2-dione as in Example 3, Step H (Method 1) (51% yield). M+H⁺(544).

EXAMPLE 44

2-[1-Amino-6-chloro-5-(2R,5S-dimethyl-4-thiophen-2-ylmethyl-piperazine-1-carbonyl)-1H-indol-3-yl]-N,N-dimethyl-2-oxo-acetamide

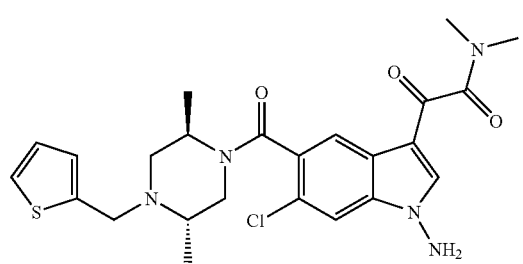

Step A

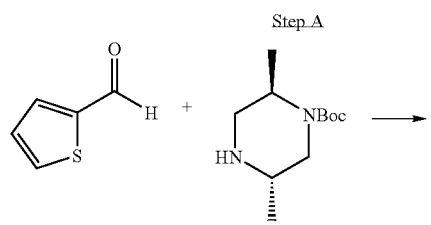

-continued

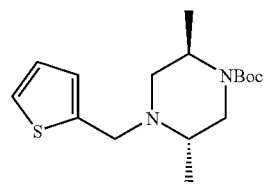

Performed as in Example 42, Step A in 48% yield. M+H⁺ (311).

Step B

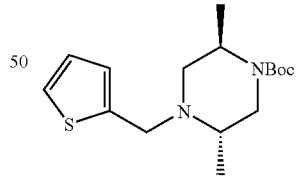

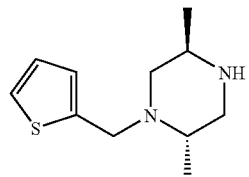

Performed using 2R,5S-Dimethyl-4-thiophen-2-ylmethyl-piperazine-1-carboxylic acid tert-butyl ester as in Example 42, Step B in 89% yield. M+H⁺(211).

Step C
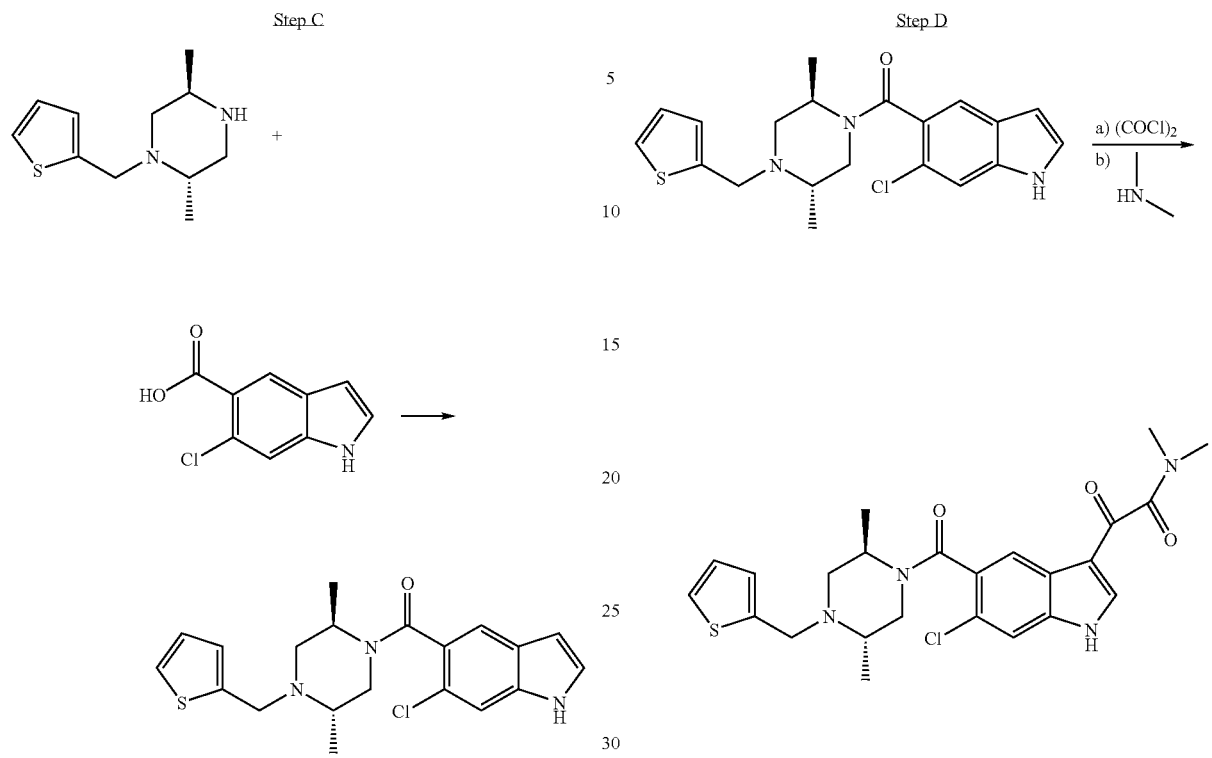
Performed using 2S,5R-Dimethyl-1-thiophen-2-ylmethyl-piperazine and 6-chloroindole-5-carboxylic acid as in Example 42, Step C in 74%. M+H⁺(487).
Step D
Performed using (6-Chloro-1H-indol-5-yl)-(2R,5S-dimethyl-4-thiophen-2-ylmethyl-piperazin-1-yl)-methanone and dimethylamine as in Example 3, Step G (74% yield). M+H⁺(487).
Step E
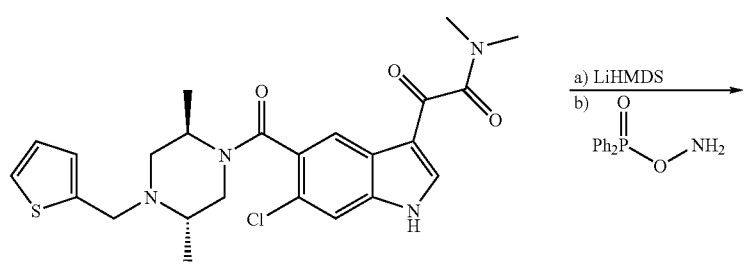
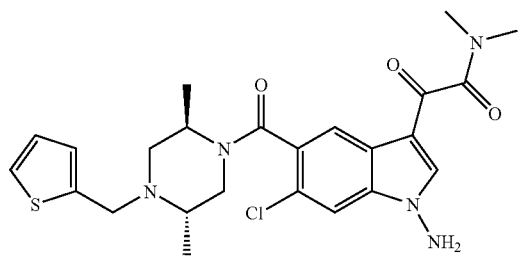

Performed using 2-[6-Chloro-5-(2R,5S-dimethyl-4-thiophen-2-ylmethyl-piperazine-1-carbonyl)-1H-indol-3-yl]-N,N-dimethyl-2-oxo-acetamide as in Example 3, Step H (Method 1) (48% yield). M+H$^+$(502).

EXAMPLE 45

1-[1-Amino-6-chloro-5-(2R,5S-dimethyl-4-thiophen-2-ylmethyl-piperazine-1-carbonyl)-1H-indol-3-yl]-2-pyrrolidin-1-yl-ethane-1,2-dione

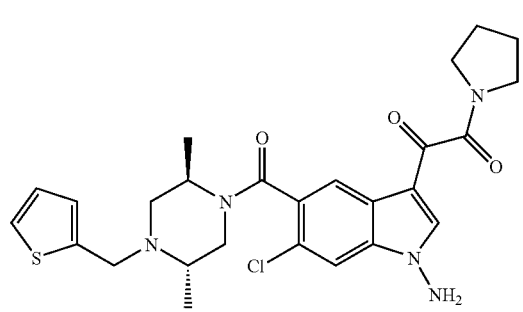

-continued

Step A

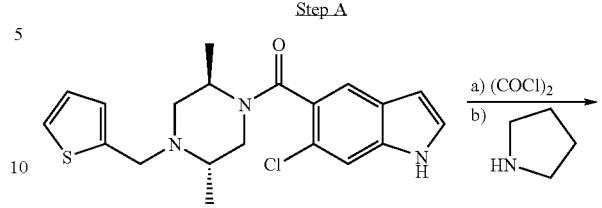

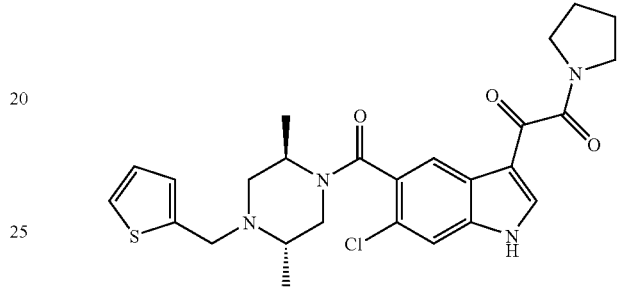

Performed using (6-Chloro-1H-indol-5-yl)-(2R,5S-dimethyl-4-thiophen-2-ylmethyl-piperazin-1-yl)-methanone as in Example 3, Step G. M+H$^+$(513).

Step B

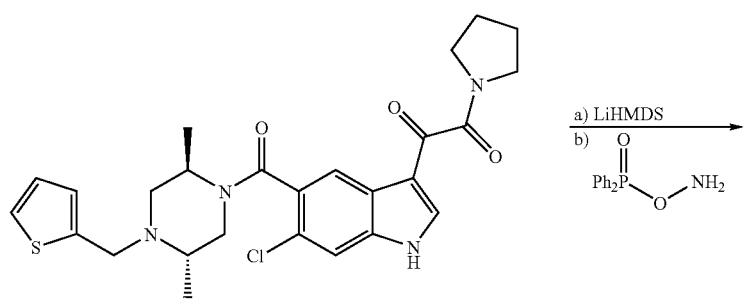

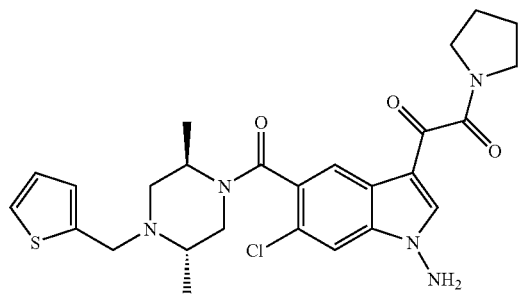

Performed using 1-[6-Chloro-5-(2R,5S-dimethyl-4-thiophen-2-ylmethyl-piperazine-1-carbonyl)-1H-indol-3-yl]-2-pyrrolidin-1-yl-ethane-1,2-dione as in Example 3, Step H (Method 1). M+H$^+$(528).

EXAMPLE 46

1-[1-Amino-6-chloro-5-(2R,5S-dimethyl-4-thiophen-2-ylmethyl-piperazine-1-carbonyl)-1H-indol-3-yl]-2-(R-(+)-3-hydroxy-pyrrolidin-1-yl)-ethane-1,2-dione

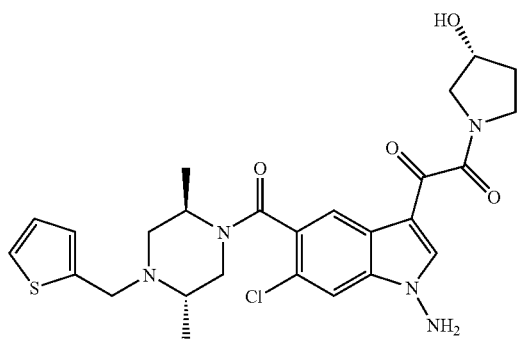

Step A

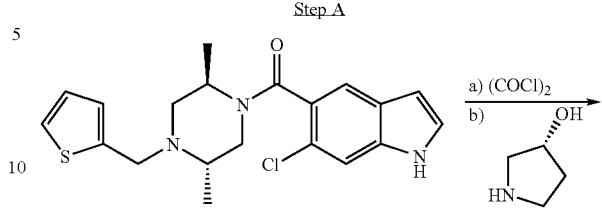

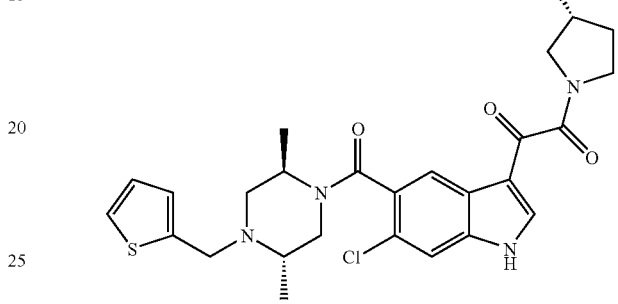

Performed using (6-Chloro-1H-indol-5-yl)-(2R,5S-dimethyl-4-thiophen-2-ylmethyl-piperazin-1-yl)-methanone as in Example 3, Step G. M+H$^+$(529).

Step B

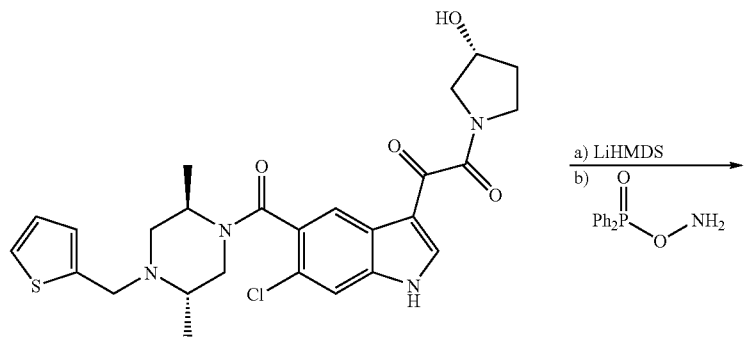

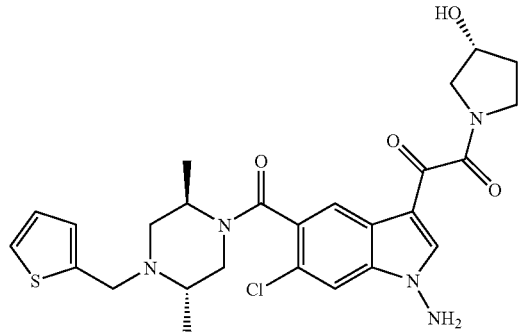

Performed using 1-[6-Chloro-5-(2R,5S-dimethyl-4-thiophen-2-ylmethyl-piperazine-1-carbonyl)-1H-indol-3-yl]-2-(R-(+)-3-hydroxy-pyrrolidin-1-yl)-ethane-1,2-dione as in Example 3, Step H (Method 1). M+H$^+$(544).

EXAMPLE 47

2-{1-Amino-6-chloro-5-[4-(4-fluoro-benzyl)-2R,5S-dimethyl-piperazine-1-carbonyl]-2-methyl-1H-indol-3-yl}-N,N-dimethyl-2-oxo-acetamide

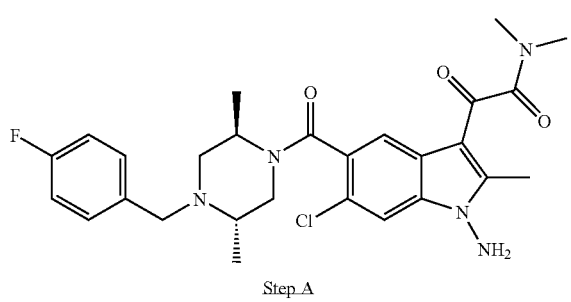

Step A

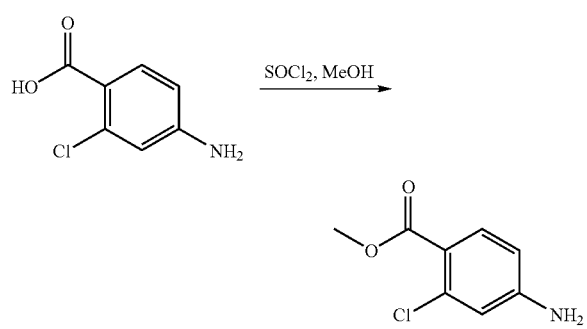

To a 200 mL MeOH solution of 4-amino-2-chlorobenzoic acid (12 g, 67.84 mmol) was added 2 equivalents of SOCl$_2$ (11 mL, 135.7 mmol) at 0° C. The ice-water bath was removed after the addition and the reaction mixture was heated to reflux until the starting material had disappeared, as indicated by LC-MS. After the reaction was cooled back to RT, solvent and excess of SOCl$_2$ were removed under reduced pressure. The residue was suspended in 10% aqueous Na$_2$CO$_3$ solution. The precipitate that formed was filtered and washed with water until the washes became neutral. The filter cake was then re-dissolved in 200 mL of ethyl acetate, and the ethyl acetate layer was washed with water, brine, and dried over anhydrous Na$_2$SO$_4$. After concentrated under reduced pressure and vacuum drying, 12.27 g of product was obtained (97.4%). M+H$^+$(186).

Step B

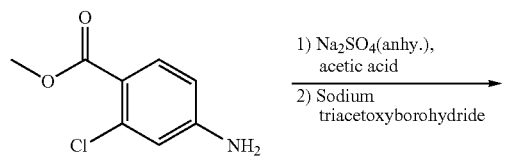

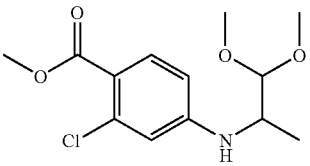

To a solution of 4-amino-2-chloro-benzoic acid methyl ester (12.27 g, 66.11 mmol) and pyruvic aldehyde dimethyl acetal (15.62 g, 132.22 mmol) in 260 mL glacial acetic acid was added anhydrous Na$_2$SO$_4$ (93.9 g, 661.1 mmol). The reaction mixture was stirred at room temperature for 3 hours. Powered sodium triacetoxy borohydride (42 g, 198.33 mmol) was then added in portions for a period of 10 min. Stirring was continued overnight. After the acetic acid was removed under reduced pressure, the remaining residue was made basic by adding a sufficient amount of saturated Na$_2$CO$_3$ solution. The product was then extracted with ethyl acetate. The organic layer was then dried over anhydrous Na$_2$SO$_4$ and concentrated in vacuo. Flash column chromatography separation (30% ethyl acetate/hexane) then afforded 16.5 g product as colorless oil (87%). M+H$^+$(288).

Step C

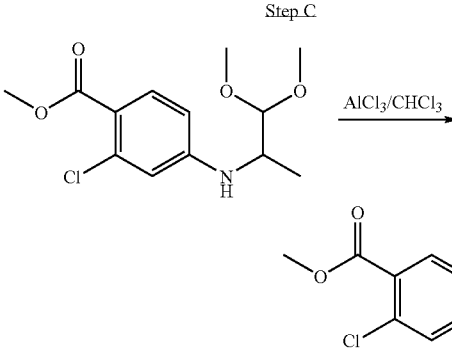

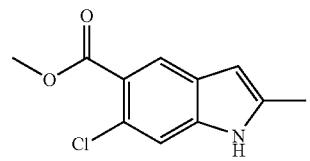

To solution of 2-chloro-4-(2,2-dimethoxy-1-methyl-ethylamino)-benzoic acid methyl ester (7.06 g, 24.55 mmol) in 100 mL anhydrous CHCl$_3$ at 0° C. was added anhydrous AlCl$_3$ (9.8 g, 73.7 mmol) in small portions. The reaction mixture was stirred at 0° C. for 1 h before warming up to room temperature and stirring overnight. Ice-cold water was added carefully to quench the excess of AlCl$_3$ and the organic layer was separated and washed with saturated NaHCO$_3$ solution, water, and brine. The organic layer was then dried over Na$_2$SO$_4$ and concentrated in vacuo. Flash column chromatography separation (10~30% ethyl acetate/hexane) afforded 0.659 g expected product (12%). M+H$^+$(224).

Step D

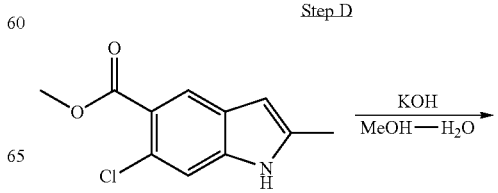

-continued

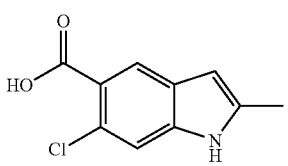

0.56 g of 6-Chloro-2-methyl-1H-indole-5-carboxylic acid methyl ester (2.5 mmol) was dissolved in 15 mL MeOH. To this solution was added 4 eq NaOH in 5 mL of water. The reaction mixture was heated to reflux for 4 hours. The solvent was removed under reduced pressure. The residue was re-dissolved in water and acidified with 10% aqueous HCl. The product was extracted with ethyl acetate. The organic layer was then washed with water, brine, dried over anhydrous $Na_2SO_4$ and concentrated in vacuo. 0.524 g of product was obtained (100%). M+H$^+$(210).

Step E

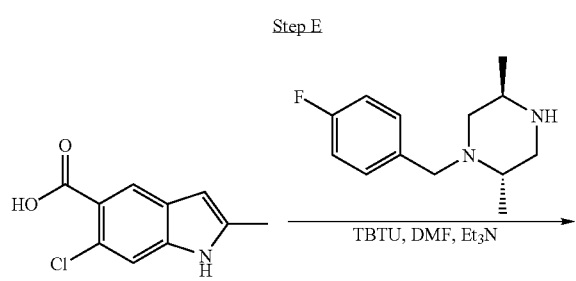

-continued

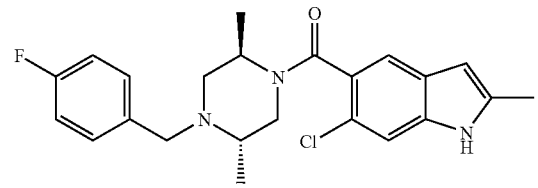

Performed using 1-(4-Fluoro-benzyl)-2S,5R-dimethyl-piperazine and 6-Chloro-2-methyl-1H-indole-5-carboxylic acid as in Example 3, Step F in 76% yield. M+H$^+$(414).

Step F

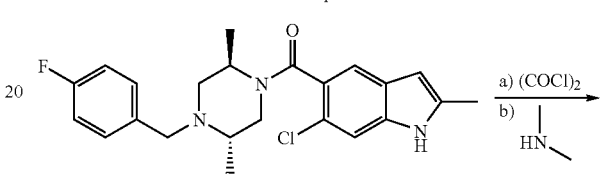

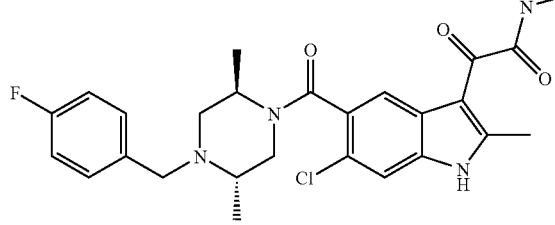

Performed using (6-Chloro-2-methyl-1H-indol-5-yl)-[4-(4-fluoro-benzyl)-2R,5S-dimethyl-piperazin-1-yl]-methanone and dimethylamine as in Example 3, Step G (95% yield). M+H$^+$(529).

Step G

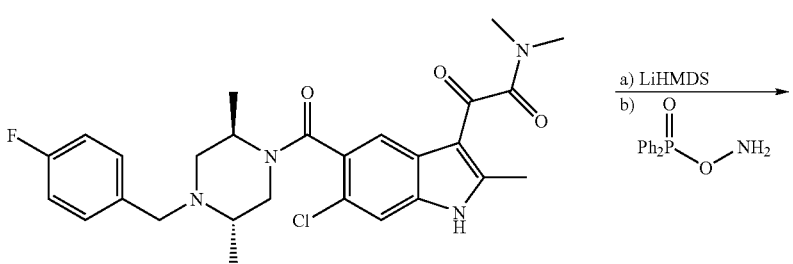

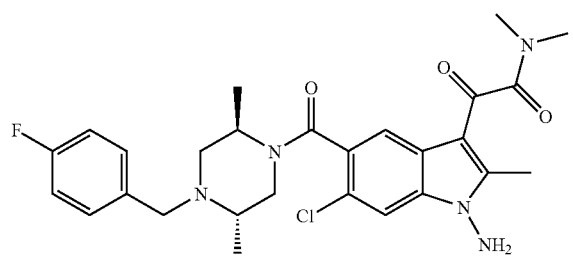

Performed using 2-{6-Chloro-5-[4-(4-fluoro-benzyl)-2R,5S-dimethyl-piperazine-1-carbonyl]-2-methyl-1H-indol-3-yl}-N,N-dimethyl-2-oxo-acetamide as in Example 3, Step H (Method 1) in 97% yield. M+H⁺(529).

EXAMPLE 48

1-{1-Amino-6-chloro-5-[4-(4-fluoro-benzyl)-2R,5S-dimethyl-piperazine-1-carbonyl]-2-methyl-1H-indol-3-yl}-2-pyrrolidin-1-yl-ethane-1,2-dione

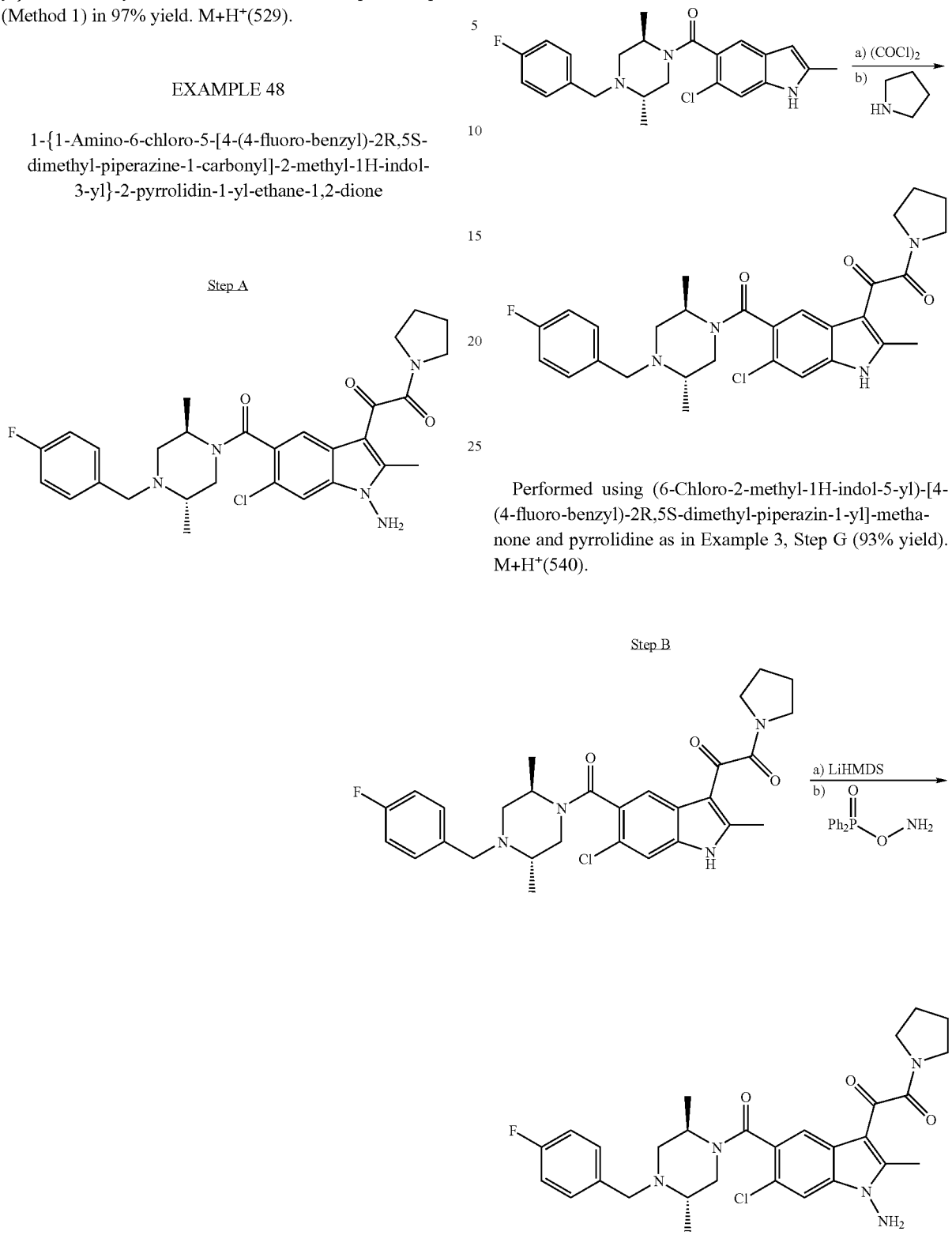

Performed using (6-Chloro-2-methyl-1H-indol-5-yl)-[4-(4-fluoro-benzyl)-2R,5S-dimethyl-piperazin-1-yl]-methanone and pyrrolidine as in Example 3, Step G (93% yield). M+H⁺(540).

Performed using 1-{6-Chloro-5-[4-(4-fluoro-benzyl)-2R, 5S-dimethyl-piperazine-1-carbonyl]-2-methyl-1H-indol-3-yl}-2-pyrrolidin-1-yl-ethane-1,2-dione as in Example 3, Step H (Method 1) in 95% yield. M+H$^+$(555).

EXAMPLE 49

2-{1-Amino-5-[4-(4-fluoro-benzyl)-2R,5S-dimethyl-piperazine-1-carbonyl]-6-methoxy-2-methyl-1H-indol-3-yl}-N,N-dimethyl-2-oxo-acetamide Step A

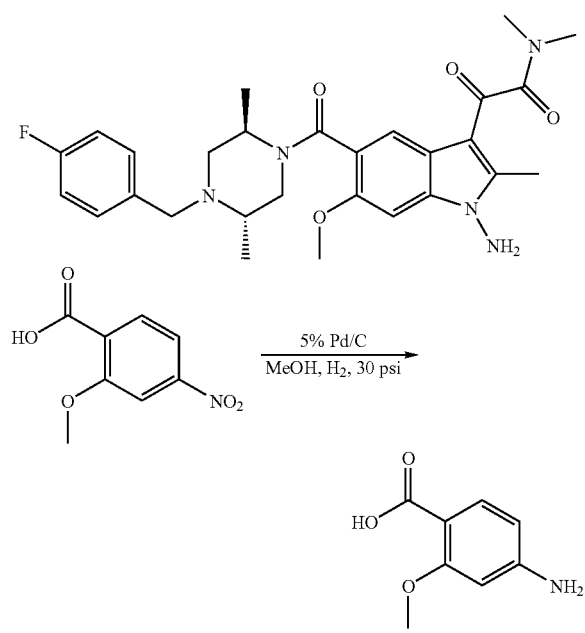

15.2 g of 2-methoxy-4-nitro-benzoic acid (75.6 mmol) was dissolved in 200 mL MeOH. To this solution was added Pd/C (10%, 20 mg/per mmol) under N$_2$ protection. The solution was degassed for 5 min. Hydrogenation under 30 psi H$_2$ was carried out overnight. Palladium catalyst was removed by filtration through Celite. The combined organic solvent was concentrated to dryness and 13 g of product was obtained (100%). M+H$^+$(168).

Step B

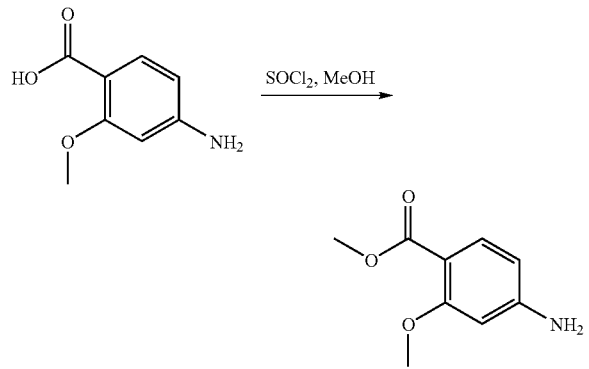

2.9 g of 4-amino-2-methoxy-benzoic acid (77.17 mmol) was dissolved in 200 mL MeOH. At 0° C., to this solution was added 2 eq SOCl$_2$ (12.5 mL, 154.24 mmol) The reaction mixture was heated to reflux temperature overnight. After solvent and excess of SOCl$_2$ were removed under reduced pressure, the residue was suspended in 10% Na$_2$CO$_3$. The precipitate that formed was solution was filtered and filter cake was washed with cold water until the washing became neutral. The product was then dried under vacuum at 50° C. About 12.04 g product was obtained after drying (86%). M+H$^+$(182).

Step C

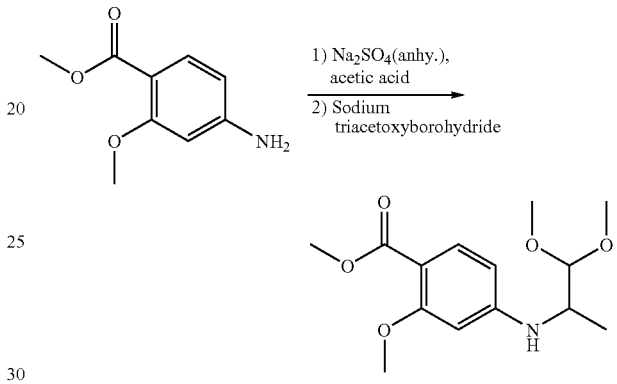

To a solution of 12.04 g 4-amino-2-methoxy-benzoic acid methyl ester (66.45 mmol), Pyruvic aldehyde dimethyl acetal (132.9 mmol) in 460 mL glacial acetic acid was added anhydrous Na$_2$SO$_4$ (94.4 g, 664.5 mmol). The resulting mixture was stirred at room temperature overnight. Powered sodium triacetoxy borohydride (199.35 mmol) was then added in portions for a period of 10 min. The reaction mixture was stirred for another 3 hours. After LC-MS indicated the completion of the starting material, acetic acid was removed under reduced pressure. The residue was made basic by addition of sufficient amount of saturated NaHCO$_3$ solution. The product was then extracted into ethyl acetate layer. The organic layer was dried over anhydrous Na$_2$SO$_4$ and concentrated in vacuo to give 15.6 g of crude product (83%). M+H$^+$ (284).

Step D

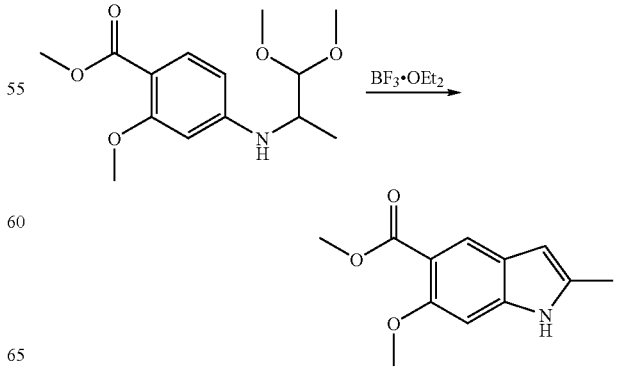

10.03 g of 4-(2,2-dimethoxy-1-methyl-ethylamino)-2-methoxy-benzoic acid methyl ester (35.4 mmol) was dissolved in 120 mL of dry $CH_2Cl_2$. Under $N_2$ protection, to this solution was added 1.7 eq of $BF_3OEt_2$ solution dropwise at 0° C. After the addition, the ice-water bath was removed and the temperature and the mix was warmed up to room temperature and then heated to reflux temperature overnight. Solvent was removed under reduced pressure. The residue was taken up to ethyl acetate and washed with 5% $Na_2SO_4$, $H_2O$, and brine. The organic layer was then dried over anhydrous $Na_2SO_4$ and concentrated in vacuo. Flash column chromatography separation (50% ethyl/hexane) afforded 3.9 g product (50%). M+H$^+$(220).

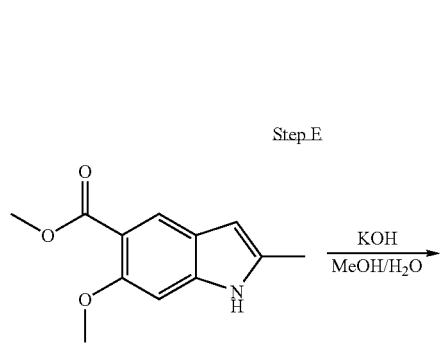

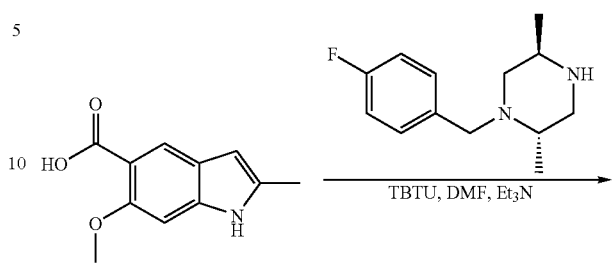

3.89 g of 6-methoxy-2-methyl-1H-indole-5-carboxylic acid methyl ester (17.74 mmol) was dissolved in 30 mL MeOH. To this solution was added 4 eq KOH in 10 mL of water. The reaction mixture was then heated to reflux for 6 hours. Solvent was removed under reduced pressure. And residue was re-dissolved in water and acidified with 10% aqueous HCl. Ethyl acetate was used to extract the product. The organic layer was then washed with water, brine, dried over anhydrous $Na_2SO_4$ and concentrated in vacuo (100%). M+H$^+$(206).

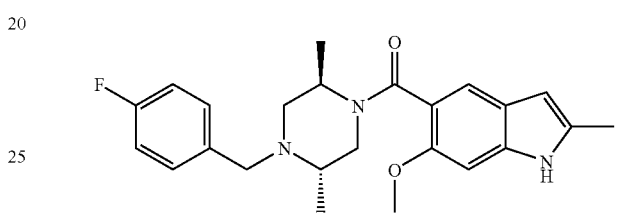

Performed using 1-(4-Fluoro-benzyl)-2S,5R-dimethyl-piperazine and 6-methoxy-2-methyl-1H-indole-5-carboxylic acid as in Example 3, Step F in 83% yield. M+H$^+$(410).

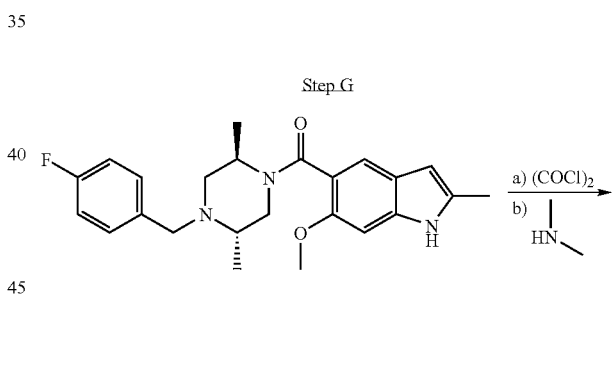

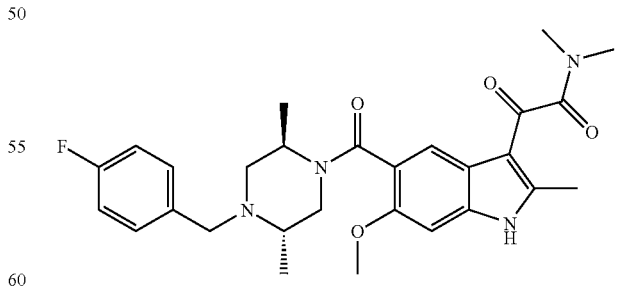

Performed using [4-(4-Fluoro-benzyl)-2R,5S-dimethyl-piperazin-1-yl]-(6-methoxy-2-methyl-1H-indol-5-yl)-methanone and dimethylamine as in Example 3, Step G (98% yield). M+H$^+$(509).

Step H

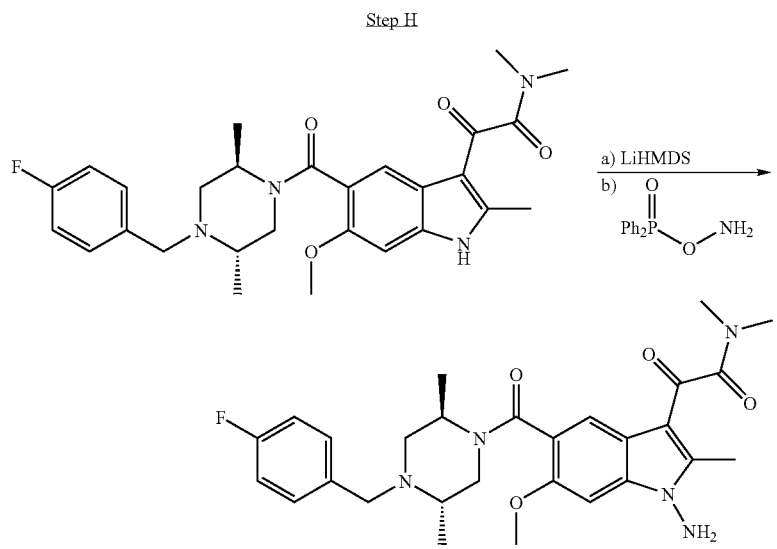

Performed using 2-{5-[4-(4-Fluoro-benzyl)-2R,5S-dimethyl-piperazine-1-carbonyl]-6-methoxy-2-methyl-1H-indol-3-yl}-N,N-dimethyl-2-oxo-acetamide as in Example 3, Step H (Method 1) in 95% yield. M+H⁺(524).

EXAMPLE 50

1-{1-Amino-5-[4-(4-fluoro-benzyl)-2R,5S-dimethyl-piperazine-1-carbonyl]-6-methoxy-2-methyl-1H-indol-3-yl}-2-pyrrolidin-1-yl-ethane-1,2-dione Step A

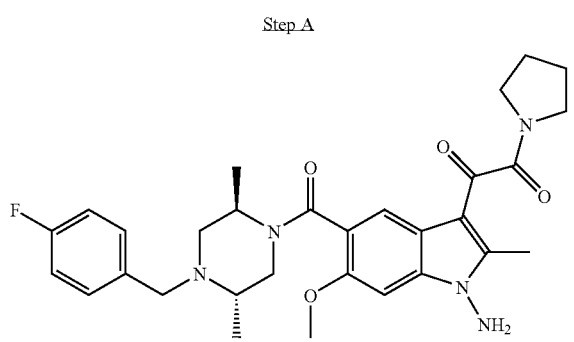

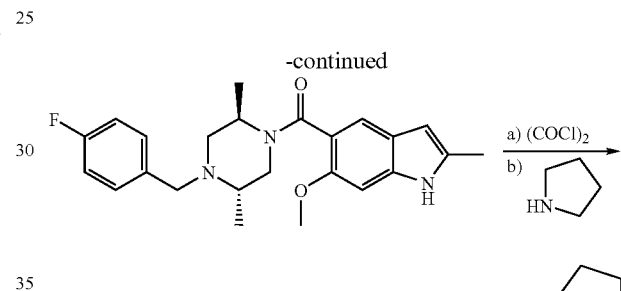

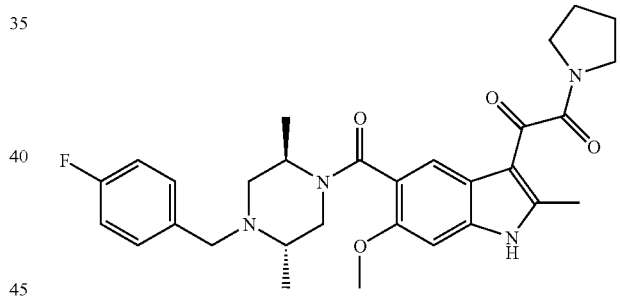

Performed using [4-(4-Fluoro-benzyl)-2R,5S-dimethyl-piperazin-1-yl]-(6-methoxy-2-methyl-1H-indol-5-yl)-methanone and pyrrolidine as in Example 3, Step G (87% yield). M+H⁺(534).

Step B

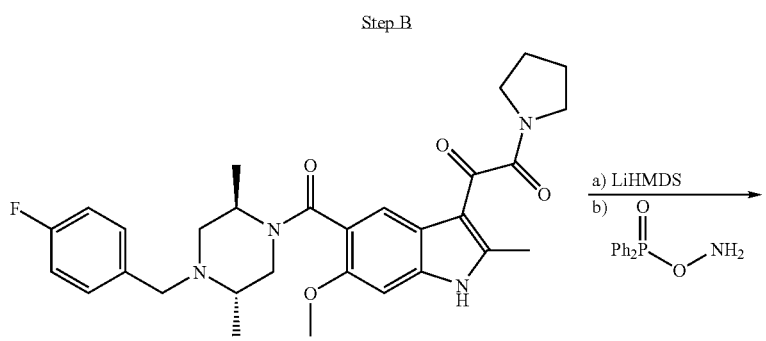

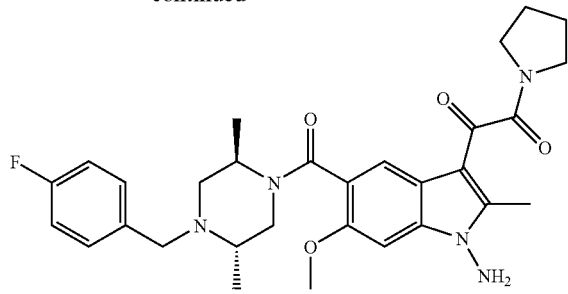

Performed using 1-{5-[4-(4-Fluoro-benzyl)-2R,5S-dimethyl-piperazine-1-carbonyl]-6-methoxy-2-methyl-1H-indol-3-yl}-2-pyrrolidin-1-yl-ethane-1,2-dione as in Example 3, Step H (Method 1) in 96% yield. M+H$^+$(550).

EXAMPLE 51

1-{1-Amino-5-[4-(4-fluoro-benzyl)-2R,5S-dimethyl-piperazine-1-carbonyl]-6-methoxy-2-methyl-1H-indol-3-yl}-2-(R-(+)-3-hydroxy-pyrrolidin-1-yl)-ethane-1,2-dione Step A

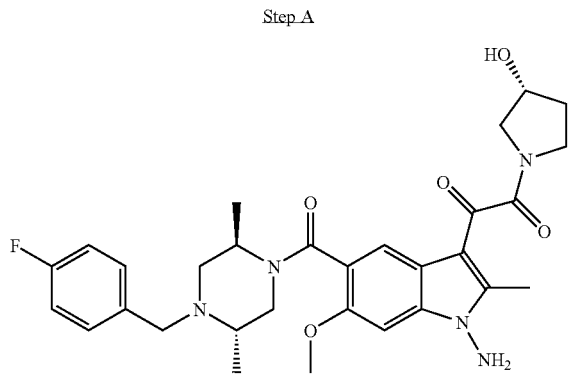

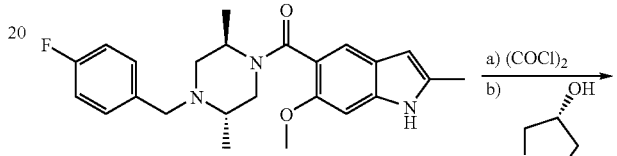

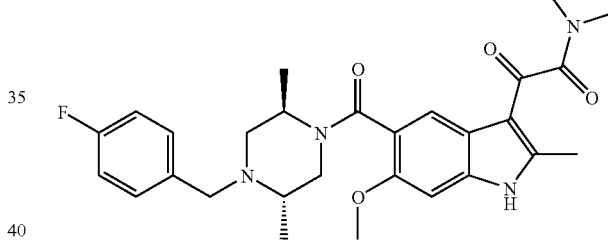

Performed using [4-(4-Fluoro-benzyl)-2R,5S-dimethyl-piperazin-1-yl]-(6-methoxy-2-methyl-1H-indol-5-yl)-methanone and R-(+)-hydroxypyrrolidine as in Example 3, Step G (73% yield). M+H$^+$(551).

Step B

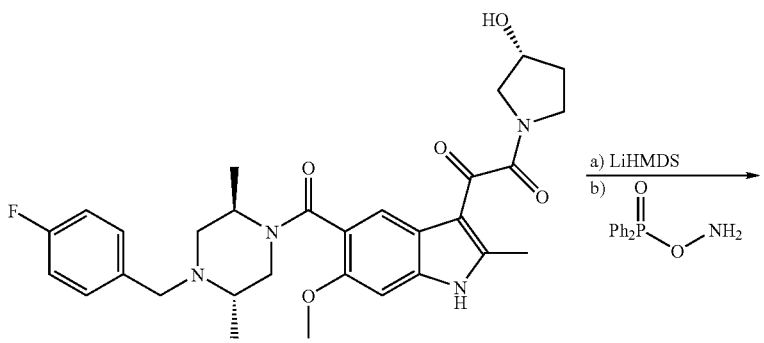

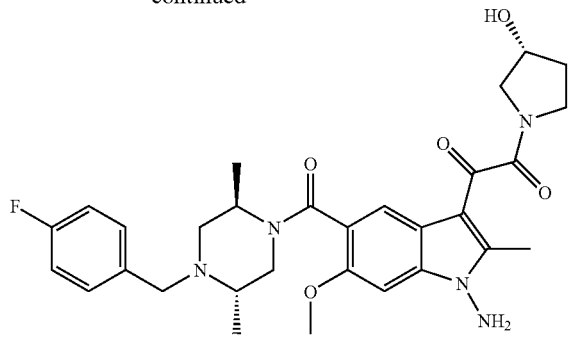

Performed using 1-{5-[4-(4-Fluoro-benzyl)-2R,5S-dimethyl-piperazine-1-carbonyl]-6-methoxy-2-methyl-1H-indol-3-yl}-2-R-(+)-3-hydroxy-pyrrolidin-1-yl)-ethane-1,2-dione as in Example 3, Step H (Method 1) in 65% yield. M+H⁺(566).

EXAMPLE 52

1-[1-Amino-5-(4-benzhydryl-2R,5S-dimethyl-piperazine-1-carbonyl)-6-methoxy-2-methyl-1H-indol-3-yl]-2-pyrrolidin-1-yl-ethane-1,2-dione Step A

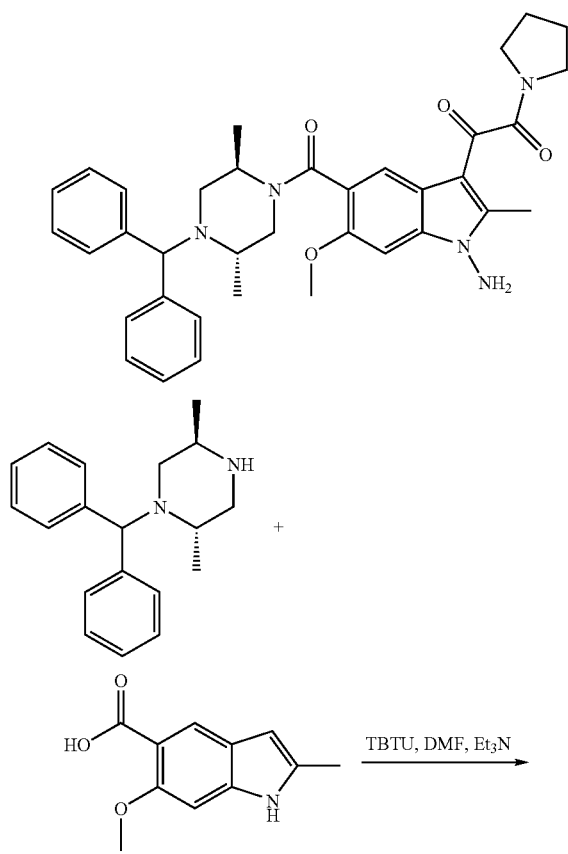

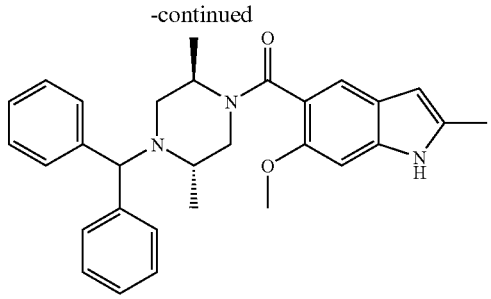

Performed using 1-Benzhydryl-2S,5R-dimethyl-piperazine and 6-methoxy-2-methyl-1H-indole-5-carboxylic acid as in Example 3, Step F in 82% yield. M+H⁺(468).

Step B

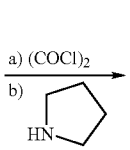

Performed using (4-Benzhydryl-2R,5S-dimethyl-piperazin-1-yl)-(6-methoxy-2-methyl-1H-indol-5-yl)-methanone and pyrrolidine as in Example 3, Step G (94% yield). M+H⁺ (593).

Step C

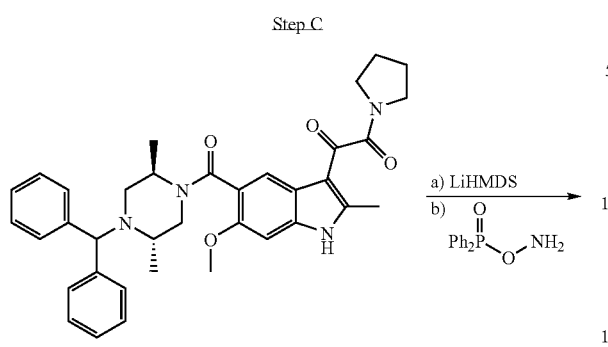

Performed using 1-[5-(4-Benzhydryl-2R,5S-dimethyl-piperazine-1-carbonyl)-6-methoxy-2-methyl-1H-indol-3-yl]-2-pyrrolidin-1-yl-ethane-1,2-dione as in Example 3, Step H (Method 1) in 97% yield. M+H⁺(608).

EXAMPLE 53

Preparation of 2-{1-Acetylamino-5-[4-(4-fluoro-benzyl)-piperidine-1-carbonyl]-6-methoxy-1H-indol-3-yl}-N,N-dimethyl-2-oxo-acetamide

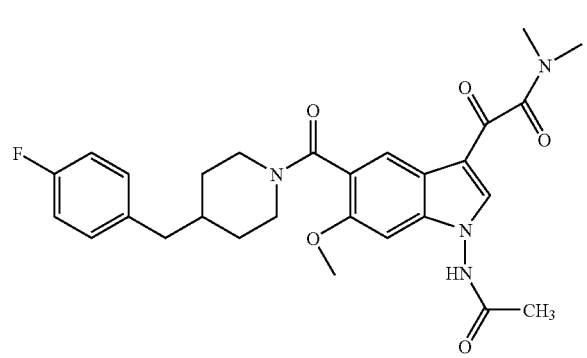

To the suspension of 2-{1-Amino-5-[4-(4-fluoro-benzyl)-piperidine-1-carbonyl]-6-methoxy-1H-indol-3-yl}-N,N-dimethyl-2-oxo-acetamide (100 mg, 0.21 mmol) in anhydrous THF (3 mL) was added pyridine (60 uL, 0.63 mmol) and acetyl chloride (45 uL, 0.63 mmol) at 0° C. The mixture became clear and was stirred continually at RT for 72 h. The reaction mixture was evaporated in vacuo. The crude material was added water and it was extracted with $CH_2Cl_2$. The organic extract was dried ($Na_2SO_4$), filtered, and concentrated. The residue was purified by radial chromatography with 0-3% MeOH/$CHCl_3$ to give 30 mg (28%) of the desired product. M+H⁺ (523).

EXAMPLE 54

2-{1-Amino-5-[4-(4-fluoro-benzyl)-2R,5S-dimethyl-piperazine-1-carbonyl]-6-methoxy-1H-indol-3-yl}-2-oxo-acetamide Step A

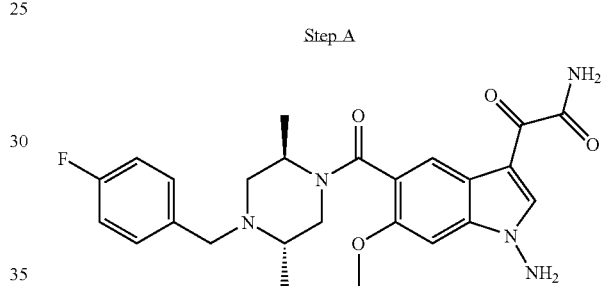

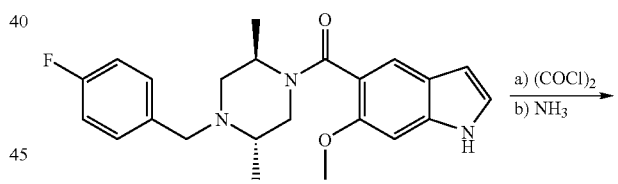

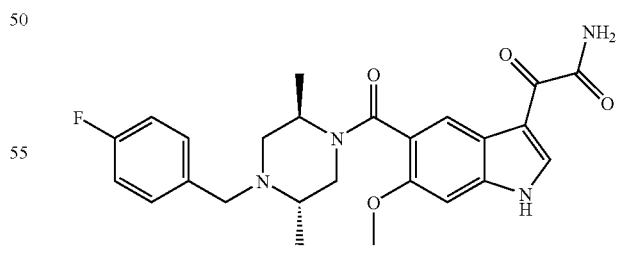

Prepared from [4-(4-fluoro-benzyl)-2R,5S-dimethyl-piperazin-1-yl]-(6-methoxy-1H-indol-5-yl)-methanone as in Example 3, Step G, using ammonia in dioxane in place of pyrolidine M+H⁺(468).

Step B

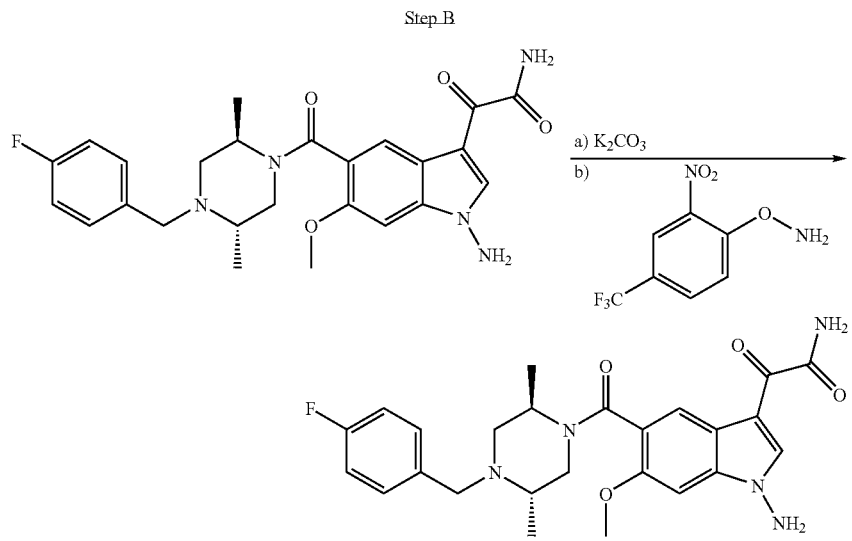

Prepared from 2-{5-[4-(4-Fluoro-benzyl)-2R,5S-dimethyl-piperazine-1-carbonyl]-6-methoxy-1H-indol-3-yl}-2-oxo-acetamide as in Example 3, Step H, method 2 using O-(2-Nitro-4-trifluoromethyl-phenyl)-hydroxylamine as the aminating agent (47% yield). M+H+(483).

EXAMPLE 55

2-{1-Amino-5-[4-(4-fluoro-benzyl)-2R,5S-dimethyl-piperazine-1-carbonyl]-6-methyl-1H-indol-3-yl}-2-oxo-acetamide

Step A

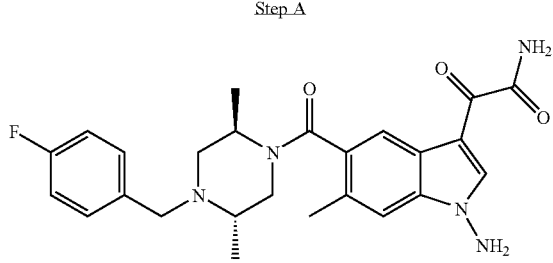

-continued

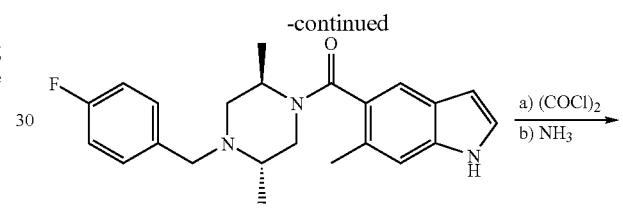

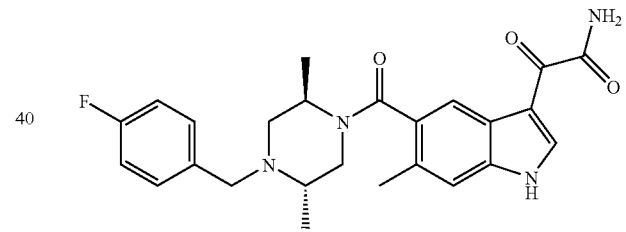

Prepared from [4-(4-Fluoro-benzyl)-2R,5S-dimethyl-piperazin-1-yl]-(6-methyl-1H-indol-5-yl)-methanone as in Example 3, Step G, using ammonia in dioxane in place of pyrolidine M+H+(452).

Step B

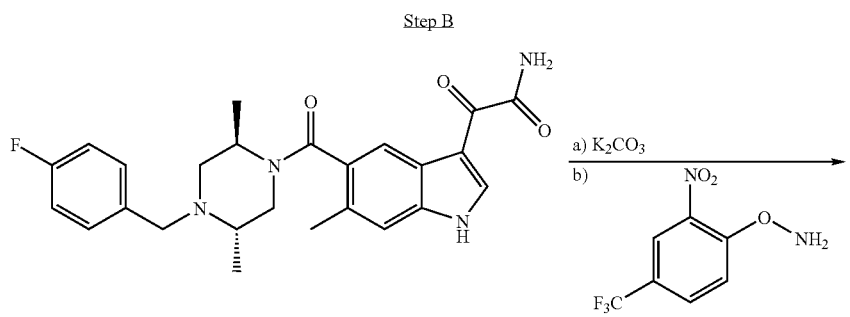

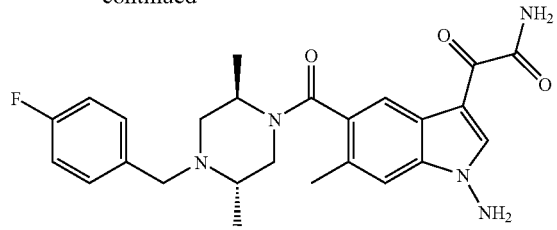

Prepared from 2-{5-[4-(4-Fluoro-benzyl)-2R,5S-dimethyl-piperazine-1-carbonyl]-6-methyl-1H-indol-3-yl}-2-oxo-acetamide as in Example 3, Step H, method 2 using O-(2-Nitro-4-trifluoromethyl-phenyl)-hydroxylamine as the aminating agent (63% yield). M+H$^+$(467).

EXAMPLE 56

2-{1-Amino-5-[4-(4-fluoro-benzyl)-2R,5S-dimethyl-piperazine-1-carbonyl]-6-methyl-1H-indol-3-yl}-N-methyl-2-oxo-acetamide

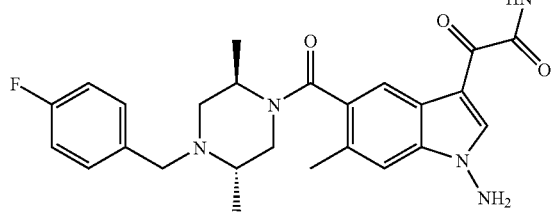

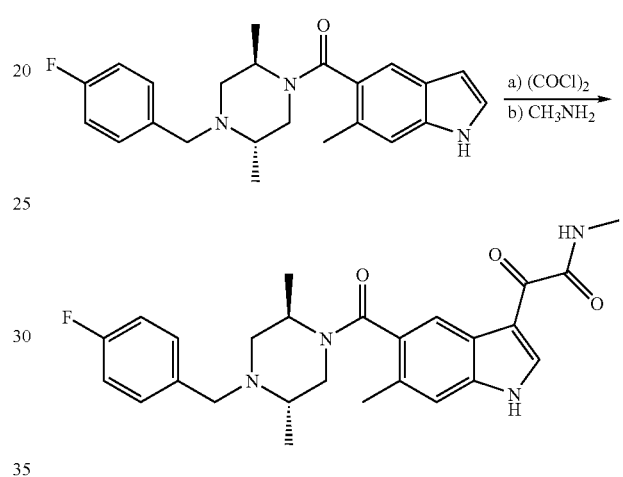

Prepared from [4-(4-Fluoro-benzyl)-2R,5S-dimethyl-piperazin-1-yl]-(6-methyl-1H-indol-5-yl)-methanone as in Example 3, Step G, using methylamine in place of pyrolidine M+H$^+$(466).

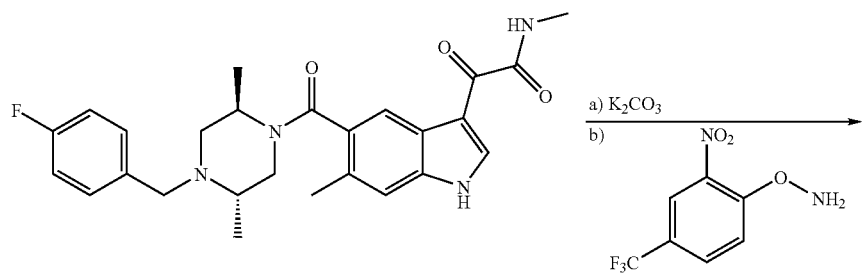

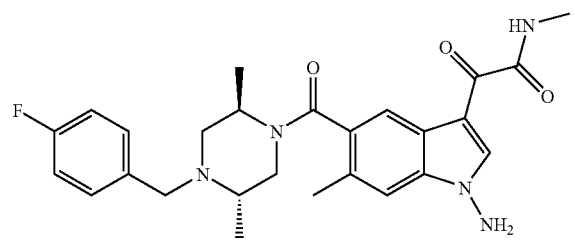

Prepared from 2-{5-[4-(4-Fluoro-benzyl)-2R,5S-dimethyl-piperazine-1carbonyl]-6-methyl-1H-indol-3-yl}-N-methyl-2-oxo-acetamide as in Example 3, Step H, method 2 using O-(2-Nitro-4-trifluoromethyl-phenyl)-hydroxylamine as the aminating agent (67% yield). M+H⁺(481).

The compounds were prepared and many were tested for their ability to inhibit p38-α kinase. It was found that the compounds disclosed in the examples provided herein typically have $IC_{50}$ values for inhibition of p38-α in the range of 1.5 µM or less.

EXAMPLE 57

Synthesis of
2-nitro-4-(trifluoromethyl)phenylhydroxylamine

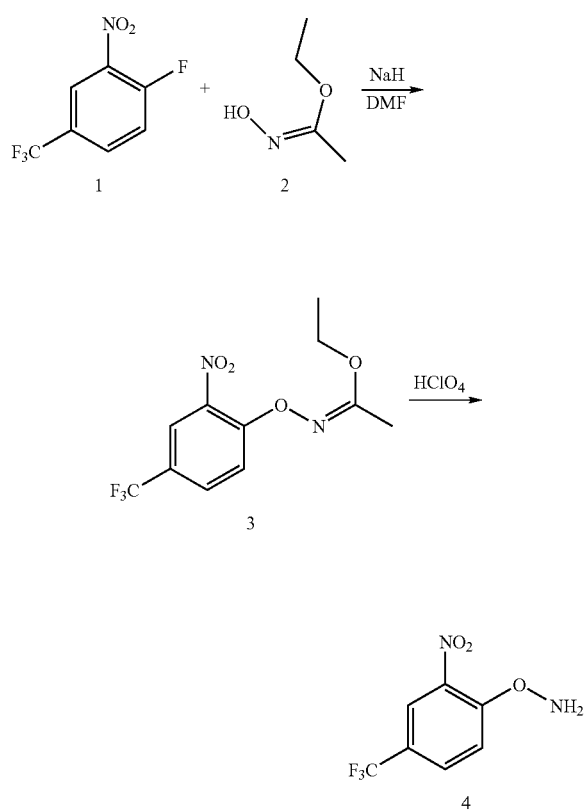

Sodium Hydride 60% dispersion in mineral oil (2.00 g, 49.9 mmol) was added to a stirred solution of ethyl hydroxyacetimidate (2) (4.29 g, 41.6 mmol) in DMF (100 mL) at 0 C under dry nitrogen atmosphere. After stirring at 0 C for 15 minutes, 4-fluoro-2-nitrobenzotrifluoride (1) (8.70 g, 41.6 mmol) was added drop wise. The solution was stirred for an additional hour at 0 C and allowed to slowly warm to room temperature. Ethyl acetate and water were added to quench the reaction. The layers were separated and the organic layer was washed with sat. NaCl solution, dried over sodium sulfate and concentrated. Purification on ISCO chromatography system using ethyl acetate/hexanes gradient gave 10.45 g of 3. NMR (CDCL3) δ s, 1H, 8.3; d, 1H, 7.9; d, 1H, 7.8; q, 2H, 4.2; s, 3H, 2.3; t, 3H, 1.4.

A 70% solution of perchloric acid (20 mL) was added slowly to a stirred solution of 3 (10.45 g, 43.2 mmol) in dioxane (30 mL) at 0 C. The reaction was stirred for an additional 1 hr and ethyl acetate was added. The solution was washed with water, 5% $K_2CO_3$, dried over sodium sulfate and concentrated. Purification on ISCO chromatography system using ethyl acetate/hexanes gradient gave 6.55 g of 4. NMR (CDCL3) δ s, 1H, 8.2; d, 1H, 78.0; d, 1H, 7.8; 3, 2H, 6.3.

EXAMPLE 58

Synthesis of
4-nitro-2-(trifluoromethyl)phenylhydroxylamine

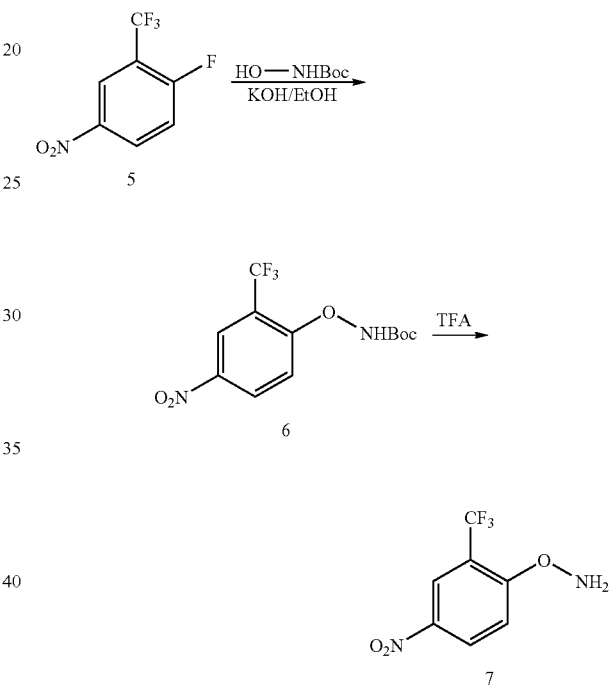

Solid KOH (4.8 g, 86.4 mmol) was added to 60 mL of ethanol and stirred until a clear solution resulted. To this solution was added 3.2 g (24.0 mmol) of Boc-hydroxylamine and the reaction mixture cooled to 0° C. To this reaction mixture, a solution of 5.0 g (30.0 mmol) of 2-fluoro-5-nitrotrifluromethylbenzene in 30 ml ethanol was added dropwise (30 min) and stirred at 0° C. for 3 h. Diluted with water and extracted with ethyl acetate, dried and evaporated to give product 6 as a white solid. ¹H NMR ($CDCl_3$) δ 1.45 (s, 9H), 7.61 (d, 1H), 7.95 (s, 1H), 8.45 (d, 1H), 8.61 (s, 1H).

6 was dissolved in trifluoroacetic acid (30 mL) and the reaction mixture stirred at ambient temperature for 1 h. All starting materials disappeared as monitored by TLC (10% ethylacetate/hexane). trifluoroacetic acid was removed under vacuo. The solids dissolved in ethyl acetate, washed with 10% sodium carbonate, dried and evaporated to give the product as a slightly yellow solid. Recrystallization from 10% hexane in ethyl acetate provided 4.3 g (80%) of phenylhydroxylamine 7 as a white solid. $^1$H NMR (CDCl$_3$) δ 2.25 (s, 2H), 7.42 (d, 1H), 8.41 (d, 1H), 8.51 (s, 1H).

EXAMPLE 59

Amination of methyl indole-3-carboxylate

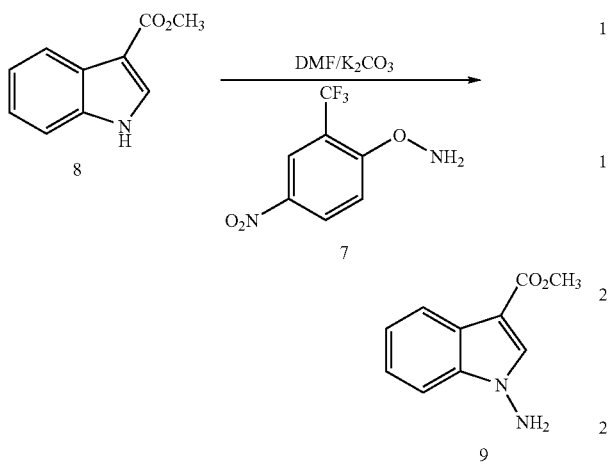

To a solution of indole 8 (175.2 mg, 1.0 mmol) in 3 mL DMF was added finely powdered K$_2$CO$_3$ (415.0 mg, 3.0 mmol) and stirred for 1 h. The aminating reagent 7 (288.0 mg, 1.3 mmol) was added all at once and the reaction mixture stirred for 24 h. Diluted with water and the product was extracted with ethyl acetate. The organic layer was dried and evaporated. The product was purified by silica gel column chromatography using 20% ethyl acetate in hexane to obtain 95 mg (50%) of product 9 as white solids MS (M+1 191).

The invention claimed is:
1. A compound of the formula:

(1)

Ar—L$^2$—CR$^5$ [piperidine ring] N—L$^1$—[fused bicyclic aromatic system with (R$^4$)$_m$, (R$^3$)$_n$, Z$^2$, and NR$^6{}_2$]

and the pharmaceutically acceptable salts thereof, or a pharmaceutical composition thereof, wherein
one Z$^2$ is CA and the other is CR$^1$, wherein R$^1$ is hydrogen or a noninterfering substituent;
A is —W$_i$—COX$_j$Y wherein Y is COR$^2$ wherein R$^2$ is hydrogen or a noninterfering substituent, each of W and X is a spacer preferably of 2-6 Å, and each of i and j is independently 0 or 1;
each R$^6$ is independently H, or a noninterfering substituent, wherein two R$^6$ may optionally form a 5-6 membered ring including the nitrogen to which they are bound;
each R$^3$ is independently a noninterfering substituent;
n is 0-3;
each of L$^1$ and L$^2$ is a linker;
each R$^4$ is independently a noninterfering substituent;
m is 0-4;
Ar is n phenyl group or a thienyl substituted with 0-5 noninterfering substituents, wherein two noninterfering substituents can form a fused ring.

2. The compound of claim 1 wherein each R$^6$ is independently H, alkyl (1-6C), alkenyl (2-6C), alkynyl (2-6C), acyl (1-6C), arylalkyl or arylacyl, or the heteroatom forms of the foregoing, or both R$^6$ are joined to form a ring including the nitrogen to which they are attached which R$^6$ ring may optionally be substituted by alkyl, halo, or alkoxy.

3. The compound of claim 2 wherein both R$^6$ are H or alkyl (1-4C).

4. The compound of claim 2 wherein one R$^6$ is H and the other is acyl.

5. The compound of claim 2 wherein two R$^6$ are joined to form a ring.

6. The compound of claim 2 wherein one R$^6$ is H and the other R$^6$ is alkyl (1-4C).

7. The compound of claim 5 wherein said ring is a piperazine ring, a piperidine ring, or a morpholine ring.

8. The compound of claim 1 wherein A is COXjCOR$^2$, wherein R$^2$ is H, or is straight or branched chain alkyl, alkenyl, alkynyl, aryl, arylalkyl, heteroalkyl, heteroaryl, or heteroarylalkyl, each optionally substituted with halo, alkyl, heteroalkyl, OR, NR$_2$, OCOR, NRCOR, NRCONR$_2$, NRSO$_2$R, NRSO$_2$NR$_2$, OCONR$_2$, CONR$_2$, or R$_3$Si wherein each R is independently H, alkyl, alkenyl or aryl or the heteroatom-containing forms thereof, or
wherein R$^2$ is OR, NR$_2$, SR, NRCONR$_2$, OCONR$_2$, or NRSO$_2$NR$_2$, wherein each R is independently H, alkyl, alkenyl or aryl or the heteroatom-containing forms thereof, and wherein two R attached to the same atom may form a 3-8 member ring and wherein said ring may further be substituted by alkyl, alkenyl, alkynyl, aryl, arylalkyl, heteroalkyl, heteroaryl, heteroarylalkyl, each optionally substituted with halo, SR, OR, NR$_2$, OCOR, NRCOR, NRCONR$_2$, NRSO$_2$R, NRSO$_2$NR$_2$, OCONR$_2$, or R$_3$Si wherein each R is independently H, alkyl, alkenyl or aryl or the heteroatom-containing forms thereof wherein two R attached to the same atom may form a 3-8 member ring, optionally substituted as above defined; and
X, if present, is alkylene.

9. The compound of claim 8 wherein R$^2$ is NR$_2$.

10. The compound of claim 9 wherein NR$_2$ is selected from the group consisting of

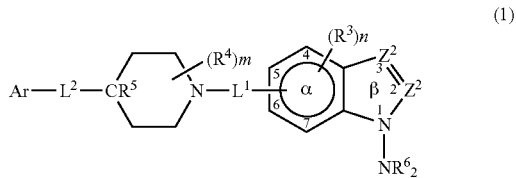

11. The compound of claim 10 wherein NR$_2$ is NHCH$_3$, N(CH$_3$)CH$_2$CHCH$_2$ or N(CH$_3$)OCH$_3$.

12. The compound of claim 10 wherein j is 0.

13. The compound of claim 1 wherein L$^1$ is CO, CHOH or CH$_2$.

14. The compound of claim 13 wherein L$^1$ is CO.

15. The compound of claim 1 wherein R$^5$ is H, OR, NR$_2$, SR or halo, wherein each R is independently H, alkyl, alkenyl or aryl or a heteroatom-containing form thereof.

16. The compound of claim 1 wherein $L^2$ is alkylene (1-4C) or alkenylene (2-4C).

17. The compound of claim 16 wherein $L^2$ is methylene.

18. The compound of claim 1 wherein Ar is phenyl or thienyl each optionally substituted with 0-5 substituents selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof, and wherein two of said optional substituents on adjacent positions can be joined to form a fused, optionally substituted aromatic or nonaromatic, saturated or unsaturated ring which contains 3-8 members.

19. The compound of claim 18 wherein said phenyl or thienyl is unsubstituted or has a single substituent.

20. The compound of claim 19 wherein said optional substituent is halo, OR, or alkyl.

21. The compound of claim 1 wherein $R^4$ is selected from the group consisting of alkyl, alkenyl, alkynyl, aryl, arylalkyl, acyl, aroyl, heteroaryl, heteroalkyl, heteroalkenyl, heteroalkynyl, heteroalkylaryl, NH-aroyl, halo, OR, $NR_2$, SR, SOR, $SO_2R$, OCOR, NRCOR, $NRCONR_2$, NRCOOR, $OCONR_2$, RCO, COOR, alkyl-OOR, $SO_3R$, $CONR_2$, $SO_2NR_2$, $NRSO_2NR_2$, CN, $CF_3$, $R_3Si$, and $NO_2$, wherein each R is independently H, alkyl, alkenyl or aryl or heteroforms thereof and two of $R^4$ on adjacent positions can be joined to form a fused, optionally substituted aromatic or nonaromatic, saturated or unsaturated ring which contains 3-8 members, or $R^4$ is =O or an oxime, oximeether, oximeester or ketal thereof.

22. The compound of claim 21 wherein each $R^4$ is halo, OR, or alkyl.

23. The compound of claim 22 wherein m is 0, 1, or 2.

24. The compound of claim 23 wherein m is 2 and both $R^4$ are alkyl.

25. The compound of claim 1 wherein each $R^3$ is halo, alkyl, heteroalkyl, OCOR, OR, NRCOR, SR, or $NR_2$, wherein R is H, alkyl, aryl, or heteroforms thereof.

26. The compound of claim 25 wherein $R^3$ is halo or alkoxy.

27. The compound of claim 26 wherein n is 0, 1 or 2.

28. The compound of claim 1 wherein $L^1$ is coupled to the α ring at the 4-, 5- or 6-position.

29. The compound of claim 1 wherein $Z^2$ at position 3 is CA and the $Z^2$ at position 2 is CH.

30. The compound of claim 1 wherein $L^2$ is methylene with an aryl, heterocyclic, alkyl or heteroalkyl substituent.

31. The compound of claim 30 where $L_2$ is methylene with a methyl or phenyl substituent.

32. A pharmaceutical composition comprising a therapeutically effective amount of a compound of claim 1 and an acceptable pharmaceutical excipient.

* * * * *